(12) United States Patent
Evelyn et al.

(10) Patent No.: US 12,214,165 B2
(45) Date of Patent: Feb. 4, 2025

(54) AUTO-INJECTION MEDICAL DEVICE SYSTEM

(71) Applicant: ALERJE, INC., Detroit, MI (US)

(72) Inventors: Javier Evelyn, Detroit, MI (US); William Hunter Martin, Detroit, MI (US); Nathan Ivy, Clarendon Hills, IL (US); Dustin Kang, Detroit, MI (US)

(73) Assignee: Alerje, Inc., Detroit, MI (US)

( * ) Notice: Subject to any disclaimer, the term of this patent is extended or adjusted under 35 U.S.C. 154(b) by 837 days.

(21) Appl. No.: 17/273,270

(22) PCT Filed: Sep. 4, 2019

(86) PCT No.: PCT/US2019/049483
§ 371 (c)(1),
(2) Date: Mar. 3, 2021

(87) PCT Pub. No.: WO2020/051201
PCT Pub. Date: Mar. 12, 2020

(65) Prior Publication Data
US 2021/0322678 A1    Oct. 21, 2021

Related U.S. Application Data

(60) Provisional application No. 62/860,726, filed on Jun. 12, 2019, provisional application No. 62/841,360, (Continued)

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3158* (2013.01); *A61M 5/31591* (2013.01);
(Continued)

(58) Field of Classification Search
CPC ........................... A61M 5/31593; A61M 5/20
See application file for complete search history.

(56) References Cited

U.S. PATENT DOCUMENTS 5,358,489 A    10/1994  Wyrick
5,752,621 A     5/1998  Passamante
(Continued)

FOREIGN PATENT DOCUMENTS

EP          2983736 A1      2/2016
JP       2015-213781 A     12/2015
(Continued)

OTHER PUBLICATIONS

European Extended Search Report with Supplementary Search Report dated May 6, 2022, Application No. 19858011.
(Continued)

*Primary Examiner* — Manuel A Mendez
(74) *Attorney, Agent, or Firm* — The Dobrusin Law Firm, P.C.

(57) ABSTRACT

An injector comprising a housing, a control releasably secured to the housing, and a syringe movably positioned within the housing. When released, the control drives the syringe to expose a portion of the syringe outside of the housing.

20 Claims, 47 Drawing Sheets

Related U.S. Application Data filed on May 1, 2019, provisional application No. 62/785,357, filed on Dec. 27, 2018, provisional application No. 62/743,713, filed on Oct. 10, 2018, provisional application No. 62/737,249, filed on Sep. 27, 2018, provisional application No. 62/735,238, filed on Sep. 24, 2018, provisional application No. 62/729,589, filed on Sep. 11, 2018, provisional application No. 62/726,895, filed on Sep. 4, 2018.

(52) U.S. Cl.
CPC ...... *A61M 5/31593* (2013.01); *A61M 5/3202* (2013.01); *A61M 2005/2073* (2013.01); *A61M 2205/3368* (2013.01); *A61M 2205/3569* (2013.01); *A61M 2209/08* (2013.01)

(56) References Cited

U.S. PATENT DOCUMENTS

| | | |
|---|---|---|
| 7,449,012 B2 | 11/2008 | Young et al. |
| 8,048,035 B2 | 11/2011 | Mesa et al. |
| 8,639,288 B1 | 1/2014 | Friedman |
| 8,833,379 B1 | 9/2014 | Kaplan |
| 9,374,120 B1 | 6/2016 | Halloran |
| 9,785,750 B2 | 10/2017 | Coe et al. |
| 10,022,506 B2 | 7/2018 | Pribitkin |
| 10,320,439 B2 | 6/2019 | Greiner |
| 10,589,029 B2 | 3/2020 | Salahshoor Kordestani |
| 11,764,821 B2 * | 9/2023 | Langhans ............ A61M 5/002 |
| | | 455/575.8 |
| 2002/0050462 A1 | 2/2002 | Penney |
| 2004/0140285 A1 | 7/2004 | Vetter et al. |
| 2006/0229569 A1 | 10/2006 | Lavi et al. |
| 2006/0247579 A1 | 11/2006 | Friedman |
| 2011/0196311 A1 | 8/2011 | Bicknell et al. |
| 2013/0079725 A1 * | 3/2013 | Shang .................... A61M 5/20 |
| | | 604/189 |
| 2013/0274666 A1 | 10/2013 | Brereton et al. |
| 2014/0155827 A1 * | 6/2014 | Ostrander ............ A61J 7/0076 |
| | | 604/93.01 |
| 2014/0216979 A1 | 7/2014 | Conarro |
| 2014/0216976 A1 | 8/2014 | Conarro |
| 2014/0243749 A1 * | 8/2014 | Edwards .............. H04B 1/3827 |
| | | 455/73 |
| 2014/0323978 A1 | 10/2014 | Henley et al. |
| 2015/0057616 A1 * | 2/2015 | Shergold ........... A61M 5/31593 |
| | | 604/152 |
| 2015/0080806 A1 | 3/2015 | Pribitkin |
| 2015/0141923 A1 | 5/2015 | Wurmbauer et al. |
| 2015/0328411 A1 | 11/2015 | Friedman |
| 2016/0022914 A1 | 1/2016 | Mounce et al. |
| 2018/0243504 A1 * | 8/2018 | Scott .................... A61M 5/2033 |
| 2019/0374436 A1 | 12/2019 | Townley |
| 2020/0170888 A1 | 6/2020 | Misra |

FOREIGN PATENT DOCUMENTS

| | | |
|---|---|---|
| WO | 2010/056712 A1 | 5/2010 |
| WO | 2012/158135 A1 | 11/2012 |
| WO | 2016/107794 A1 | 7/2016 |
| WO | 2018/148741 A1 | 8/2018 |

OTHER PUBLICATIONS

Indian Examination Report dated Mar. 4, 2022, Application No. 202117008818.
Japanese Patent Office First Office Action dated Apr. 28, 2022, Application No. 2021-536675.
Chinese Notice of Allowance, CN Application No. 20190066463.9 dated Jan. 28, 2023.
International Search Report dated Dec. 12, 2019, Application No. PCT/US2019/049483.

\* cited by examiner

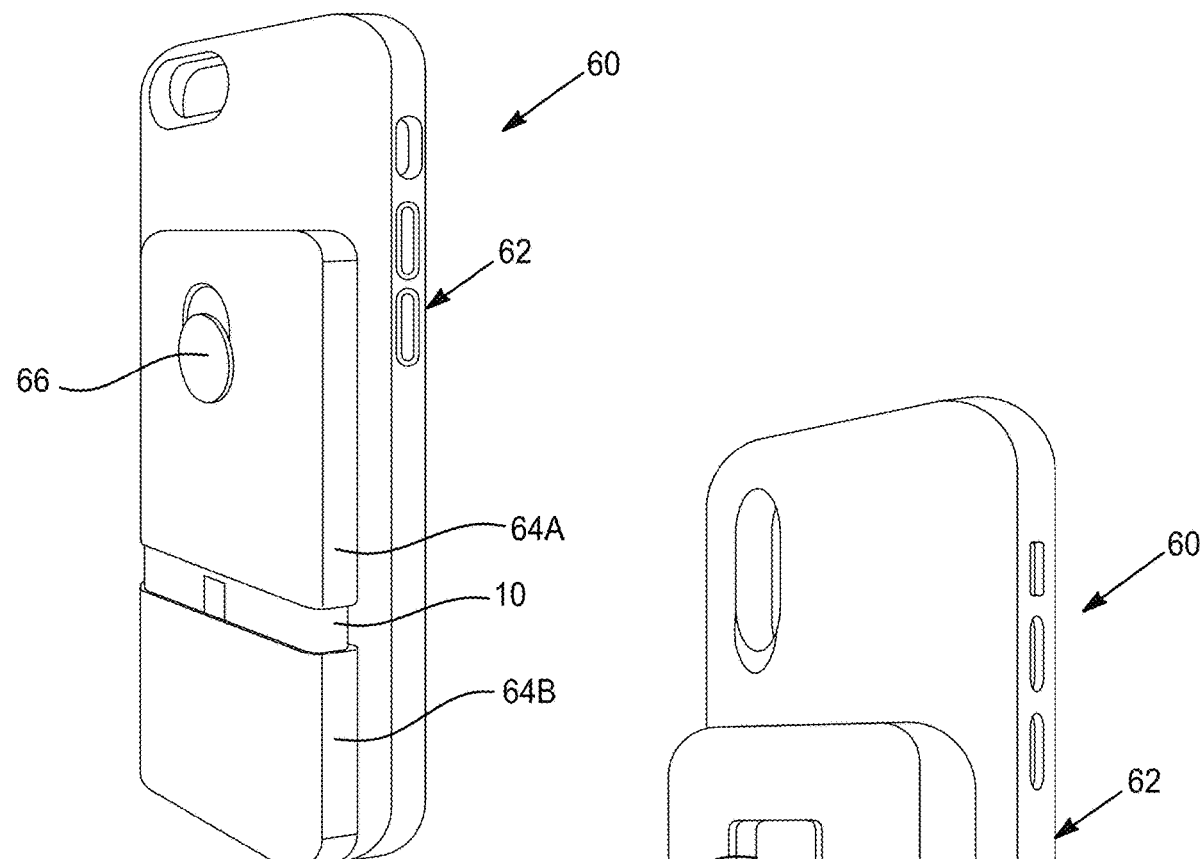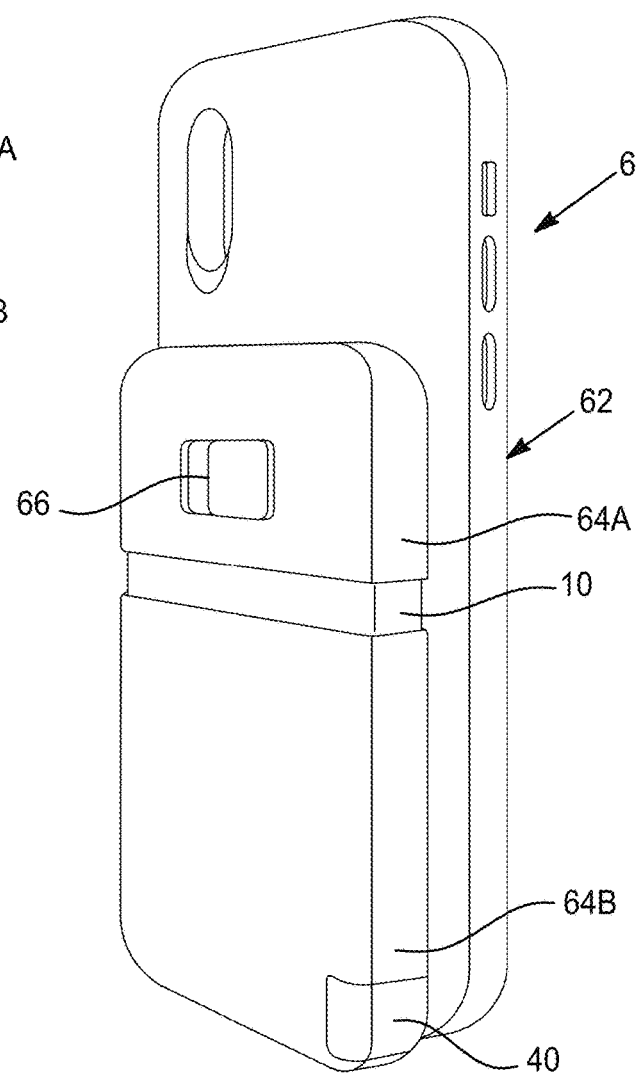
FIG. 1
FIG. 2

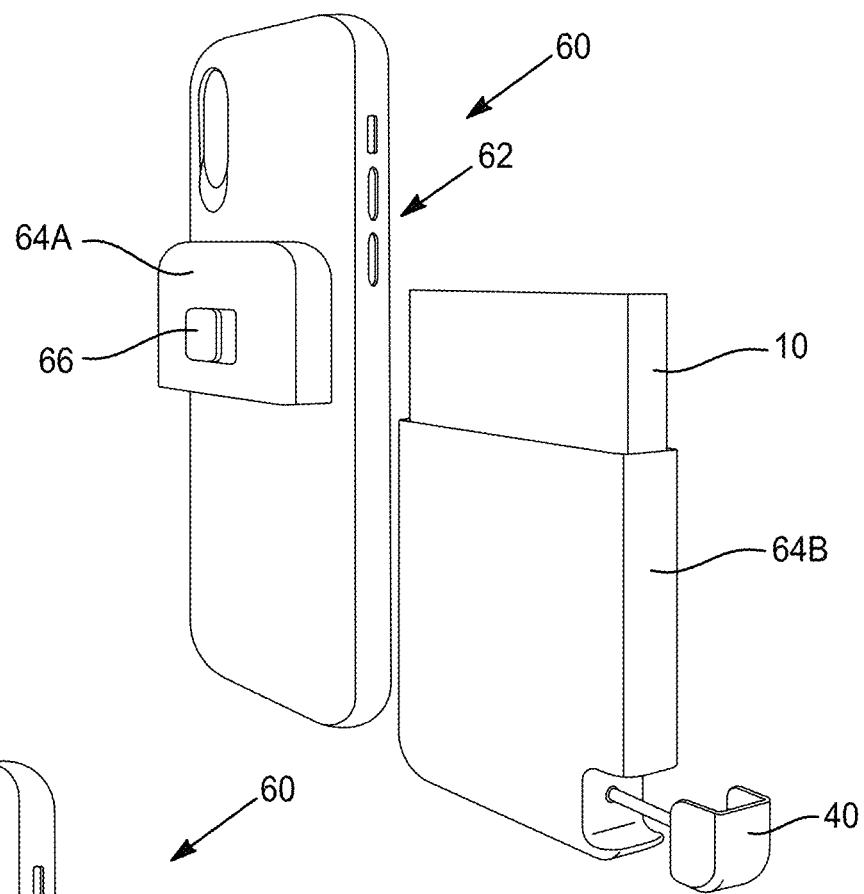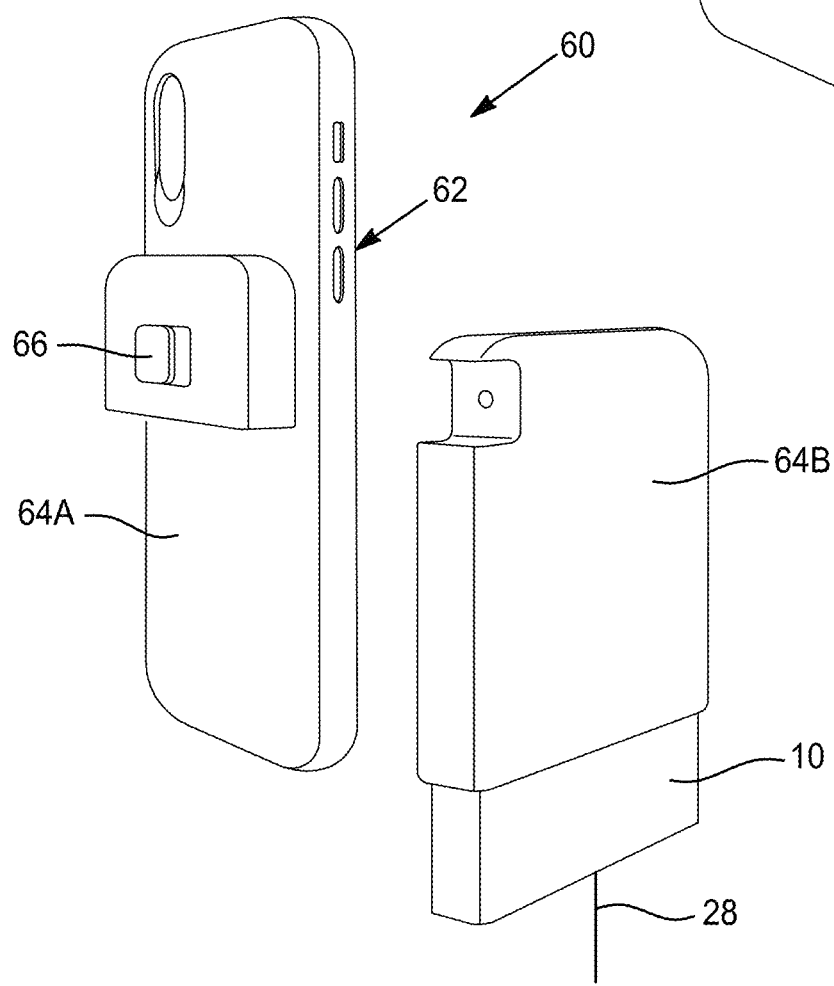

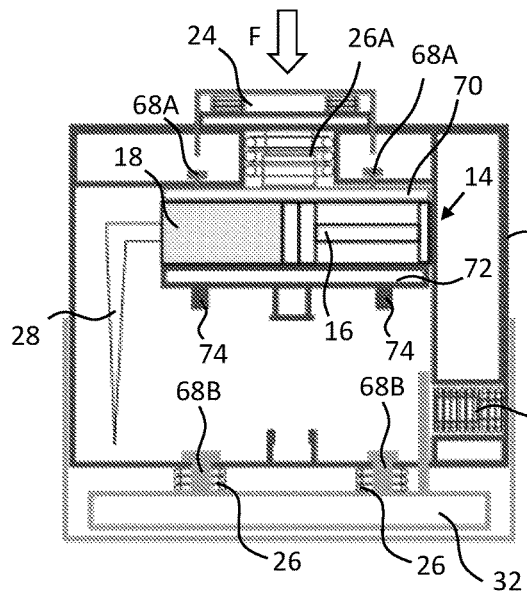
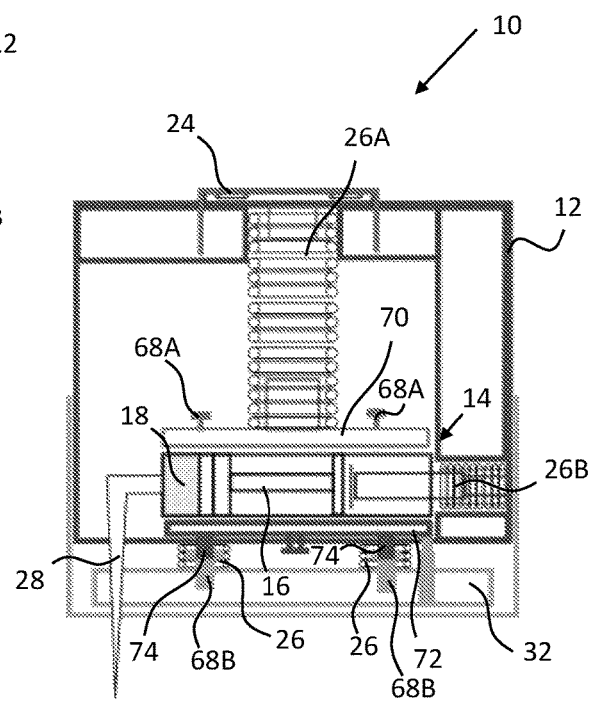
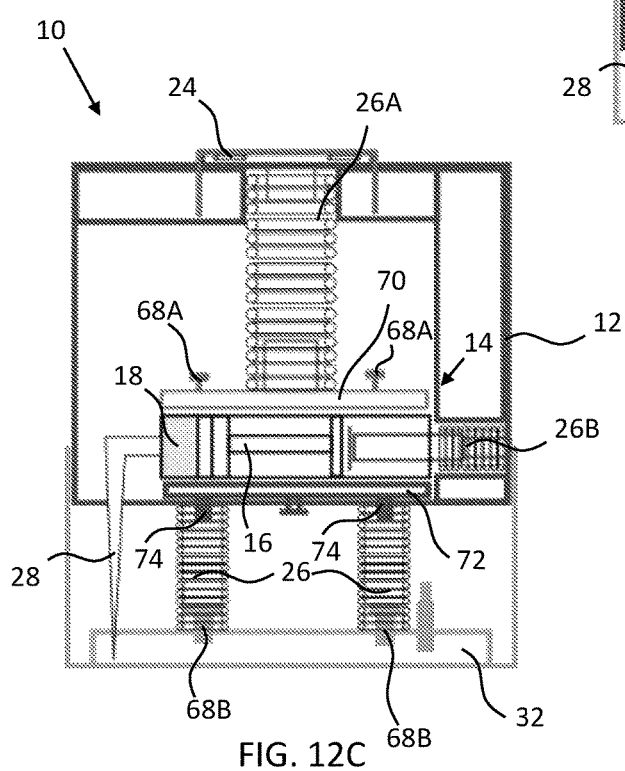
FIG. 12A
FIG. 12B
FIG. 12C

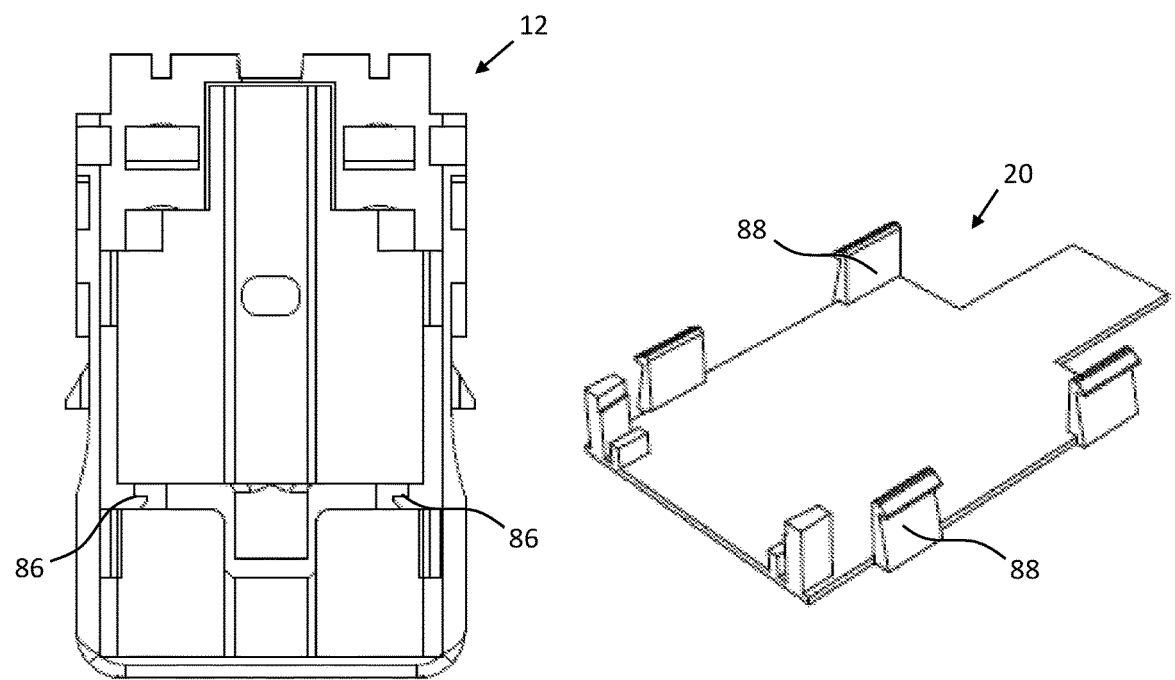
FIG. 28
FIG. 29
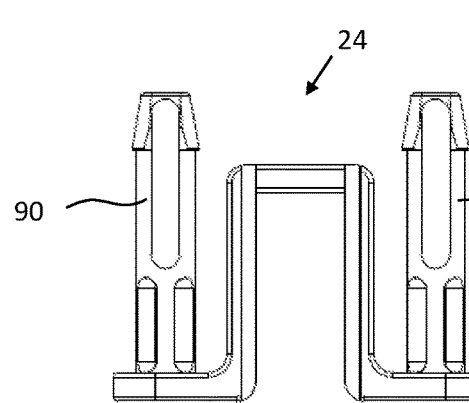
FIG. 30
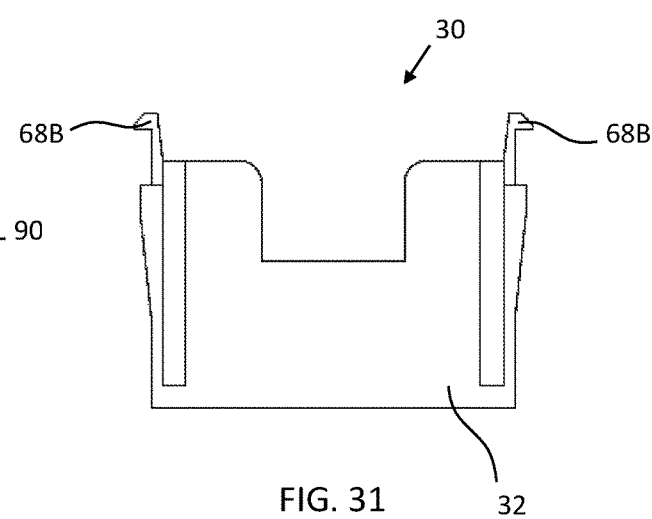
FIG. 31

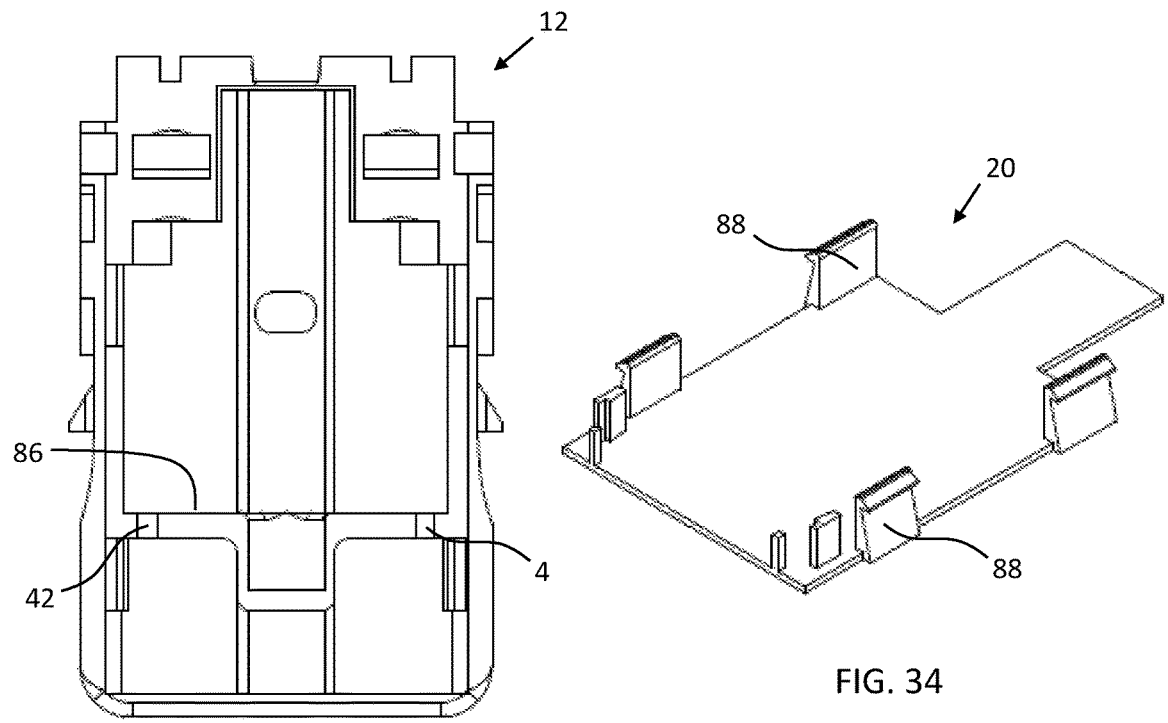
FIG. 33
FIG. 34
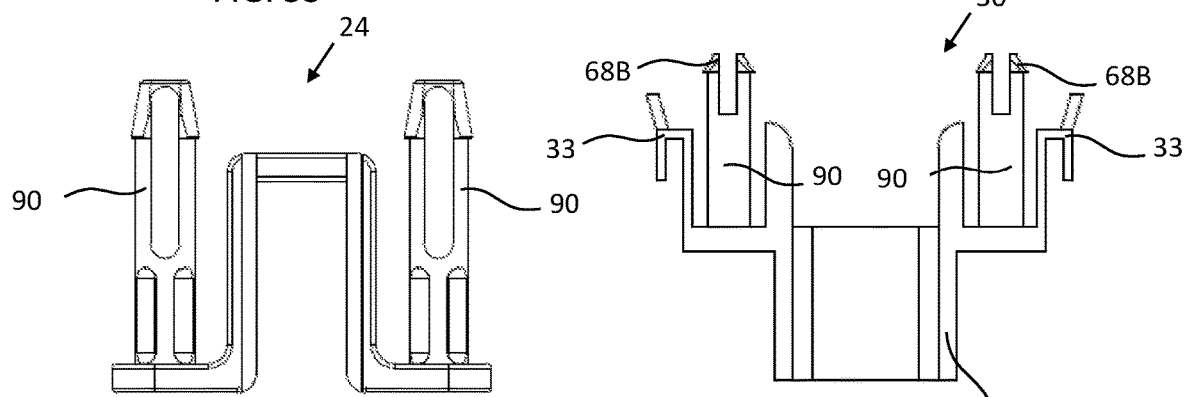
FIG. 35
FIG. 36

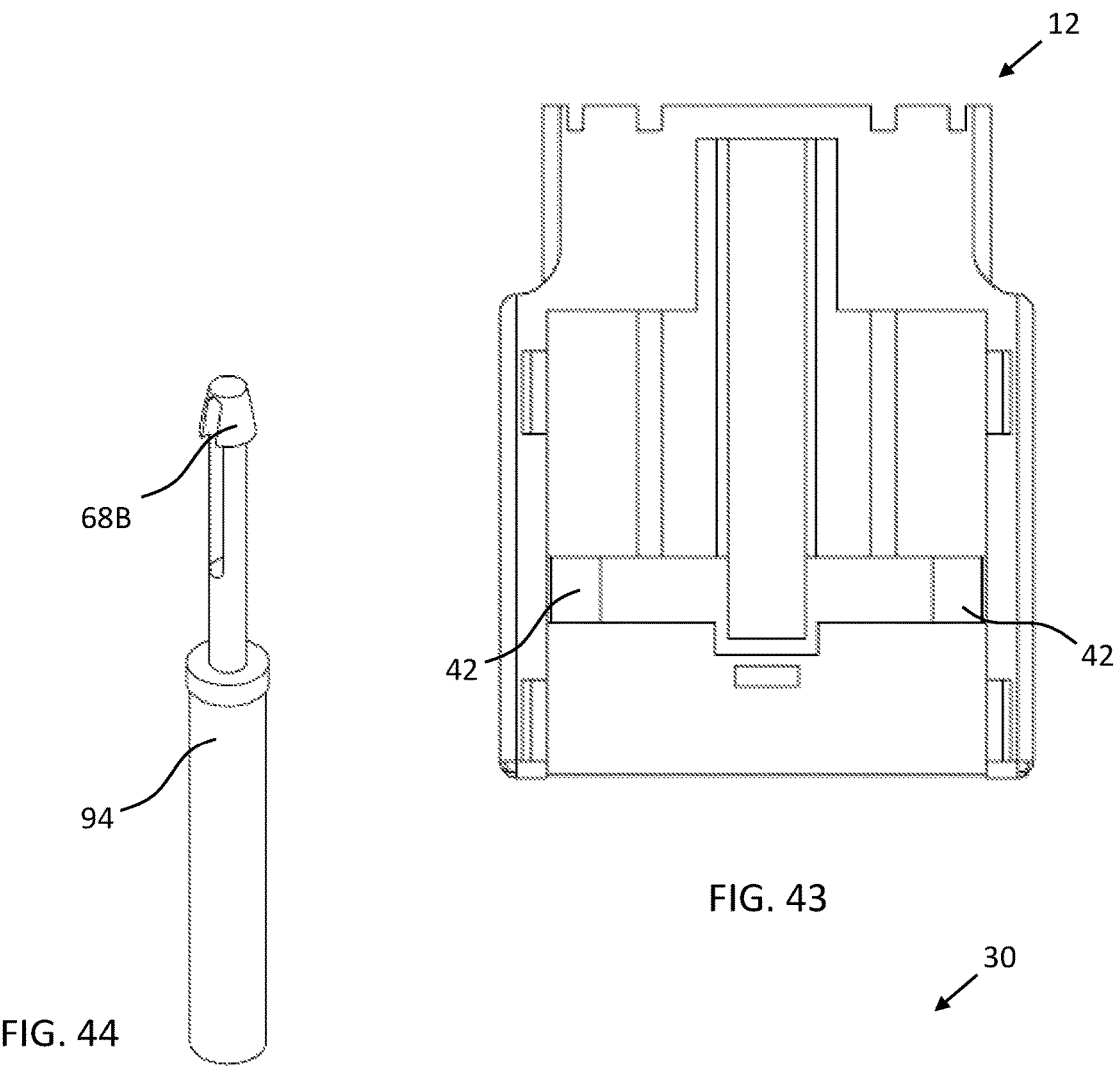
FIG. 44
FIG. 43
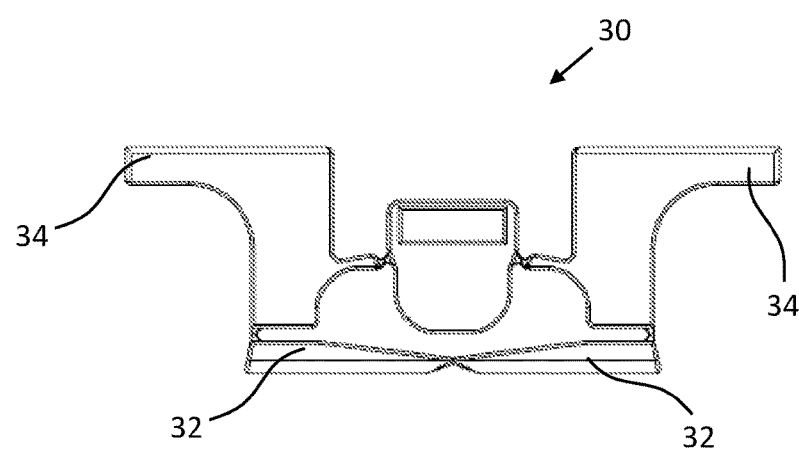
FIG. 45

AUTO-INJECTION MEDICAL DEVICE SYSTEM

FIELD

The present teachings generally relate to automated medical devices. More specifically, the present teachings generally related to auto-injection medical devices to inject one or more medications.

BACKGROUND

Epinephrine auto-injectors (EAI) are life-saving medical devices used by the over 15 million Americans that suffer from food allergies during an anaphylactic reaction. An epinephrine auto injector (EAI) is an emergency injection ("shot") of epinephrine. This medicine is used for life-threatening allergic reactions such as severe swelling, breathing problems, or loss of blood pressure. Allergic, or anaphylactic reactions can be caused by stinging and biting insects, allergy injections, food, medicines, exercise, or other known and/or unknown causes.

EAIs are normally stored in individual protective cases in doses of 0.15 mg to 0.3 mg depending on written prescription. Due to the various responses that patients have from the use of the medication, it is recommended to carry two EAIs.

Similarly, injections of insulin or other medications may be required by the over 30 million people in the United States that suffer from diabetes. Without the injection of insulin, a diabetic may experience severe hypoglycemia, or diabetic shock, which can be life threatening. Therefore, diabetics carry insulin on their person in case of low blood sugar. Insulin is available in an auto injector cartridge for quick use. However, insulin must be stored between 56° F. and 80° F. for cartridges which are in current use. Because insulin injections are required by a large proportion of people with diabetes, it is necessary to keep insulin nearby at all times.

A common issue is that auto injectors may not be readily available when needed. Another issue is that auto injectors may expire without the knowledge of the user. A further issue with auto injectors may be that the user is unaware how to use the injector for an injection. In addition, there are often caregivers, including physicians, nurses and family members who wish to monitor medication use and proper use of an auto injector for an individual, especially when that individual is a child or someone who is elderly.

Examples of such an auto injector can be found in PCT Application No. PCT/US/2018/018031; and U.S. Provisional Application No. 62/726,895, filed on Sep. 4, 2018; 62/729,589, filed on Sep. 11, 2018; 62/735,238, filed on Sep. 24, 2018; 62/737,249, filed on Sep. 27, 2018; 62/743,713, filed on Oct. 10, 2018; and 62/785,357, filed on Dec. 27, 2018, all of which are incorporated by reference herein for all purposes. It would be attractive to have an auto injector that is easily accessible for a user. What is needed is an auto injector that may be stored on a case of a mobile device. It would be attractive to have an injector that automatically injects a medicine into a user with minimal user interface. What is needed is an auto injector having a single control and/or button to perform an injection operation. It would be attractive to have a portable auto injector having a protective casing to protect a user from unwanted contact with one or more components of the auto injector. What is needed is an auto injector with a movable sheath to protect a user from contact with one or more components of the auto injector before injection, after injection, or both.

SUMMARY

The present teachings meet one or more of the present needs by providing an injector comprising: (a) a housing; (b) a control releasably secured to the housing; and (c) a syringe movably positioned within the housing, wherein when released, the control drives the syringe to expose a portion of the syringe outside of the housing.

The present teachings meet one or more of the present needs by providing an injector, wherein: the exposed portion of the syringe is a needle; the syringe houses a medication that is distributed through the needle into a user via a plunger that is driven by the control; the control is moved by one or more biasing members; the injector further comprises further comprising a sheath that movably protects the needle prior to release of the control, after release of the control, or both; the injector is housed within a mobile device case, within an injector case secured to a mobile device case, or both; the control is released via a force applied to a button on the housing that engages the control; a stopper secures the control to the housing so that, when the stopper is removed from the injector, the control is released and engages the syringe; the stopper is a pin movably secured to the housing; the injector is configured for one injection; the injector is configured for a plurality of injections; the one or more biasing members are a spring; the sheath is attached to the housing so that, when the syringe is driven by the control, the syringe contacts a portion of the sheath and releases the sheath from the housing to encapsulate the exposed portion of the syringe; the sheath is secured to the housing via one or more biasing members so that, after injection from the injector, the sheath is biased to extend over the exposed portion of the syringe; the one or more biasing members of the sheath are a spring; the pin releasably engages the button of the housing; the injector case is releasably secured to the phone case; a first section of the injector case is fixedly secured to the phone case and a second section of the injector case is removably secured to the phone case; the second section of the injector case is fixedly attached to the injector; the second section of the injector case is a portion of the housing of the injector; or a combination thereof.

The present teachings meet one or more of the present needs by providing an injector having a sheath, wherein: the sheath is attached to a plate secured within the housing so that, when the syringe is driven by the control, the control contacts and releases opposing fingers securing the sheath, and the sheath in turn releases and extends to encapsulate the exposed portion of the syringe; the sheath is biased via a biasing member so that the sheath extends upon release; the sheath is secured to a projection of the plate and the fingers are rotatably secured to a plurality of holes positioned on the plate; or a combination thereof.

The present teachings meet one or more of the present needs by providing: an auto injector that is easily accessible for a user; an auto injector that may be stored on a case of a mobile device; an injector that automatically injects a medicine into a user with minimal user interface; an auto injector having a single control and/or button to perform an injection operation; a portable auto injector having a protective casing to protect a user from unwanted contact with one or more components of the auto injector; and a movable sheath to protect a user from contact with one or more components of the auto injector before injection, after injection, or both.

The injector may further include one or more near-field communication sensors. The one or more near-field communication sensors may be adapted to identify and/or monitor the location of the medical device with reference to a phone that is connected to the housing. The one or more near-field communication sensors may be adapted to identify and/or monitor the temperature of the medical device. A user may receive a notification that the temperature of the medical device is outside of a predetermined acceptable range. One or more predetermined third-party devices may receive a notification when the medical device is separated from the phone.

BRIEF DESCRIPTION OF THE DRAWINGS

FIG. 1 is a perspective view of a phone case having an injector;
FIG. 2 is a perspective view of a phone case having an injector;
FIG. 3 is a perspective view of a phone case having an injector released from the phone case;
FIG. 4 is a perspective view of a phone case having an injector released from the phone case;
FIG. 12A is a side view of an injector in a resting position;
FIG. 12B is a side view of the injector of FIG. 12A in an engagement position;
FIG. 12C is a side view of the injector of FIG. 12A in an extended position;
FIG. 28 is the housing of the injector of FIG. 27A;
FIG. 29 is a cover for the housing of FIG. 28;
FIG. 30 is the control of the injector of FIG. 27A;
FIG. 31 is the sheath assembly of the injector of FIG. 27A;
FIG. 33 is the housing of the injector of FIG. 32A;
FIG. 34 is a cover for the housing of FIG. 33;
FIG. 35 is the control of the injector of FIG. 32A;
FIG. 36 is the sheath assembly of the injector of FIG. 32A;
FIG. 43 is the housing of the injector of FIG. 42A;
FIG. 44 is the sheath driver of the injector of FIG. 42A;
and FIG. 45 is the sheath assembly of the injector of FIG. 42A.

DETAILED DESCRIPTION

Figures 5, 6:
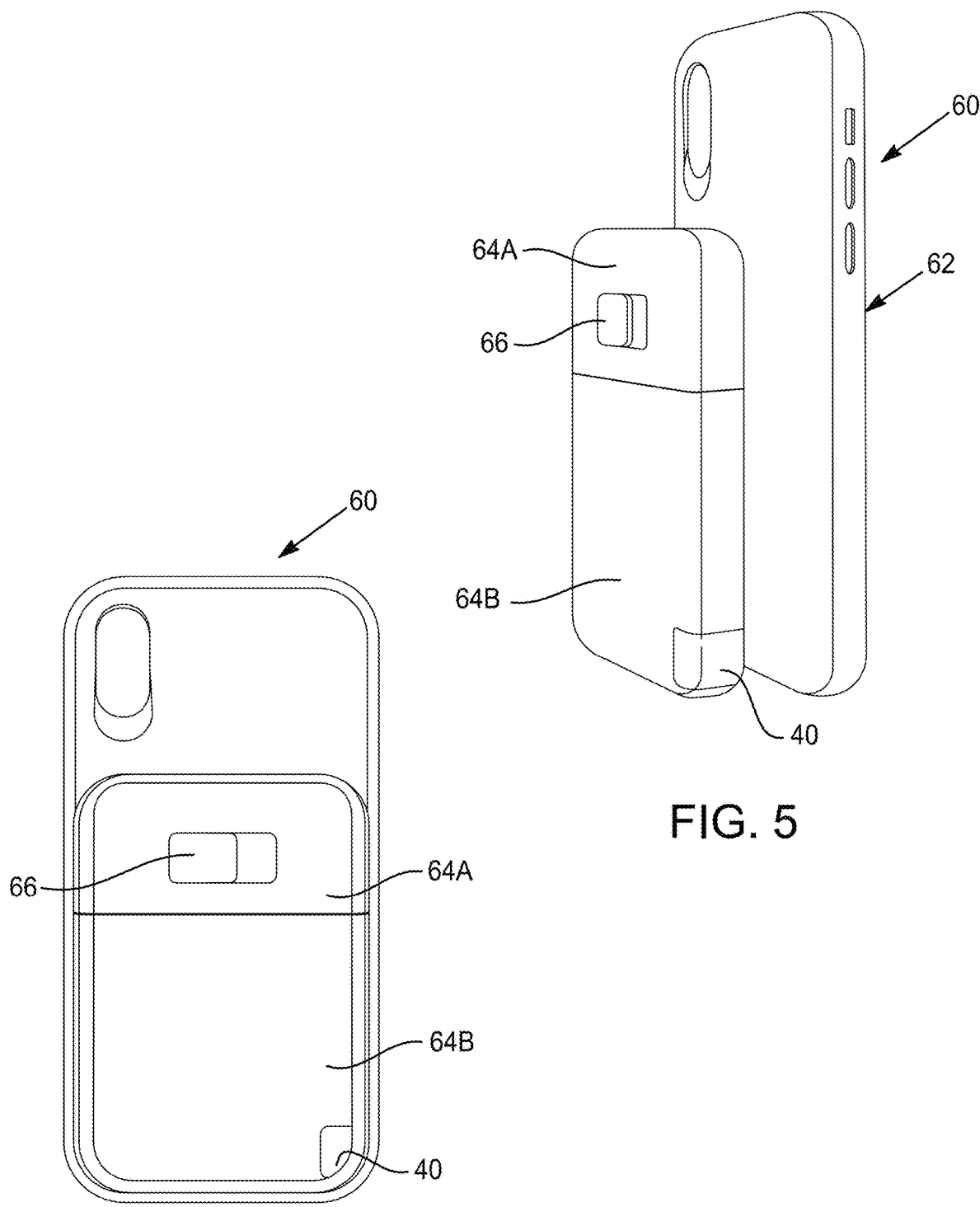
FIG. 5 is a perspective view of an injector case and a phone case.
FIG. 6 is a front view of a phone case having an injector.

This application claims the benefit of the following earlier filed U.S. Provisional Applications 62/726,895, filed on Sep. 4, 2018; 62/729,589, filed on Sep. 11, 2018; 62/735,238, filed on Sep. 24, 2018; 62/737,249, filed on Sep. 27, 2018; 62/743,713, filed on Sep. 10, 2018; 62/785,357, filed on Dec. 27, 2018; 62/841,360, filed on May 1, 2019; and 62/860,726, filed on Jun. 12, 2019, all of which are incorporated herein for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein relate to a portable injector. The injector may function to inject one or more users with a medication. The injector may be fully or partially automated to inject a user with medication. The injector may be any injector carrying fast-acting or necessary medicine. The injector may contain temperature sensitive material. The injector may include an epinephrine auto injector (EAI), an inhaler, an insulin auto-injector (IAI), and/or the like. The epinephrine or other medication may be in the form of a nasal spray, a fluid, or both. More particularly, the teachings are directed to an injector capable of attaching to a mobile device. The injector may be integrated into an attachment device. The injector may be removably attachable to the attachment device. Mobile devices may include computing devices small enough to be held and operated by a hand of an individual, include mobile technology which uses radio waves to transmit and receive data (e.g., 3G, 4G, Bluetooth, wi-fi, near field communication). Mobile devices may include mobile phones, smartphones, tablet computers, the like, or any combination thereof.

The injector may include a housing. The housing may function to house one or more components of the injector. The housing may house a syringe, one or more biasing members, one or more actuators, one or more controls, additional components, or a combination thereof. The housing may encompass the syringe so that the syringe may move within the housing. For example, the syringe may move in one or more directions relative to the housing when enclosed in the housing based upon one or more biasing members. The housing may include one or more cavities, one or more walls, one or more pockets, one or more segments, or a combination thereof. The housing may include one or more holes, one or more protrusions, one or more projections, one or more recesses, or a combination thereof. The housing may be any size and shape configured to house the syringe, additional components, or both. The housing may be integrally formed or may include a plurality of pieces assembled together. The housing may include one or more openings so that the syringe may protrude from the housing a contact a user for injection of a medicine.

The housing may include one or more platforms. The platforms may function to secure a position of the syringe. The platforms may be fixedly positioned or may move freely. For example, the platforms may move between an initial position and an injection position to inject a user with the medication. The platforms may be a plurality of platforms. For example, a first platform and a second platform may sandwich a syringe to secure the syringe during movement. The platforms may be structurally rigid. The platforms may be mechanically articulated via one or more biasing members. Alternatively, the platforms may be articulated via one or more actuators, motors, or both.

The housing may include a cap. The cap may function to allow opening and closing of a portion of the housing. The cap may be a piece of the housing that releases from the housing to allow replacement of the syringe, inspection of the interior of the injector, or both. The cap may include threading to secure the cap to the housing. The cap may be free of threading. For example, the cap may be secured to the housing using a press-fit condition between the cap and the housing.

The housing may include a cover. The cover may function to enclose all or a portion of the housing. The cover may be configured to protect one or more internal cavities of the housing from outside debris, moisture, or both. The cover may enclose a syringe located in the housing to maintain sterilization of the syringe. The cover may be removable. For example, the cover may be removed to replace a syringe within the injector. The cover may be hermetically sealed with the housing. The cover may be shaped substantially similar to one or more sides of the housing. The cover may be integrally formed with the housing may be secured to the housing. For example, the cover may be pivotally engaged to the housing via one or more hinges. The cover may be secured to the housing via one or more adhesives, one or more fasteners, or a combination thereof. The cover may be structurally rigid. The cover may be transparent so a user of the injector may see one or more components located within the housing, such as the syringe.

The cover may include one or more tabs. The tabs may function to secure the cover to the housing. The tabs may project from a surface of the cover. The tabs may be inserted into one or more slots, notches, or both of the housing. The tabs may be flexible to flex around a peripheral edge of the housing to secure the cover to the housing. The tabs may be a tooth, latch, hook, or a combination thereof. The tabs may be positioned anywhere along the cover. The tabs may be positioned along one or more peripheral edges of the cover. The tabs may project at any desired angle from the housing. The tabs may be any size and shape based on the size and shape of the housing. The tabs may be integrally (i.e., monolithically) formed with the cover. For example, the cover may be an injection-molded piece formed with a plurality of tabs.

The syringe may function to store and distribute medication into a user. The syringe may include a needle, plunger, or both to administer the medication. The injector may include replaceable or customizable syringes to replace a medication, interchange syringe sizes, or both. The syringe may be positioned within the housing of the injector so that the syringe is protected from tampering prior to injection. A portion of the syringe or the entire syringe may be driven to contact a user via one or more biasing members, one or more actuators, or both. The syringe may be any size and shape for a desired application, a desired medication, or both.

The syringe may include a plunger. The plunger may function to drive a medication stored in the syringe into a needle of the syringe. The plunger may provide a functional fit within a cavity of the syringe. For example, the plunger may include one or more compressible members that frictionally abut an inner tube of the syringe to drive the medication in a desired direction. The plunger may include a shaft, and the shaft may connect to a frictional member that directly contacts the medication. The frictional member may be a washer, nipple, stopper, or a combination thereof. The plunger may be removably secured to the syringe. For example, the plunger may be stored on an exterior side of the syringe, the housing, or both prior to injection, and the plunger may be inserted into the syringe for injection.

The plunger may drive a medication into a needle. The needle may function to administer a medication into a user, an object, or both. The needle may be any needle configured to receive a medication, administer a medication into a user, or both. The needle may be any medical needle that is configured for use with a syringe. The needle may be replaceable, customizable, or both. The needle may vary in size, shape, or both. For example, the needles having different lengths may be interchangeable based on a desired application.

The needle may be housed within a sterilization cover. The sterilization cover may function to protect the needle from debris, bacteria, or both prior to injection. The sterilization cover may be any cover that protects the needle prior to injection. The sterilization cover may be sheared, compressed, fractured, or a combination thereof during an injection operation. For example, the needle may pierce through the sterilization cover during actuation of the syringe. The sterilization cover may be a laminate, capsule, film, housing, or a combination thereof. The sterilization cover may be any size and shape to house the needle.

A medication may be stored within the syringe. The medication may be injected into a user. The medication may be any medication configured to be administered with a syringe. The medication may be a liquid, mixture, solution, or a combination thereof. For example, the medication may be an epinephrine, amphetamine, anesthetic, analgesic, antacid, antibiotic, anticoagulant, antidepressant, antidote, antihistamine, anti-inflammatory, antiretroviral, contraceptive, decongestant, suppressant, steroid, vaccine, or a combination thereof.

The syringe may be driven within the housing via a control. The control may function contact and move the syringe in a desired direction. The control may move the syringe so that the needle of the syringe is exposed outside of the housing to contact a user. The control may be structurally rigid to drive the syringe. The control may include one or more bends, one or more angles, one or more protrusions, one or more projections, one or more tabs, one or more ears, or a combination thereof. The control may drive the syringe into a desired position. The control may drive a plunger of the syringe so that the plunger drives the medication into the needle for injection. The control may be biased against one or more walls of the housing. The control may release a sheath assembly or a portion of a sheath assembly during movement of the control. For example, the control may drive the syringe until the control abuts an inner surface of the housing (e.g., one or more shelves within the housing) that is securing one or more sheath engaging mechanisms of the sheath assembly, thereby releasing the sheath engaging mechanisms and allowing the sheath assembly to extend freely. Alternatively, the control may secure the sheath assembly in a compressed stated prior to activation, and after activation of the control (i.e., release and driving of the control), the sheath assembly is released and allowed to extend freely.

The control may be released from a biased compressed position via one or more buttons. The button may function to initiate movement of the control. The button may function to initiate injection of the medication via articulation of the injector. A force may be applied to the button to initiate injection. The button may be any size and shape. The button may be positioned along an exterior surface of the housing. The button may be any object that may be pressed for operation of the injector.

The button may initiate injection after release of a stopper. The stopper may function to maintain a resting position of the injector. The resting position may be any position of the injector prior to injection. For example, the resting position may include the control abutting an interior surface of the housing so that, when initiated, the control is drive via one or more biasing members to drive the syringe and initiate injection. The stopper may maintain a position of the control relative to the housing, the syringe, or both. The stopper may be a pin, latch, hook, projection, fastener, clip, or a combination thereof. For example, the stopper may be a pin that is released from a receiving hole extending through the housing and control so that the control may move relative to the housing. Alternatively, the stopper may be a sliding latch that is released from engaging features of the control so that the control may move relative to the housing. The stopper may be an integral component of the control, the housing, or both that is fractured from the control, the housing, or both to initiate movement of the control relative to the housing. The stopper may be moved to directly initiate articulation of the control (i.e., begin an injection movement). Alternatively, the stopper may be moved to allow one or more additional components, such as a button, to be activated and initiate articulation of the control. The stopper may determine a starting point of the syringe, sheath, or both prior to activation.

The needle may extend outside of the housing and, after injection, be encapsulated by a sheath assembly. The sheath assembly my function to extend a sheath around an exposed portion of the needle. The sheath assembly may be positioned within the housing, outside of the housing, or both. For example, a mounting portion of the sheath assembly may be secured within the housing while an articulated sheath of the sheath assembly may extend outside of the housing. The sheath assembly may be positioned near the needle so that the sheath assembly may encapsulate the needle. The sheath assembly may include one or more stationary (i.e., fixed) components, one or more movable components, or both.

The sheath assembly may include a plate. The plate may function to secure one or more components of the sheath assembly to the housing. The plate may be secured within the confines of the housing so that a sheath of the sheath assembly may be positioned around the needle. The plate may be any size and shape to secure the sheath assembly to the housing. The plate may structurally rigid. The plate may be flexible.

The plate may include one or more projections. The projections may function to secure one or more components of the sheath assembly. The projections may function as an attachment portion of the plate. For example, a biasing member, a sheath, or both may be secured to the plate via the projections. The projections may be any size and shape. For example, a first set of projections may be substantially cylindrically shaped while a second set of projections may be substantially rectangularly shaped. The projections may projection from any surface of the plate at any angle. The projections may project at an angle of about 30 degrees or more, about 60 degrees or more, or about 90 degrees or more from a surface of the plate. The projections may project at an angle of about 170 degrees or less, about 140 degrees or less, or about 110 degrees or less. The projections may be monolithically (i.e., integrally) formed with the plate. The projections may be secured to the plate as a secondary component. The projections may be positioned anywhere along the plate.

One or more holes of the plate may be used in conjunction with, or in lieu of, the projections to secure one or more components of the sheath assembly. The holes may function to secure one or more components of the sheath assembly to the plate. The holes may be positioned anywhere along the plate. The holes may be any size and shape. The holes may include one or more chamfered edges. The holes may include one or more lubricants around one or more edges. The holes may extend through an entire thickness of the plate or more partially extend through a thickness of the plate. The holes may movably secure one or more fingers of the sheath assembly. Alternatively, one or more holes may be positioned within the housing to allow one or more portions of the sheath assembly to move within the housing.

The fingers may function to secure a sheath in a desired position. The fingers may function to release the sheath so that the sheath may articulate to a desired position. The fingers may function to articulate the sheath to a desired position. The fingers may be secured within the holes of the plate so that the fingers rotatably move about an axis of the hole. The fingers may include one or more engaging features that secure the fingers in the holes. The one or more engaging features may be a projection, button, finger, extension, hook, latch, fastener, or a combination thereof. For example, the engaging features may be a button the is substantially shaped like the holes so that the button creates a press-fit condition with the hole to allow rotation of the finger about an axis of the hole. The fingers may articulate between one or more positions. The fingers may articulate between an engaged position where the fingers are securing the sheath in a first position and a released position where the fingers are disengaged from the sheath so that the sheath may move to a second position. The fingers may articulate between the one or more positions via engagement of the control. For example, the control may contact the fingers and articulate the fingers away from the sheath so that the sheath is released and free to move to an extend position. The fingers may be positioned within the housing. The fingers may include one or more securing features to engage the sheath. For example, the finger may include a hook that is received by one or more openings of the sheath. The fingers may articulate to rotate one or more portions of the sheath until the sheath extends around an exposed portion of the syringe (e.g., an exposed portion of the needle). The fingers may articulate via a force applied to a portion of the fingers. The fingers may be integrally (i.e., monolithically) formed with the sheath so that any articulation of the fingers results in articulation of the sheath. The interconnection between the fingers and the sheath may be a joint, bend, thinner thickness along a portion of the sheath, or a combination thereof.

The sheath may function to house the needle of the syringe after injection to prevent unwanted contact with the needle. The sheath may extend from the housing, be integrally formed with the housing, or both. The sheath may be removable attached to the housing. The sheath may automatically encapsulate the needle after injection. For example, the sheath may be biased against an exterior surface of the housing, a plate within the housing, or both, and one or more protrusions of the control may contact the fingers to release the sheath. After the needle is removed from contact with a user, the released sheath may encapsulate the needle via one or more biasing members. The sheath may be structurally rigid or flexible. The sheath may include one or more bendable or movable portions. The sheath may move between one or more positions. For example, the sheath may move between a first position where the sheath is biased away from the exposed needle and a second position where the sheath is unfolded and encapsulates the needle. The sheath may include one or more foldable portions that fold around the exposed needle. The sheath may include one or more holes so that the needle may extend through the sheath prior to the sheath encapsulating the exposed needle. The sheath may be secured to the plate of the sheath assembly. The sheath may include one or more holes that are secured to the projections of the plate. The sheath may be positioned substantially near the fingers, biasing member, or both. The sheath may be secured to the fingers, biasing member, or both. The sheath may be collapsible. The sheath may include one or more bend points. The one or more bend points may be monolithically formed with the sheath and allow for the sheath to articulate based on a biasing force from one or more biasing members.

Movement of the sheath may be stopped via a sheath brake. The sheath brake may function to prevent movement of the sheath beyond a desired length. The sheath brake be positioned to allow movement of the sheath freely until the sheath extends around an exposed portion of the syringe yet prevents the sheath from overextending and/or disconnecting from the housing. The sheath brake may be a portion of the housing. The sheath brake may be a portion of the sheath assembly. The sheath brake may be a wedge, projection, hook, latch, peg, or a combination thereof. The sheath brake may prevent over extension of the sheath, retraction of the sheath, or both. For example, the sheath brake may be one or more flexible portions of the sheath extending outwardly from the sheath to abut one or more teeth located along an inner surface of the housing so that the sheath brakes prevent retraction of the sheath. The teeth may be positioned anywhere within the housing. For example, the teeth may be projecting from one or more interior walls of the housing to abut the sheath brake and prevent movement in a retraction direction yet allow movement in an extension direction, or vice versa.

The sheath may be releasably secured to a portion of the housing, a portion of the control, a portion of the syringe, or a combination thereof by one or more engaging mechanisms. The engaging mechanisms may function to connect the sheath to the housing, control, syringe, or a combination thereof to prevent movement of the sheath prior to activation of the injector. The engaging mechanisms may release from the housing, the control, the syringe, or a combination thereof to allow movement of the sheath so that the sheath may extend around an exposed portion of the syringe after injection. The engaging mechanisms may be adapted to secure the sheath in one or more holes along the housing. The one or more holes may be any size and shape. The one or more holes may be positioned anywhere along an outer surface of the housing, within the housing, or both. For example, the engaging mechanisms may secure the sheath in one or more holes within the housing by extending through the holes. The engaging mechanisms may be a push-clip that releases from the housing by an applied force. The force may be applied through activation of the injector, driving of the control, or both. For example, the control may release and impact the engaging mechanisms, thereby release the engaging mechanisms and the sheath. The engaging mechanisms may be a latch, clasp, hook, clip, finger, arm, or a combination thereof. The engaging mechanisms may engage one or more shelves (e.g., one or more inner surfaces of the housing, one or more surfaces of the control, or both that are configured to receive and/or secure the engaging mechanisms) prior to release. The one or more shelves may extend away from the engaging mechanisms to allow movement of the sheath or the engaging mechanisms may be bent, moved, or otherwise released from the shelves to allow movement of the engaging mechanisms.

The engaging mechanisms may be supported by one or more shelves. The shelves may function to engage a portion of the sheath assembly. The shelves may function to prevent movement of the sheath prior to injection of the syringe. The shelves may receive, support, or both one or more engaging mechanisms of the sheath assembly. The shelves may be an inner surface of the housing. The shelves may be a portion of the control. The shelves may be shaped substantially to receive the engaging mechanisms. The shelves may be a notch, cutout, divot, planar surface, step, or a combination thereof.

One or more biasing members may be positioned within the injector. The one or more biasing members may function to bias the sheath, the control, or both of the injector. The one or more biasing members may drive the sheath, the control, or both during an injection operation. For example, a first set of biasing members may drive the control to move the syringe while a second set of biasing members may drive the sheath to encapsulate the needle after injection. The first set and second set of biasing members may be similar or dissimilar. The one or more biasing members may be a spring, elastic member, compressible member, or a combination thereof.

The one or more biasing members may be positioned along columns of the control, the sheath assembly, or both. The columns may function to secure a position of the biasing members within the injector. The columns may be positioned within an inner portion of the biasing members. For example, the columns may extend within a spring so that the coils of the spring are wrapped around the columns. The columns may be any desired size and shape. Alternatively, the biasing members may be free of connection to one or more columns and may be positioned anywhere within the housing to move the sheath assembly, the control, or both.

The one or more biasing members may be used in lieu of, or in conjunction with, one or more actuators. The one or more actuators may function to drive the syringe, the sheath, or both. The one or more actuators may be a linear actuator secured to the syringe, the sheath, or both. The one or more actuators may be actuated based on initiation of the button of the injector. The injector may include a plurality of actuators. For example, a first actuator may drive the syringe while a second actuator may drive the sheath after injection.

The sheath may be driven by one or more sheath drivers. The sheath drivers may function to apply a force on a portion of the sheath assembly to move the sheath. The sheath drivers may apply a force on the sheath assembly via one or more biasing members. For example, the sheath drivers may extend through holes within the housing to apply a force to one or more fingers of a sheath assembly. The force applied may articulate the fingers, which in turn articulate the sheath. The sheath drivers may include an engaging mechanism. For example, upon activation of the injector, the engaging mechanism of the sheath drivers may be released simultaneously with the control so that the drivers apply a force on the sheath assembly. The sheath drivers may be any size and shape. The sheath drivers may have a substantially columnar portion to receive one or more biasing members, extend through one or more holes within the housing, or both. The sheath drivers may be positioned anywhere within the housing.

The one or more actuators may receive a signal from a controller of the injector. The controller may function to control actuation of the actuators, one or more additional electrical components, or both. The controller may communicate with a button of the injector. The controller may communicate with one or more external electrical components. For example, the controller may be in communication with a mobile phone, or the controller may be a controller of a mobile phone secured to the injector. The controller may include a printed circuit board (PCB), one or more transistors, one or more capacitors, one or more memory storage units, or a combination thereof. The controller may be housed in the housing of the injector or may be wireless connected to the injector. The controller may include an internal power unit. The power unit may be replaceable, rechargeable, or both.

The injector may be secured to an electronic device, a case of an electronic device, or both. For example, the injector may be secured in a mobile phone case. The phone case may function to house a mobile phone, the injector, or both. For example, a back section of the phone case may house the mobile phone while a front section of the phone case may secure the injector. The phone case may be configured for any phone size and shape. The phone case may be structurally rigid, flexible, or both. The phone case may include one or more projections, one or more cavities, one or more holes, one or more protrusions, one or more buttons, one or more latches, or a combination thereof.

The phone case may include an injector case. The injector case may function to house the injector prior to use. The injector case may be integrally formed with the phone case, removably secured to the phone case, or both. The injector case may include one or more sections integrally formed together, removably attached to each other, or both. For example, the injector case may include a first injector case section and an opposing second injector case section so that the second injector case section may slide away from the first injector case section to expose the injector for use.

The first and second injector case sections may be secured to one another via a release latch that may be toggled between a locked position (i.e., the first and second injector case sections are fixedly secured to one another) and an unlocked position (i.e., the second injector case section may release from the first injector case section, or vice versa). The release latch may function removably secure the first and second injector case sections, the injector housed within the first and second injector case sections, or both. The release latch may be any mechanical locking mechanism that may releasably secure the injector case sections. The release latch may include a button, toggle, switch, latch, tab, pin, or a combination thereof. The release latch may be integrally formed with the injector case, or may be removed from the injector case.

The phone case, the injector, or both may include one or more sensors. The sensors may function to communicate between a mobile device and the injector. The sensors may be attached to the phone case so that the injector abuts the sensors when secured in the phone case. The sensors may be a near-field communication (NFC) sensor. The NFC sensor may determine a position of the injector relative to the phone case, the injector case, a mobile device, or a combination thereof. The sensors may be a temperature sensor. The temperature sensor may determine a temperature of the injector, a temperature of the medication within the injector, or both. The sensors may relay a message to one or more users of the mobile device or one or more third-parties allowed to receive information regarding the injector. For example, a user of the mobile device may receive notification when the injector is reaching a heightened temperature that may be harm the medication dictated by the sensor. Alternatively, a third-party may be notified when an injector requires replacement of the syringe, when the injector is used, or both.

Turning now to the figures, FIGS. 1 and 2 illustrate a perspective view of phone case 60 housing an injector 10 in accordance with the present teachings. The phone case 60 includes a back section 62 for receiving a mobile device (not shown). An injector case 64 including a first injector case section 64A and a second injector case section 64B is secured to a front section of the phone case 60 (i.e., a surface opposing the back section 62). A release latch 66 is located on the first injector case section 64A. The first injector case section 64A and the second injector case section 64B may be separated from one another, revealing the injector 10 located therein. Movement of the release latch 66 may determine whether the first injector case section 64A and the second injector case section 64B are in a disconnected position (as shown), a connected position encapsulating the injector 10, or both. As shown in FIG. 2, the injector 10 may include a removable stopper 40 that may be removed by a user to allow activation of the injector 10.

FIG. 3 illustrates a perspective view of a phone case 60 having an injector 10 released from the phone case 60. The phone case 60 includes a back section 62 for receiving a mobile device (not shown). An injector case 64 including a first injector case section 64A and a second injector case section 64B is secured to a front section of the phone case 60 (i.e., a surface opposing the back section 62). A release latch 66 is located on the first injector case section 64A. As shown, the first injector case section 64A and the second injector case section 64B may be separated from one another, revealing the injector 10 located therein. Movement of the release latch 66 determines whether the first injector case section 64A and the second injector case section 64B are in a disconnected position (as shown), a connected position encapsulating the injector 10, or both. The injector 10 further includes a stopper 40, whereby a user may remove the stopper 40 to allow activation of the injector 10 (see FIGS. 7 and 8).

FIG. 4 illustrates a perspective view of a phone case 60 having an injector 10 released from the phone case 60. The phone case 60 includes a back section 62 for receiving a mobile device (not shown). An injector case 64 including a first injector case section 64A and a second injector case section 64B is secured to a front section of the phone case 60 (i.e., a surface opposing the back section 62). A release latch 66 is located on the first injector case section 64A. As shown, the first injector case section 64A and the second injector case section 64B may be separated from one another, revealing the injector 10 located therein. Movement of the release latch 66 determines whether the first injector case section 64A and the second injector case section 64B are in a disconnected position (as shown), a connected position encapsulating the injector 10, or both. The injector 10 further includes a stopper (not shown), whereby a user may remove the stopper to allow activation of the injector 10 (see FIGS. 3, 7, and 8). Once activated, a user may inject a medication via an actuated needle 28 housed within the injector 10.

FIG. 5 illustrates a perspective view of an injector case 64 disconnected from a phone case 60. The phone case 60 includes a back section 62 for receiving a mobile device (not shown). An injector case 64 including a first injector case section 64A and a second injector case section 64B is removably secured to a front section of the phone case 60 (i.e., a surface opposing the back section 62). A release latch 66 is located on the first injector case section 64A. The first injector case section 64A and the second injector case section 64B may be separated from one another, revealing an injector located therein (see FIGS. 1-4). Movement of the release latch 66 may determine whether the first injector case section 64A and the second injector case section 64B are in a disconnected position, a connected position encapsulating the injector (as shown), or both. The injector 10 further includes a stopper 40, whereby a user may remove the stopper 40 to allow activation of the injector 10 (see FIGS. 3, 7, and 8).

FIG. 6 illustrates a front view of an injector case 64 secured to a phone case 60. The phone case 60 includes a back section for receiving a mobile device (not shown). The injector case 64 including a first injector case section 64A and a second injector case section 64B is secured to a front section of the phone case 60 (i.e., a surface opposing the back section). A release latch 66 is located on the first injector case section 64A. The first injector case section 64A and the second injector case section 64B may be separated from one another, revealing an injector located therein (see FIGS. 1-4). Movement of the release latch 66 may determine whether the first injector case section 64A and the second injector case section 64B are in a disconnected position, a connected position encapsulating the injector (as shown), or both. The injector 10 further includes a stopper 40, whereby a user may remove the stopper 40 to allow activation of the injector 10 (see FIGS. 3, 7, and 8).

Figure 7:
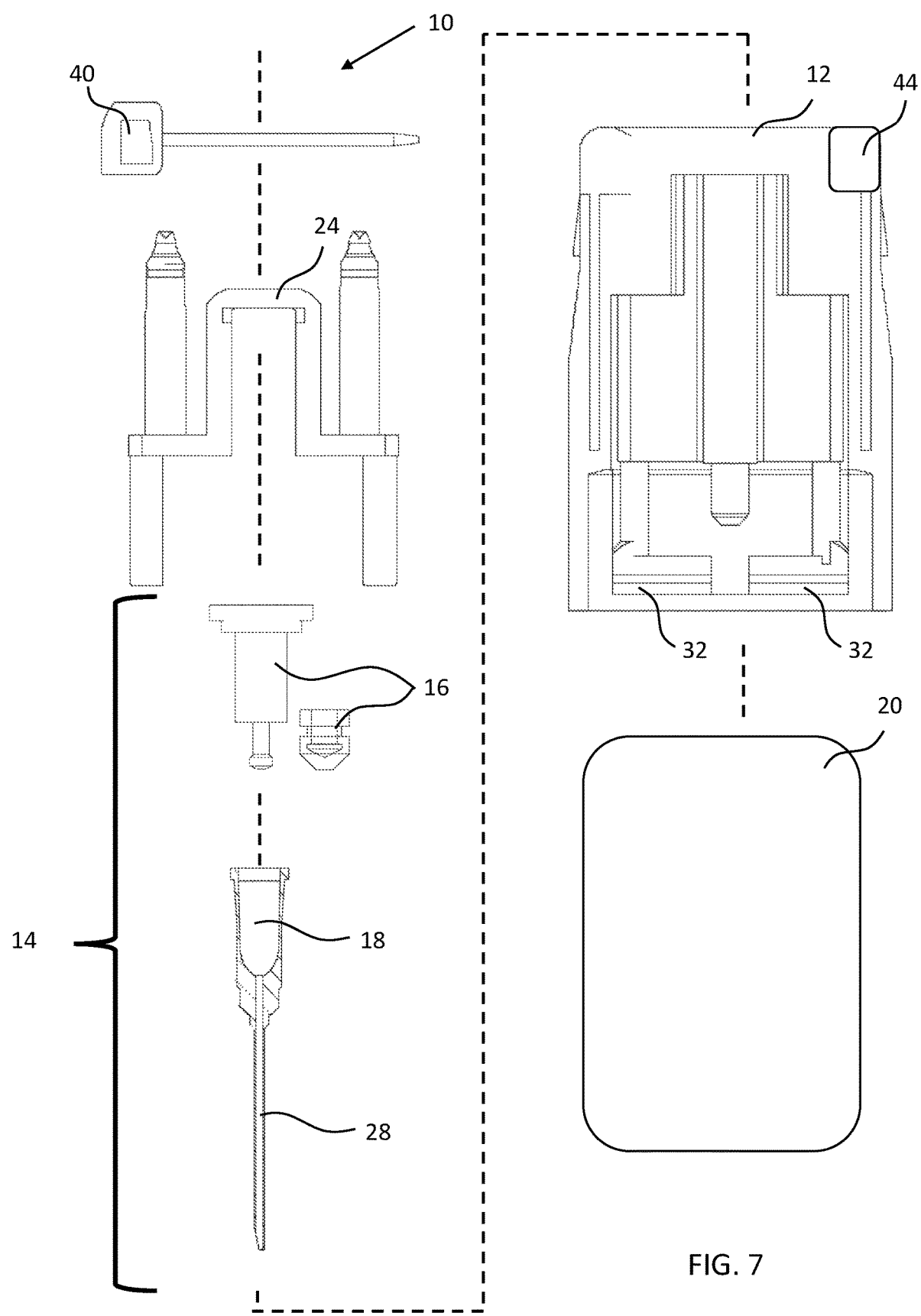
FIG. 7 is an exploded view of an injector.

FIG. 7 is an exploded view of an injector 10. The injector 10 includes a syringe 14 secured within a housing 12 having a cover 20. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 of the injector 10 is removed to allow activation of a button 44 located on the housing 12 of the injector 10. As shown, the stopper 40 may be a removable member, such as a pin. After the stopper 40 is removed, a force is applied to the button, which in turn releases a control 24 and drives the syringe 14 via a pair of biasing members to expose the needle 28 and contact a skin surface of the user (see FIGS. 8A and 8B). The syringe 14 is driven until the syringe 14 contacts an inner surface of the housing 12 that prevents further movement of the syringe 14. Once the syringe 14 abuts the inner surface of the housing 12, the control 24 drives the plunger 16 into contact with the medication 18 so that the medication 18 is distributed into the needle 28 and then into the user. After injection, the injector 10 is removed from the skin surface so that a sheath 32 moves to enclose the exposed needle 28. It should be noted that the sheath 32 may include one or more articulated pieces that move one or more additional biasing members to encapsulate the exposed needle 28.

Figure 8A:
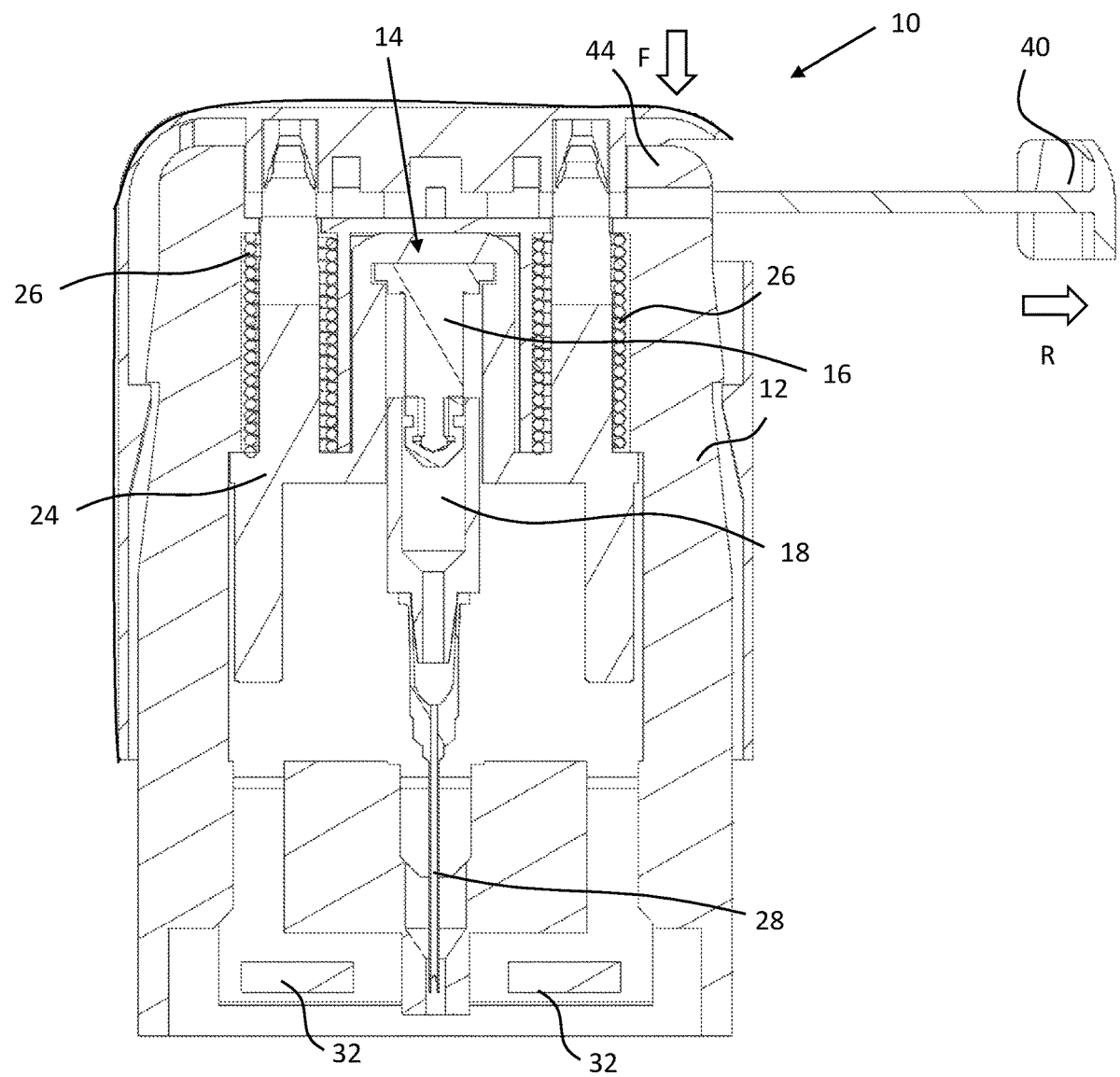
FIG. 8A is a cross-sectional view of an injector in a resting position prior to activation.
Figure 8B:
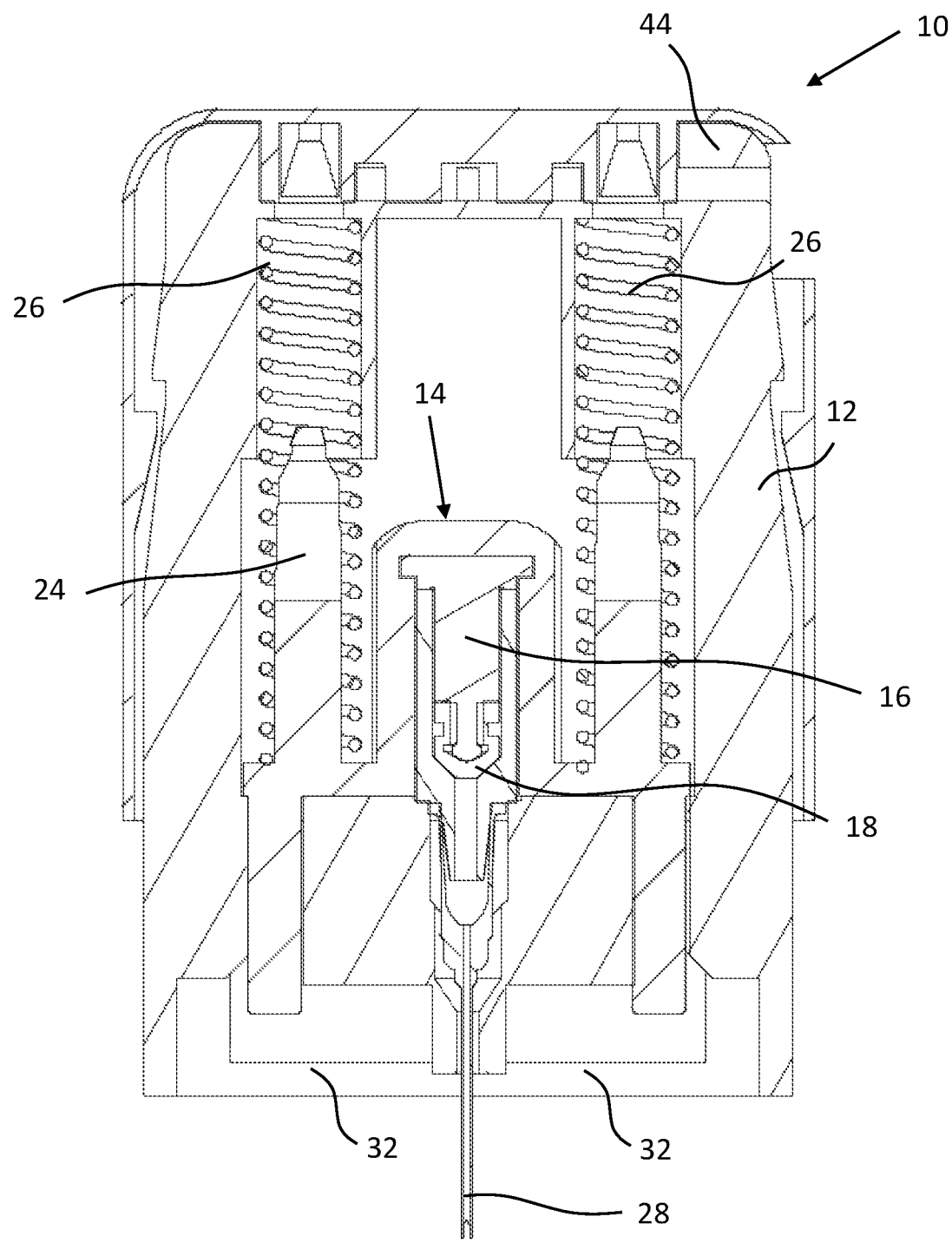
FIG. 8B is a cross-sectional view of the injector of FIG. 8A during injection.

FIGS. 8A and 8B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 of the injector 10 is removed in a direction (R) to allow activation of a button 44 located on the housing 12 of the injector 10. After the stopper 40 is removed, a force (F) is applied to the button 44, which in turn releases a control 24 and drives the syringe 14 via a pair of biasing members 26 to expose the needle 28 and contact the skin surface of the user. The syringe 14 is driven until the syringe 14 contacts an inner surface of the housing 12 that prevents further movement of the syringe 14. Once the syringe 14 abuts the inner surface of the housing 12, the control 24 drives the plunger 16 into contact with the medication 18 so that the medication 18 is distributed into the needle 28 and then into the user. After injection, the injector 10 is removed from the skin surface so that a sheath 32 moves to enclose the exposed needle 28. It should be noted that the sheath 32 may include one or more articulated pieces that move one or more additional biasing members to encapsulate the exposed needle 28.

Figure 9A:
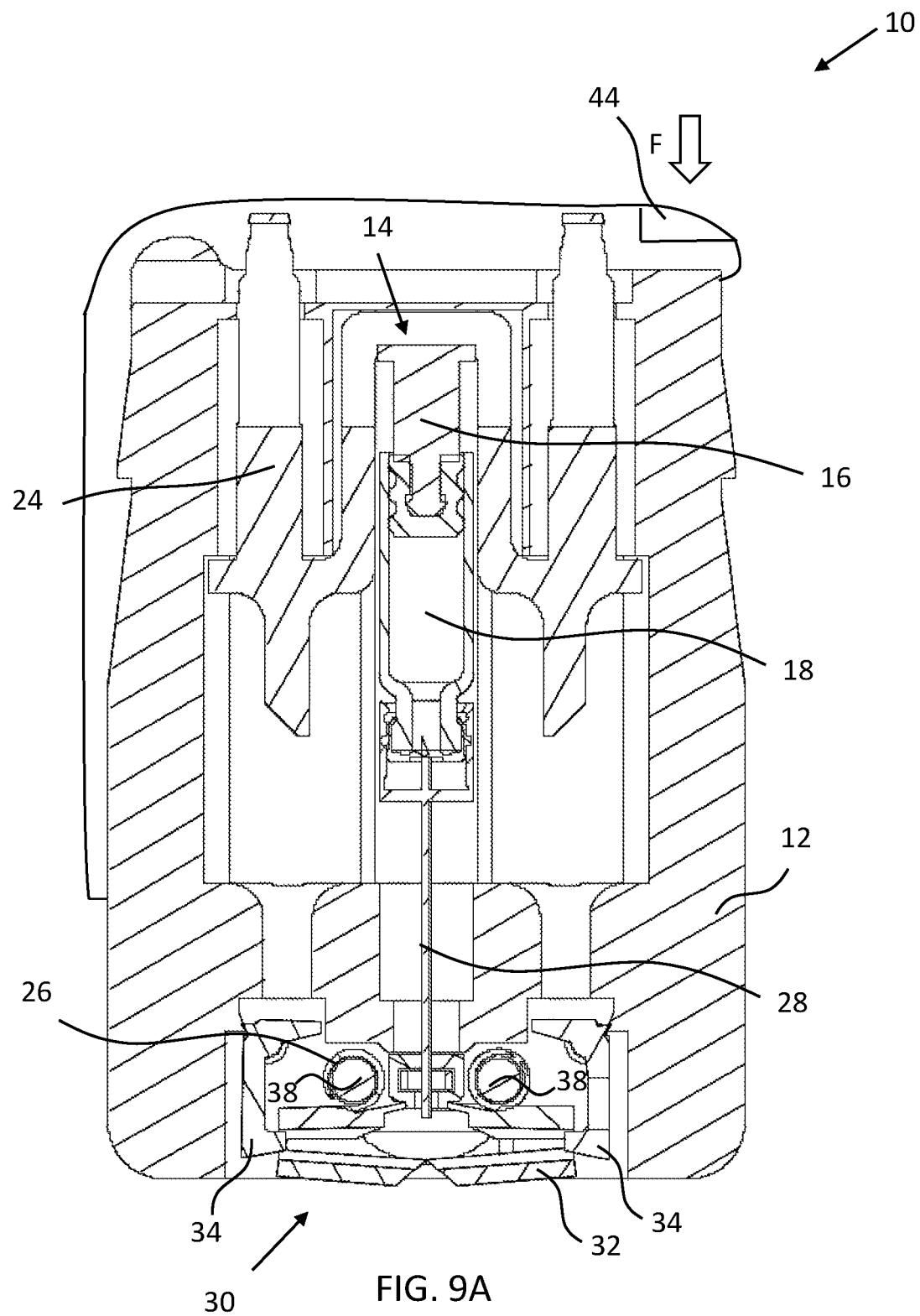
FIG. 9A is a cross-sectional view of an injector in a resting position prior to activation.
Figure 9B:
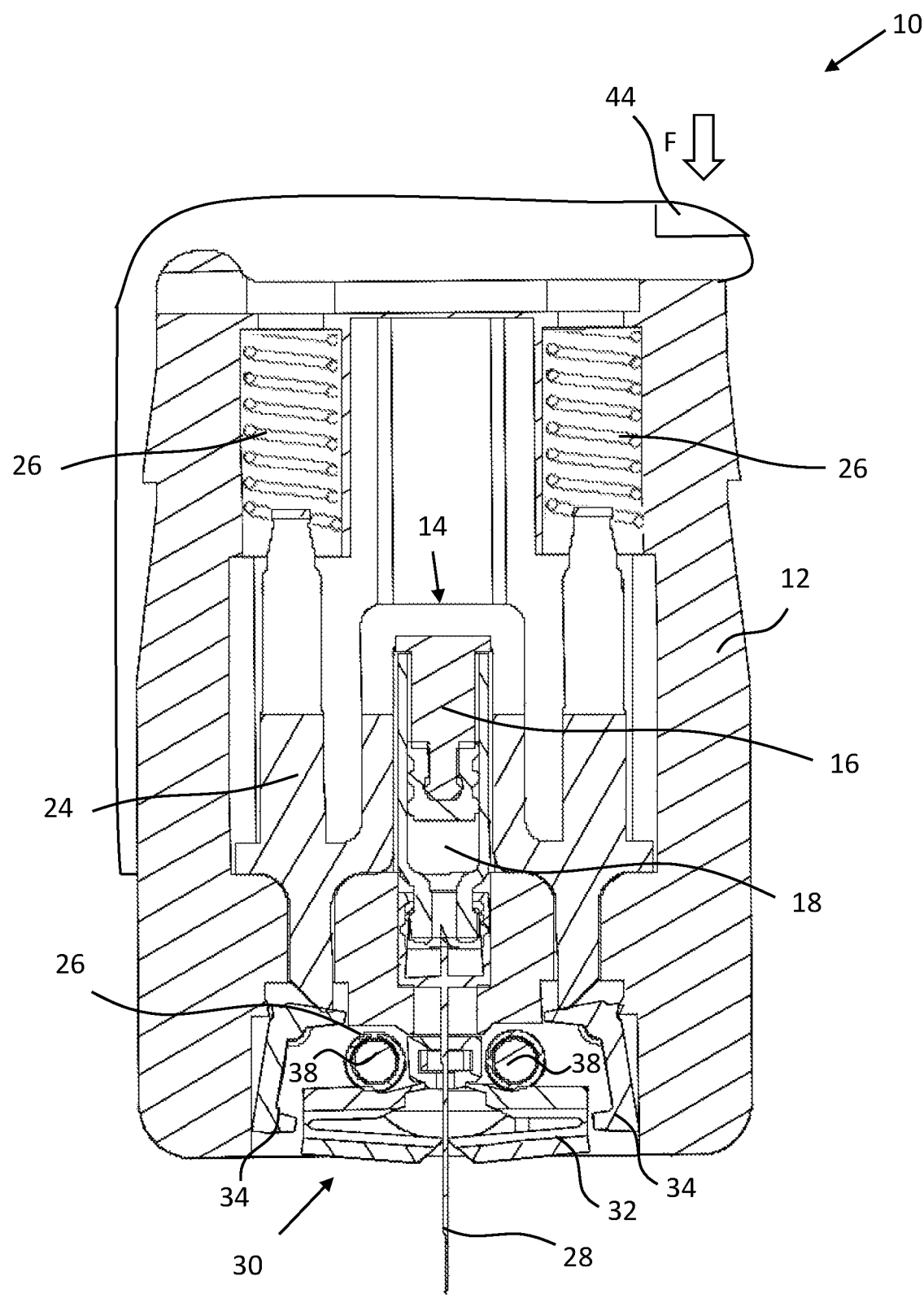
FIG. 9B is a cross-sectional view of the injector of FIG. 9A during injection.

FIGS. 9A and 9B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user. After positioning of the injector 10, a force (F) is applied to a button 44, which in turn releases a control 24 and drives the syringe 14 via a pair of biasing members 26 to expose the needle 28 and contact the skin surface of the user. The syringe 14 is driven until the syringe 14 contacts an inner surface of the housing 12 that prevents further movement of the syringe 14. Once the syringe 14 abuts the inner surface of the housing 12, the control 24 drives the plunger 16 into contact with the medication 18 so that the medication 18 is distributed into the needle 28 and then into the user. Additionally, as the control 24 drives the plunger 16, the control 24 also releases a plurality of fingers 34 of a sheath assembly 30.

Figure 9C:
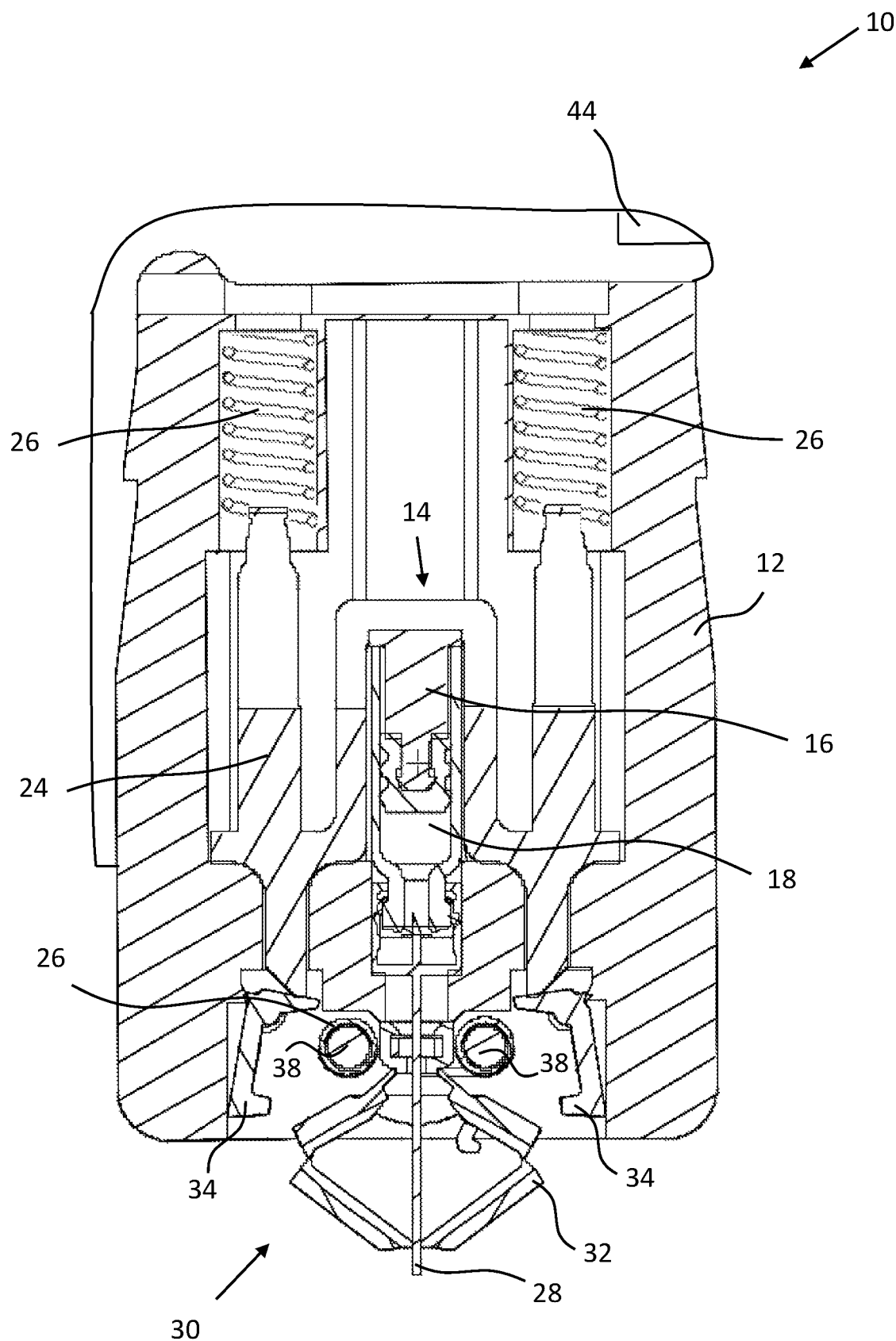
FIG. 9C is a cross-sectional view of the injector of FIG. 9A after injection with the sheath assembly partially articulated.
Figure 9D:
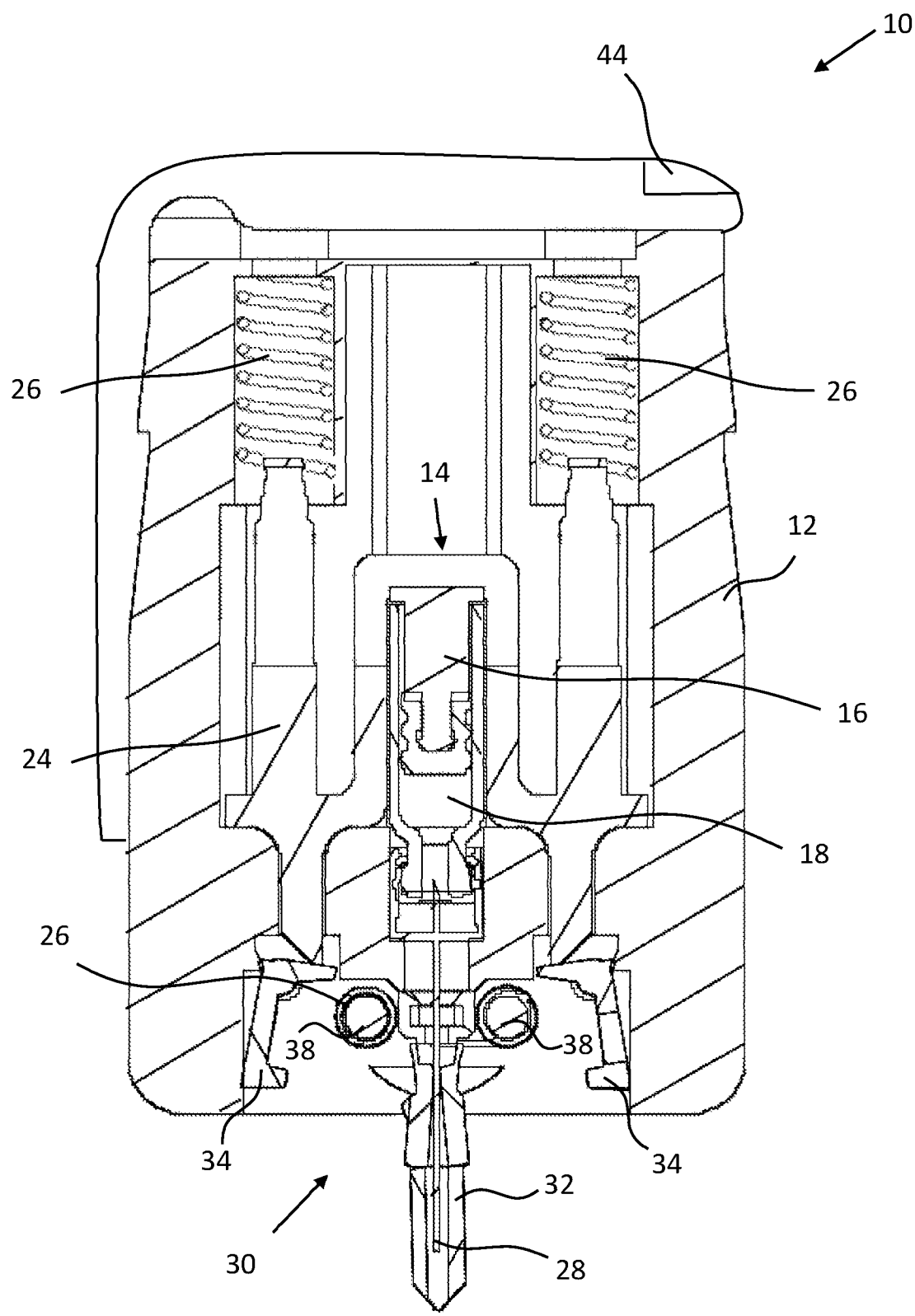
FIG. 9D is a cross-sectional view of the injector of FIG. 9A after injection with the sheath assembly fully articulated.

After injection, as illustrated in FIGS. 9C and 9D, the injector 10 is removed from the skin surface so that a sheath 32 of the sheath assembly 30 articulates to enclose the exposed needle 28. As shown in FIG. 9C, the sheath 32 is biased by a biasing member 26 secured on a plurality of projections 38 so that, when the fingers 34 are released and disengage the sheath 32, the sheath 32 begins to extend and unfold to cover the exposed needle 28. As shown in FIG. 9D, once the sheath 32 fully extends and unfolds, the needle 28 is no longer exposed and is fully encapsulated within the sheath 32.

Figure 10:
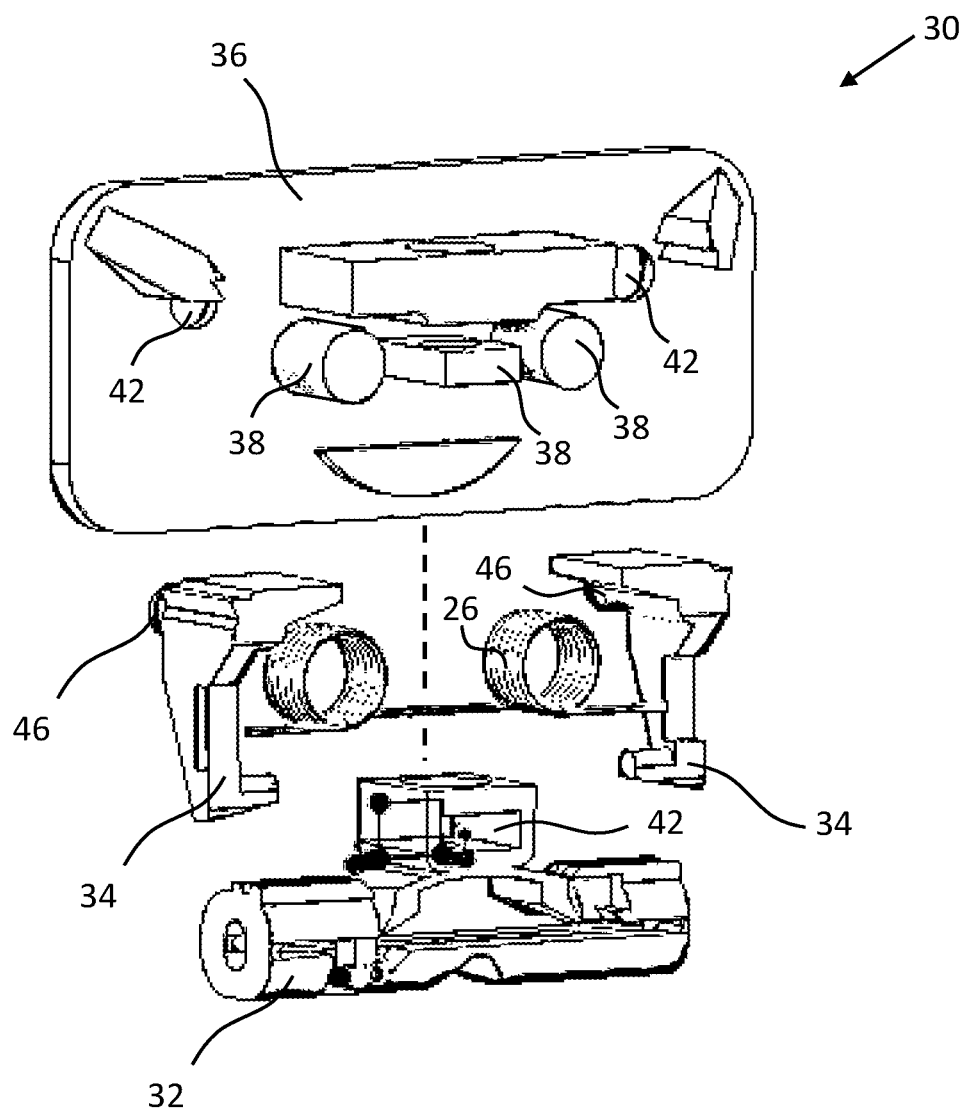
FIG. 10 is an exploded view of a sheath assembly.

FIG. 10 illustrates an exploded view of a sheath assembly 30. The sheath assembly includes a plate 36 having a plurality of projections 38 and a plurality of holes 42. As illustrated, a biasing member 26 is secured to a pair of the projections 38 substantially cylindrically shaped. A pair of opposing fingers 34 each include an engaging feature 46 that is inserted into one of the holes 42 of the plate 36 so that the fingers 34 may rotate relative to the plate 36 when engaged by a control of an injector to articulate between an engagement position where the fingers 34 are engaged to a sheath 32, and a release position where the fingers 34 are disengaged from the sheath 32 (see FIGS. 9A-9D). A hole 42 of the sheath 32 is secured to the projection 38 substantially rectangularly shaped and attached to the biasing member 26 so that, when the fingers 34 release the sheath 32, the sheath 32 articulates to unfold and extend around a needle of the injector (see FIGS. 9A-9D).

Figure 11A:
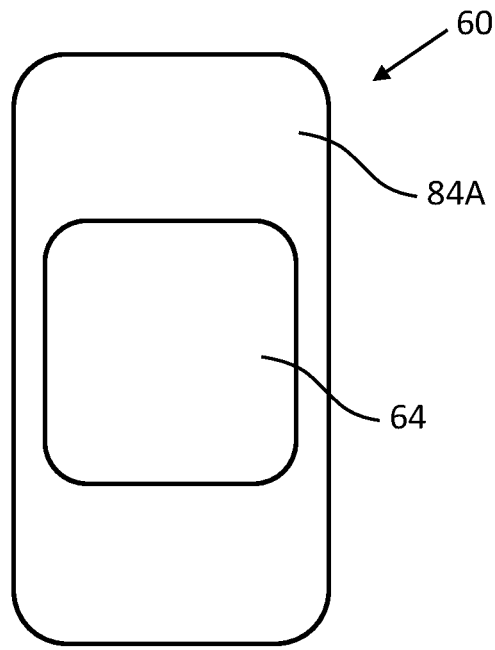
FIG. 11A is a front view of a phone case having a near-field communication sensor arrangement.
Figure 11B:
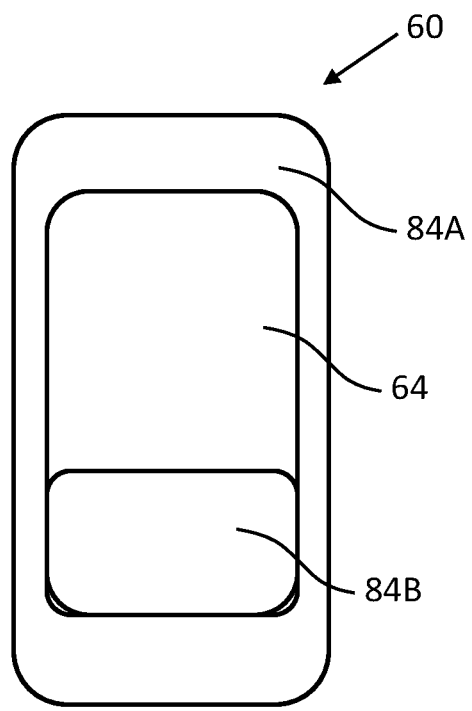
FIG. 11B is a front view of a phone case having a near-field communication sensor and temperature sensor arrangement.
Figure 11C:
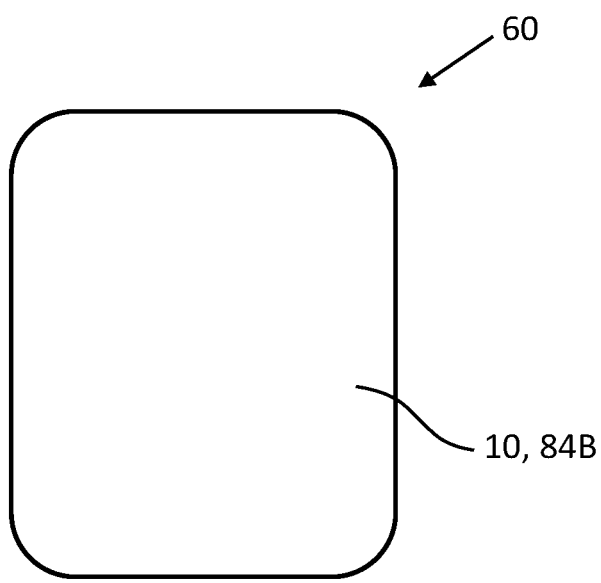
FIG. 11C is a front view of an injector having a temperature sensor arrangement.

FIGS. 11A, 11B and 11C illustrate phone cases 60 including one or more sensors 84. As shown in FIG. 11A, the phone case 60 includes an injector case 64 secured to the phone case 60. The phone case 60 includes a near-field communication reader (e.g., NFC sensor) 84A in communication with an injector 10 located within the injector case 60. As shown in FIG. 11B, the phone case 60 may also include a temperature sensor 84B located within the injector case 60 that monitors that temperature of the injector. It should also be noted, as illustrated in FIG. 11C, the temperature sensor 84B may secured within the injector 10 and secured in the injector case 64 along with the injector 16. It should be noted that the sensors 84 may monitor the injector 16, medication within the injector 16, or both. Such monitoring may monitoring the location of the injector 10 and/or medication, monitoring the temperature of the injector 16 and/or medication, or both. One or more of the sensors 84 may act as a tag and be located onto the injector 10. Upon locating the injector 10 into the injector case 64, the a mobile phone (not shown) secured within the phone case 60 may then read the tag. Upon reading the tag, one or more of the location of the injector 10, the temperature of the injector 10, or the presence of the injector 10 with the mobile phone may be monitored. If the temperature reading is outside an acceptable range, the mobile phone may display a notification that is visible to a user. The mobile phone may utilize near-field communication to monitor a proximity of the injector 10 to the phone. Such proximity may be used by the user to verify that the injector 10 is still secured with the mobile phone. Such proximity may be utilized to determine if and when the injector 10 has been utilized by the user and notifications of such use may be distributed to pre-determined devices including the user and/or the user's circle of care (i.e., those predetermined individuals designated to receive such notifications). The monitored temperature of the injector 10 may be utilized to determine the proximity of the injector 10 to the mobile phone. A plurality of sensors 84 may be utilized to determine real-time temperature of the injector 10. It should be noted that while an injector 10 has been discussed herein regarding FIGS. 11A-11C, the injector 10 may be any medical device.

FIGS. 12A-12C illustrate a side view of an injector 10. The injector 10 includes a syringe 14 secured within a housing 12. The syringe 14 is positioned between a movable first platform 70 and a movable second platform 72. The syringe 14 includes a plunger 16 configured to distribute a medication 18 into a needle 28 of the syringe 14 to administer to a user. To inject the medication 18 into a user, the injector 10 is positioned on a skin surface of the user and a force (F) is applied to a control 24 of the injector 10 to move the syringe 14. As shown in FIG. 12A, the injector 10 is in a resting position prior to injection. As shown in FIG. 12B, after the force (F) is applied to the control 24, the control 24 releases engagement of a pair of syringe engaging mechanisms 68A protruding from the first platform 70. As the syringe engaging mechanisms 68A are released, a first biasing member 26A moves the syringe 14 so that the plunger 16 is substantially axially positioned with an axis of a second biasing member 26B and the needle 28 extends outside of the housing 12 to contact a user. Once the plunger 16 and the second biasing member 26B are aligned, the second biasing member 26B is released to push the plunger 16 into the medication 18 so that the medication 18 is distributed into the needle 28 and then into the user. During engagement, a pair of protrusions 74 of the second platform 72 contact a pair of sheath engaging mechanisms 68B of a sheath 32 so the sheath 32 is released from the housing 12. After injection as shown in FIG. 12C, the injector 10 is removed from the skin surface so that a pair of biasing members 26 extends the sheath 32 to enclose the needle 28.

Figures 13, 14A, 14B:
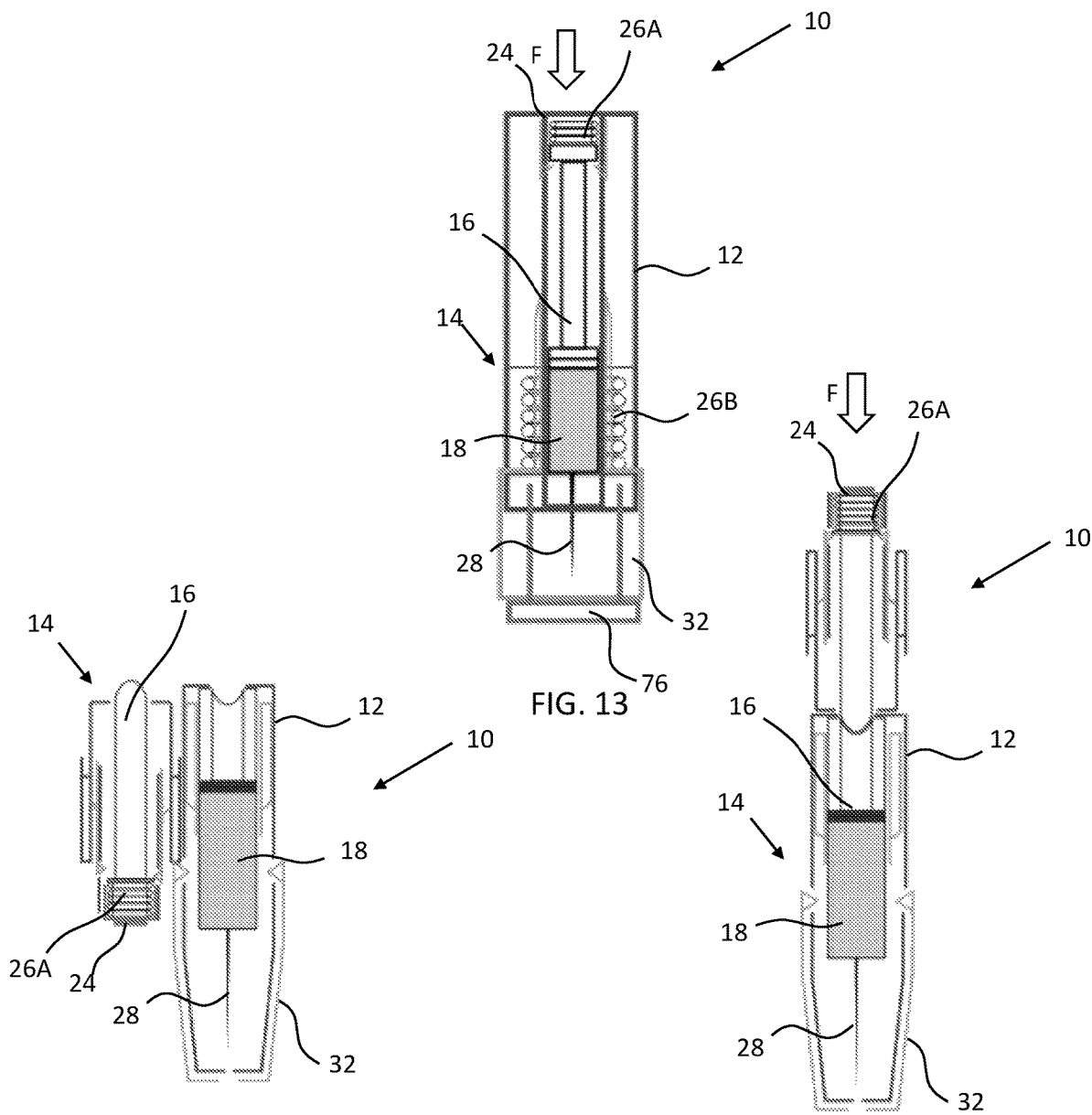
FIG. 13 is a side view of an injector.
FIG. 14A is a side view of an injector.
FIG. 14B is a side view of an injector.

FIG. 13 illustrates a side view of an injector 10. The injector 10 includes a syringe 14 enclosed in a housing 12. The syringe 14 include a plunger 16 movably opposing a medication 18 encapsulated in the syringe 14. The injector 10 is configured so that a user may remove a cap 76 of the injector 10 and expose a needle 28 of the syringe 14 for injection. To inject, the needle 28 is inserted into a user's skin and a force (F) is applied to a control 24 of the injector 10 so that a first biasing member 26A drives the plunger 16 to push the medication 18 through the needle 28 and into the user. The injector 10 also includes a movable sheath 32 that is biased relative to the housing 12 via a second biasing member 26B. The sheath 32 is configured to compress the second biasing member 26B during injector so that, once injection is completed, the second biasing member 26B extends the sheath 32 back to an original position to encapsulate the needle 28 and prevent accidental contact with the needle 28.

FIGS. 14A and 14B illustrate a side view of an injector 10 having a removable plunger 16. A syringe 14 is secured within a housing 12 of the injector 12. During injection, the plunger 16 is moved to abut the housing 12 of the injector 10 and align the plunger 16 with a medication 18 of the syringe 14. To inject, a force (F) is applied to a control 24 so that a biasing member 26 drives the plunger 16 into the medication 18 so that the medication 18 is pushed through a needle 28 and into a user. The injector 10 also includes a moveable sheath 32 to protect a user from accidentally contacting the needle 28 before injection, after injection, or both.

Figure 15A:
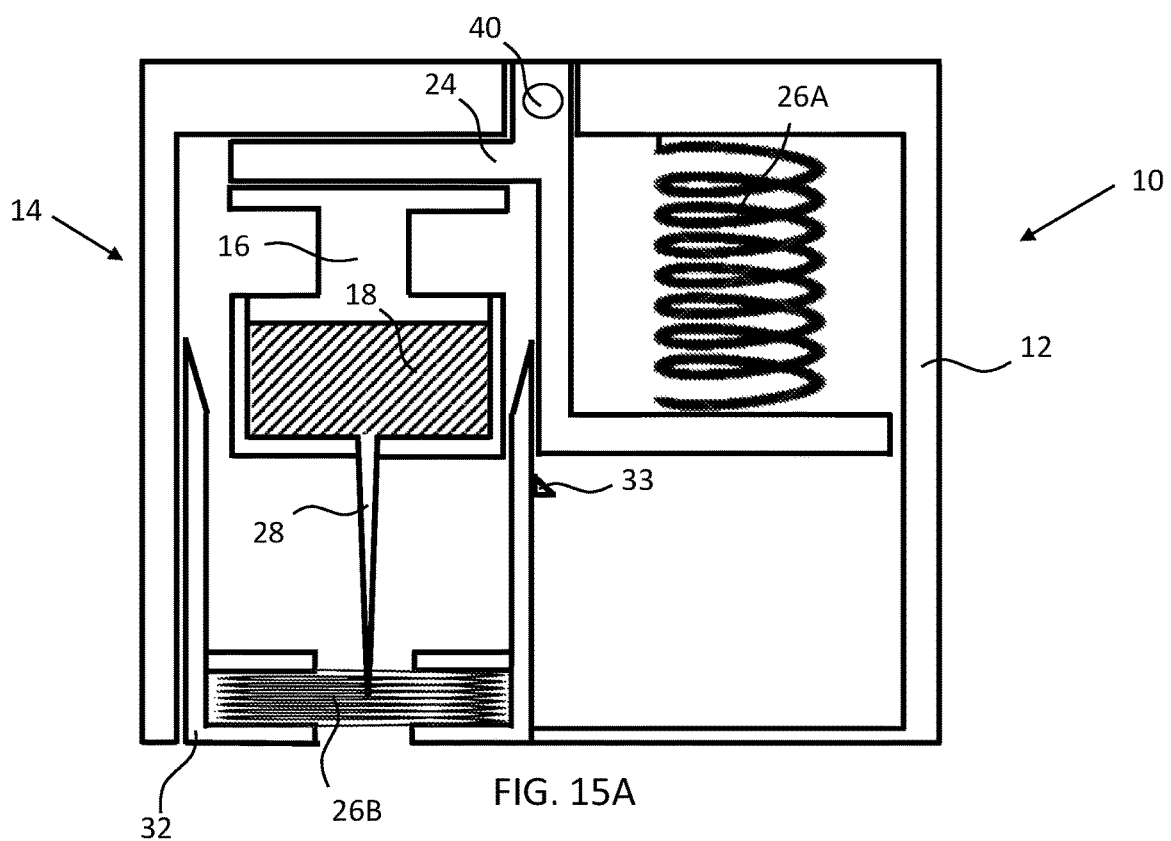
FIG. 15A is a side view of an injector in a resting position.
Figure 15B:
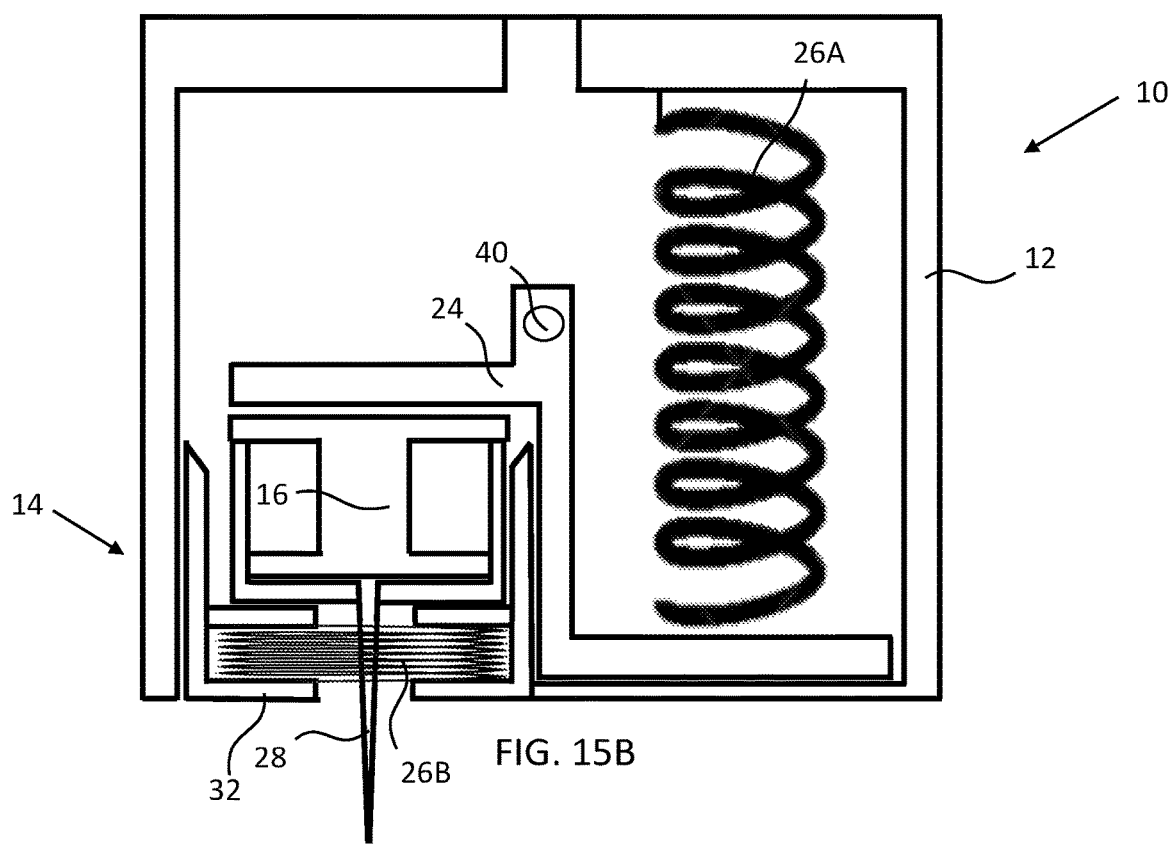
FIG. 15B is a side view of the injector of FIG. 15A in an engagement position.
Figure 15C:
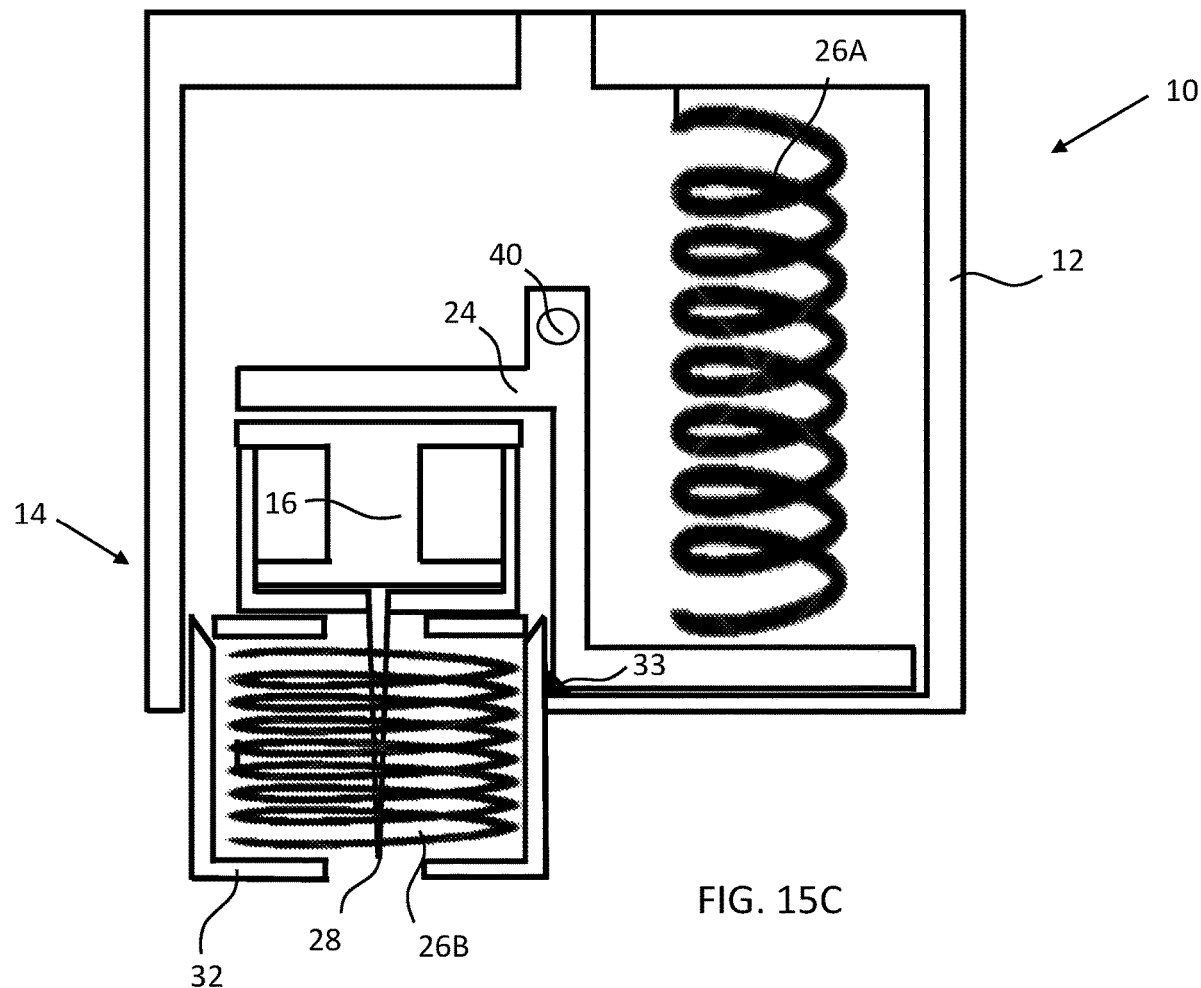
FIG. 15C is a side view of the injector of FIG. 15A in an extended position.

FIGS. 15A-15C illustrate a side view of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. As shown in FIG. 15A, the injector 10 is in a resting position prior to injection. As shown in FIG. 15B, after the stopper 40 is removed, the control 24 drives the syringe via a first biasing member 26A to expose the needle 28 and contact the skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. During engagement, the syringe 14 contacts a sheath 32 so that the sheath 32 is released from the housing 12. After injection as shown in FIG. 15C, the injector 10 is removed from the skin surface so that a second biasing member 26B extends the sheath 32 until a sheath brake 33 abuts a surface of the housing 12 and the sheath 32 encloses the needle 28.

Figure 16:
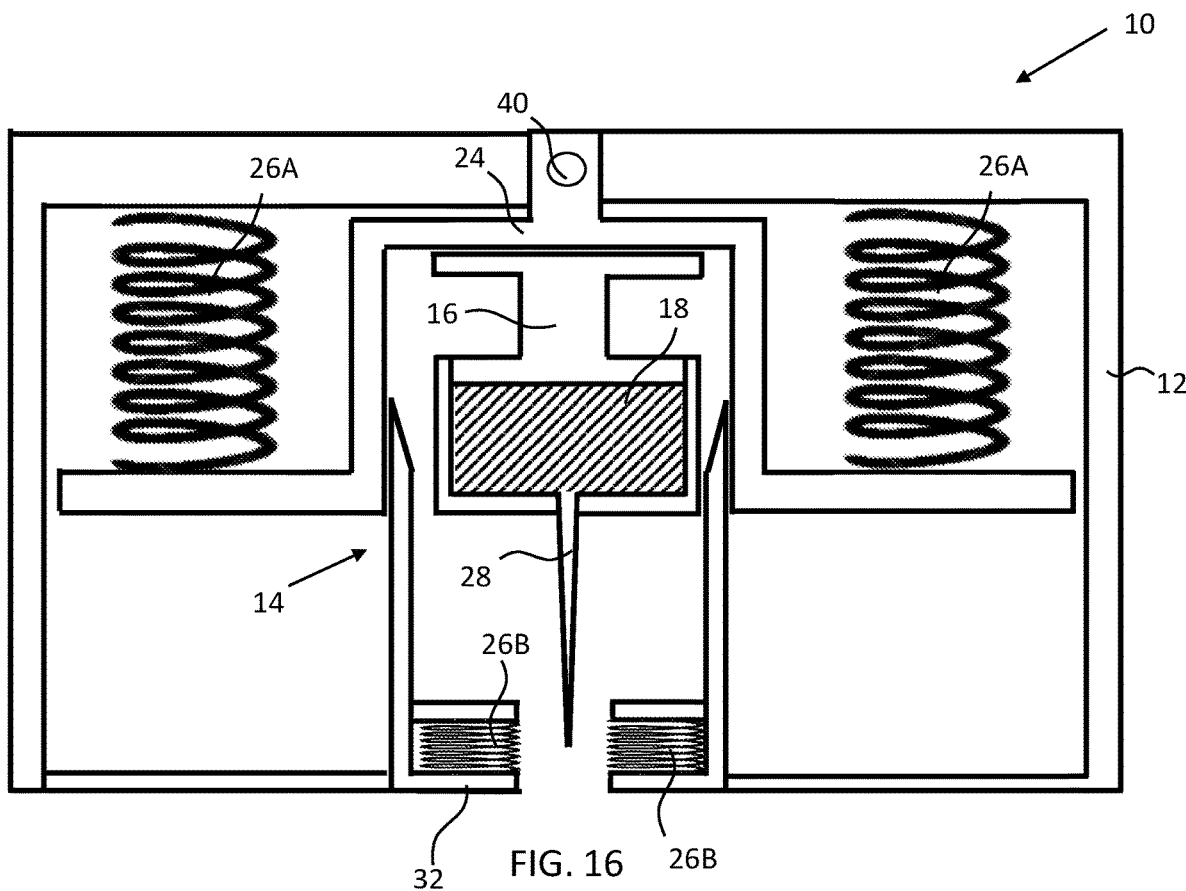
FIG. 16 is a side view of an injector in a resting position.

FIG. 16 illustrates a side view of an injector 10 in a resting position. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. After the stopper 40 is removed, the control 24 drives the syringe via a first pair of biasing members 26A to expose the needle 28 and contact a skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. During engagement, the syringe 14 contacts a sheath 32 so that the sheath 32 is released from the housing 12. After injection, the injector 10 is removed from the skin surface so that a second pair of biasing members 26B extend the sheath 32 until a sheath brake 33 abuts a surface of the housing 12 and the sheath 32 encloses the needle 28.

Figure 17A:
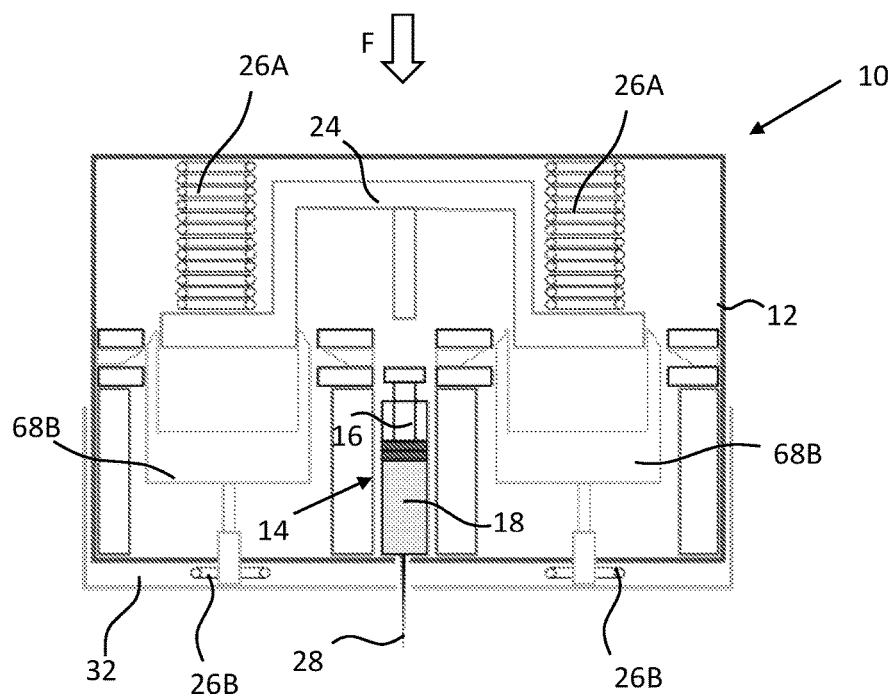
FIG. 17A is a side view of an injector in a resting position.
Figure 17B:
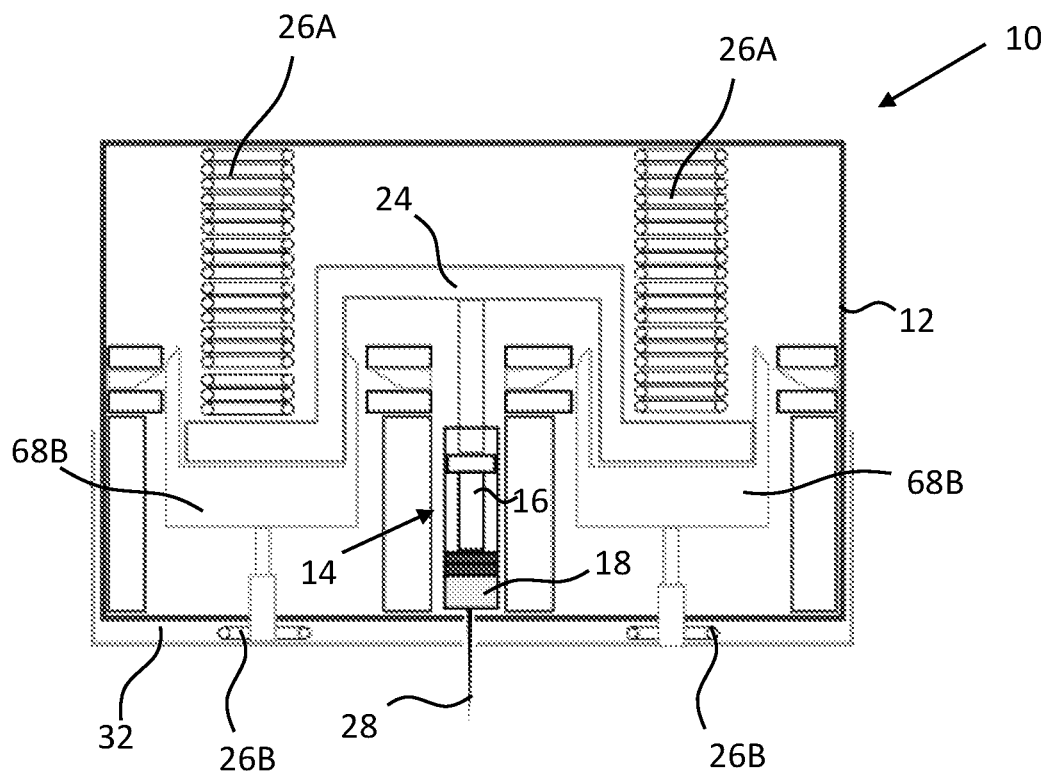
FIG. 17B is a side view of the injector of FIG. 17A in an engagement position.
Figure 17C:
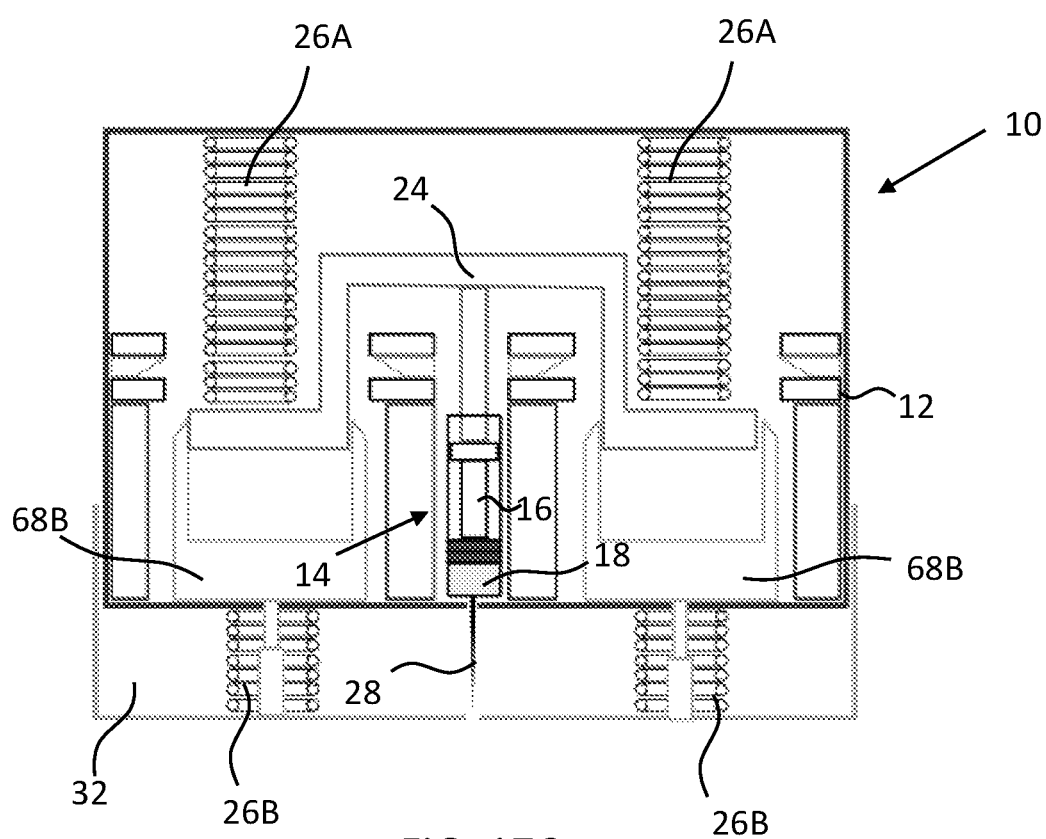
FIG. 17C is a side view of the injector of FIG. 17A in an extended position.

FIGS. 17A-17C illustrate a side view of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a force (F) is applied to a control 24 of the injector 10. After the force (F) is applied, the control 24 drives the syringe via a first pair of biasing members 26A to expose the needle 28 and contact a skin surface of the user. As shown in FIG. 17A, the injector 10 is in a resting position prior to injection. As shown in FIG. 17B, the syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. During engagement, the syringe 14 contacts and fractures sheath engaging mechanisms 68B so that the sheath 32 is released from the housing 12. After injection as shown in FIG. 17C, the injector 10 is removed from the skin surface so that a second pair of biasing members 26B extends the sheath 32 to encloses the needle 28.

Figure 18A:
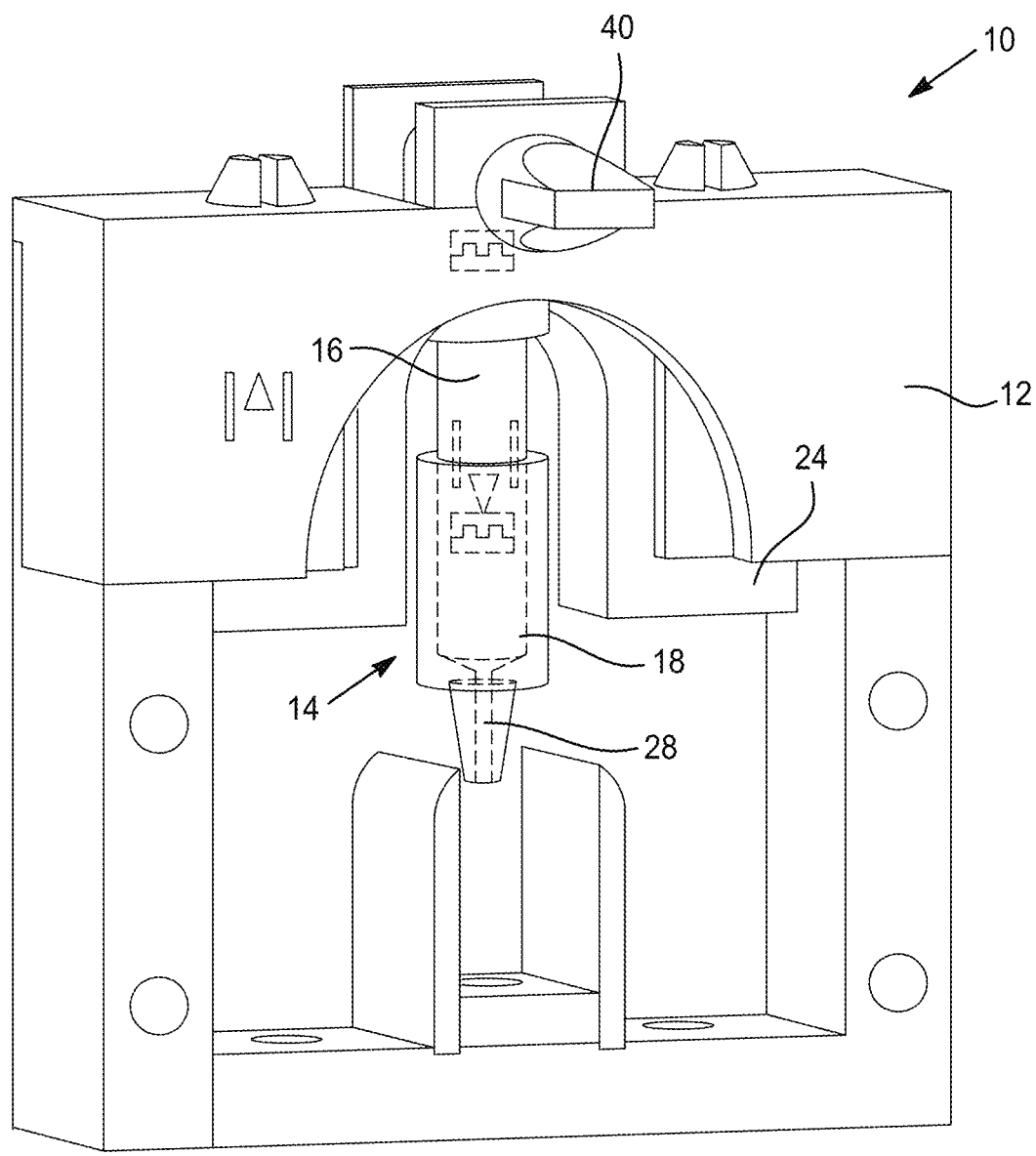
FIG. 18A is a perspective view of an injector.
Figure 18B:
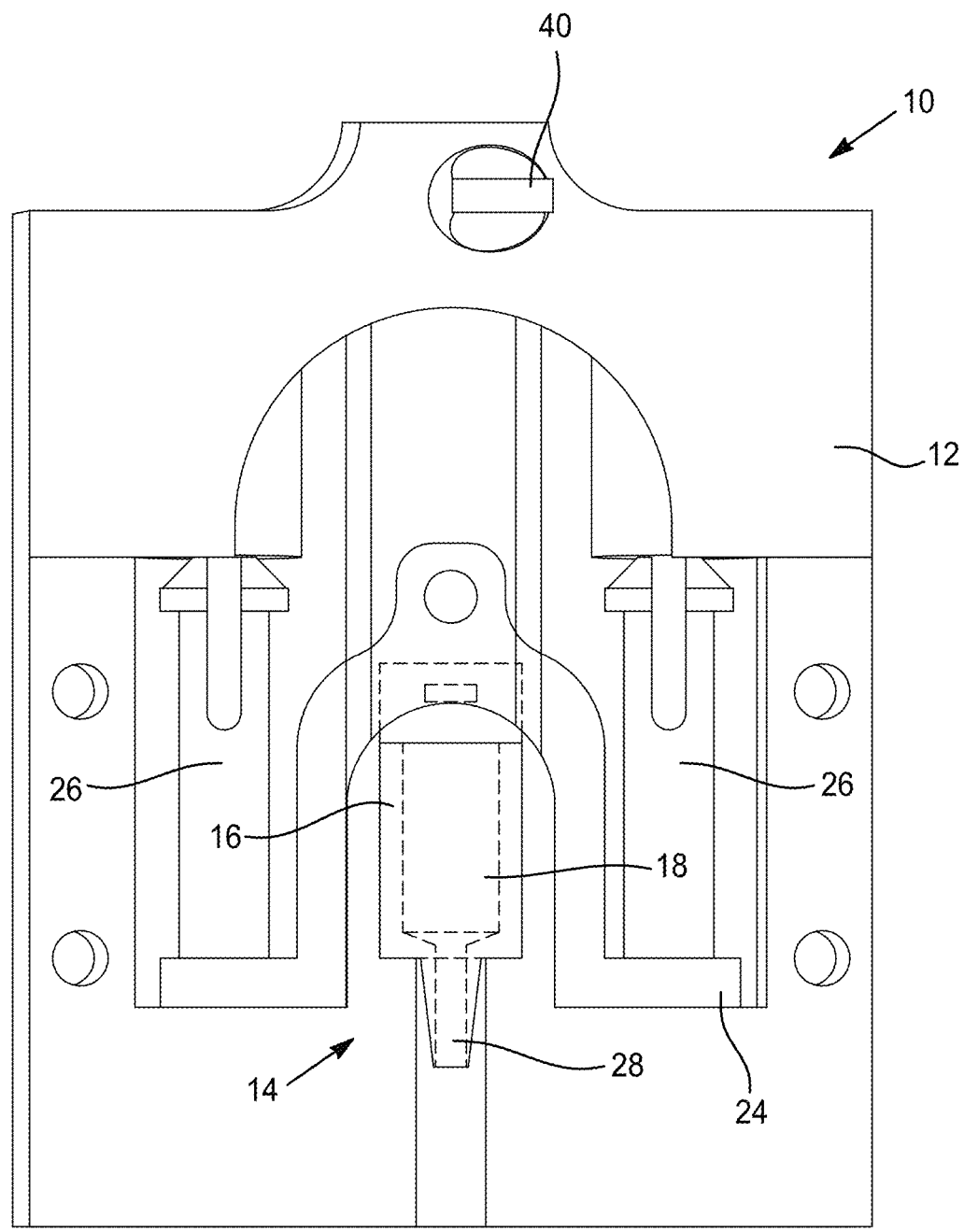
FIG. 18B is a side view of the injector of FIG. 18A.

FIGS. 18 and 18B illustrates a perspective view and a side view, respectively, of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. After the stopper 40 is removed, the control 24 drives the syringe via a pair of biasing members (not shown) to expose the needle 28 and contact a skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. After injection, the injector 10 is removed from the skin surface so that a sheath 32 encloses the needle 28 (see FIG. 16).

Figure 19:
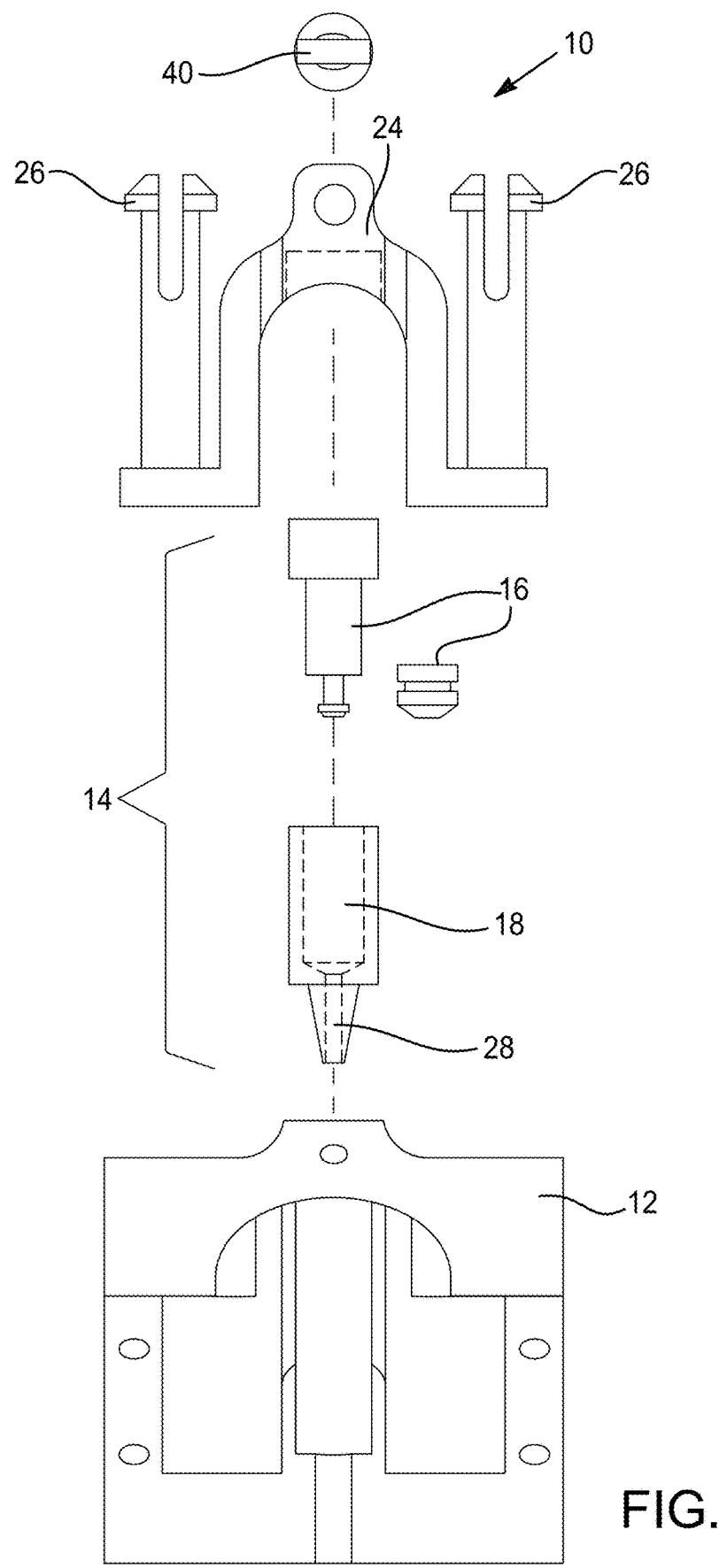
FIG. 19 is an exploded view of the injector of FIG. 18A.

FIG. 19 illustrates an exploded view of the injector 10 of FIG. 18. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. After the stopper 40 is removed, the control 24 drives the syringe via a pair of biasing members 26 to expose the needle 28 and contact a skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. After injection, the injector 10 is removed from the skin surface so that a sheath 32 encloses the needle 28 (see FIG. 16).

Figure 20A:
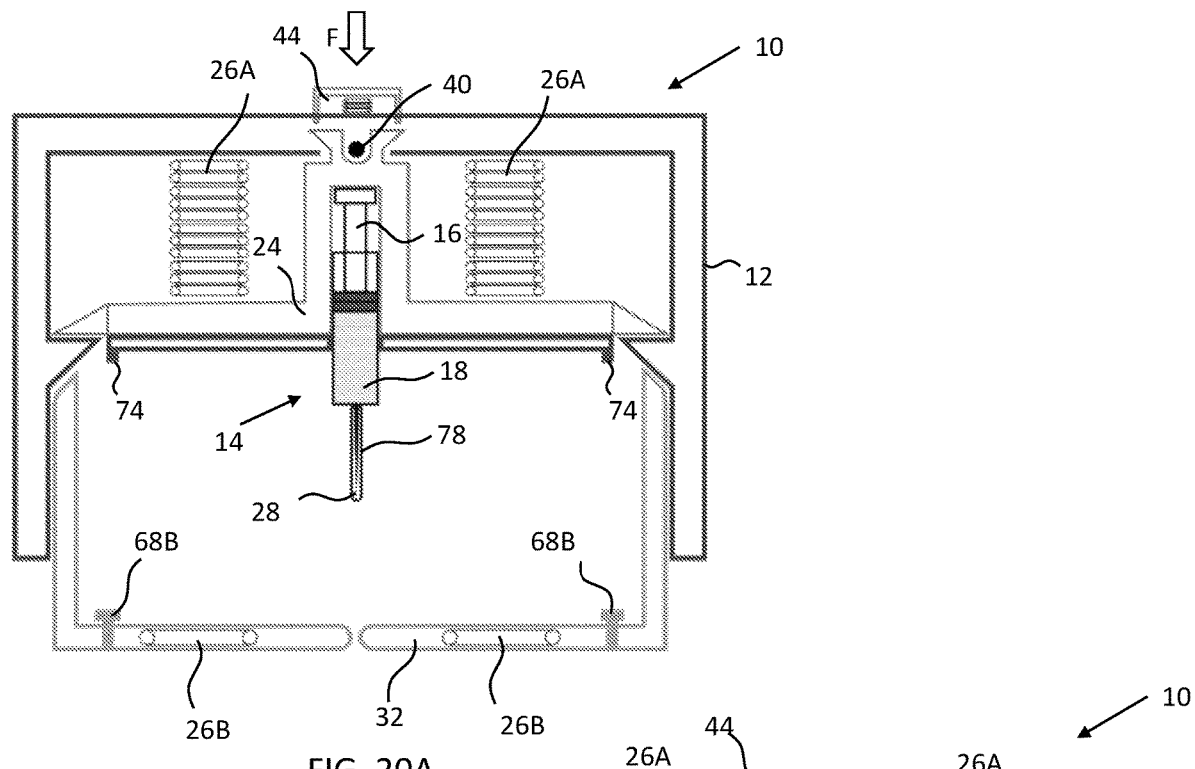
FIG. 20A is a side view of an injector in a resting position.
Figure 20B:
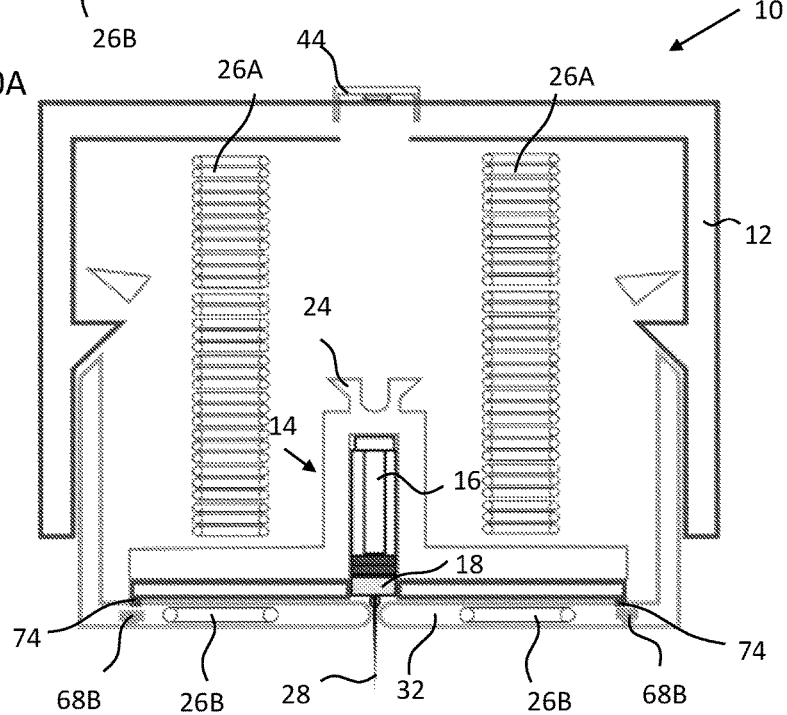
FIG. 20B is a side view of the injector of FIG. 20A in an engagement position.
Figure 20C:
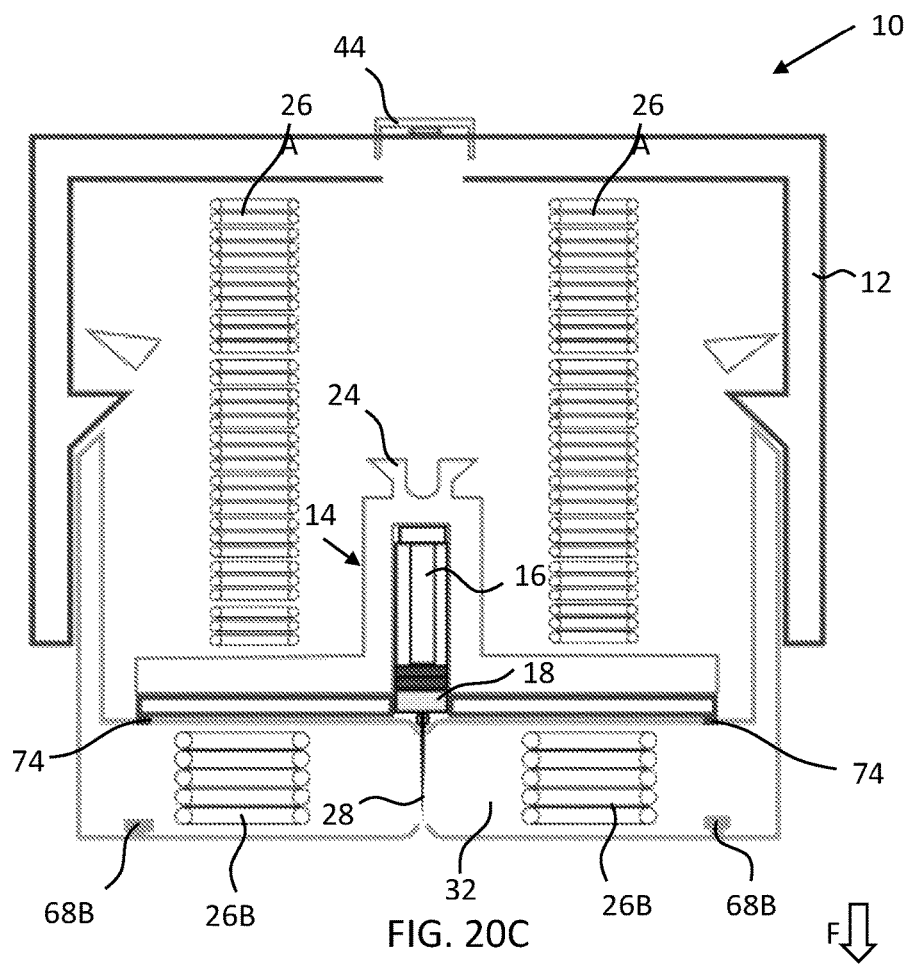
FIG. 20C is a side view of the injector of FIG. 20A in an extended position.

FIGS. 20A-20C illustrate a side view of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user, a stopper 40 is released, and a force (F) is applied to a button 44 of the injector 10. After the force (F) is applied, the button 44 releases a control 24 biased against the housing to drive the syringe 14 via a first pair of biasing members 26A to expose the needle 28 and contact a skin surface of the user. As shown in FIG. 20A, the injector 10 is in a resting position prior to injection. As shown in FIG. 20B, the syringe 14 is driven until the syringe 14 contacts a surface of the housing 12 so that the needle 28 pierces through a sterilization cover 78 and extends outside of the housing 12. Once the syringe 14 abuts the surface of the housing 12, the control 24 drives the plunger 16 into contact with the medication 18 so that the medication 18 is distributed into the needle 28 and then into the user. During engagement, protrusions 74 of the control 24 contact sheath engaging mechanisms 68B so that a sheath 32 is released from the housing 12. After injection as shown in FIG. 20C, the injector 10 is removed from the skin surface so that a second pair of biasing members 26B extends the sheath 32 to encloses the needle 28.

Figure 21:
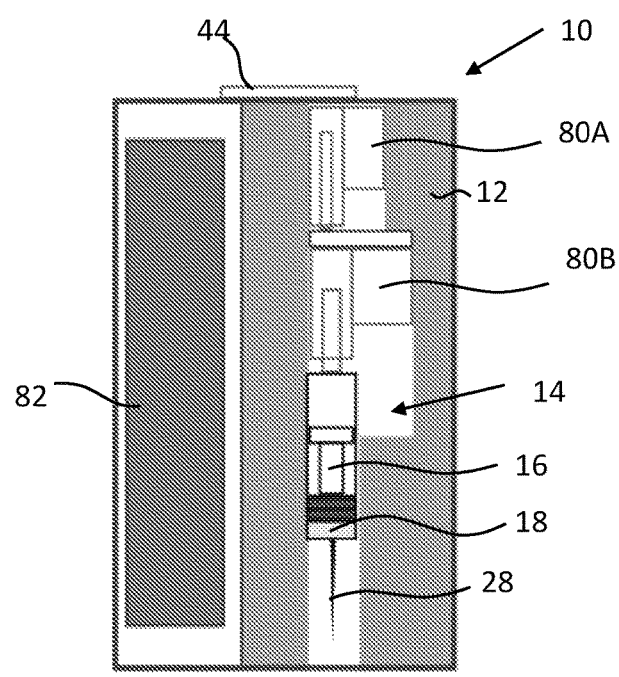
FIG. 21 is a side view of an injector.

FIG. 21 illustrates a side view of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a force (F) is applied to a button 44 located on the housing 12. The engagement of the button 44 results in a signal being sent to a controller 82 of the injector 10. The controller 80 communicates to actuate a first linear actuator 80A that drives the syringe 14 so that the needle 28 extends beyond the housing 12 and contacts the skin surface of the user. After the needle 28 contacts the skin surface, a second linear actuator 80B is actuated to drive the plunger 16 and distribute the medication 18 into the needle 28 and into the user.

Figure 22:
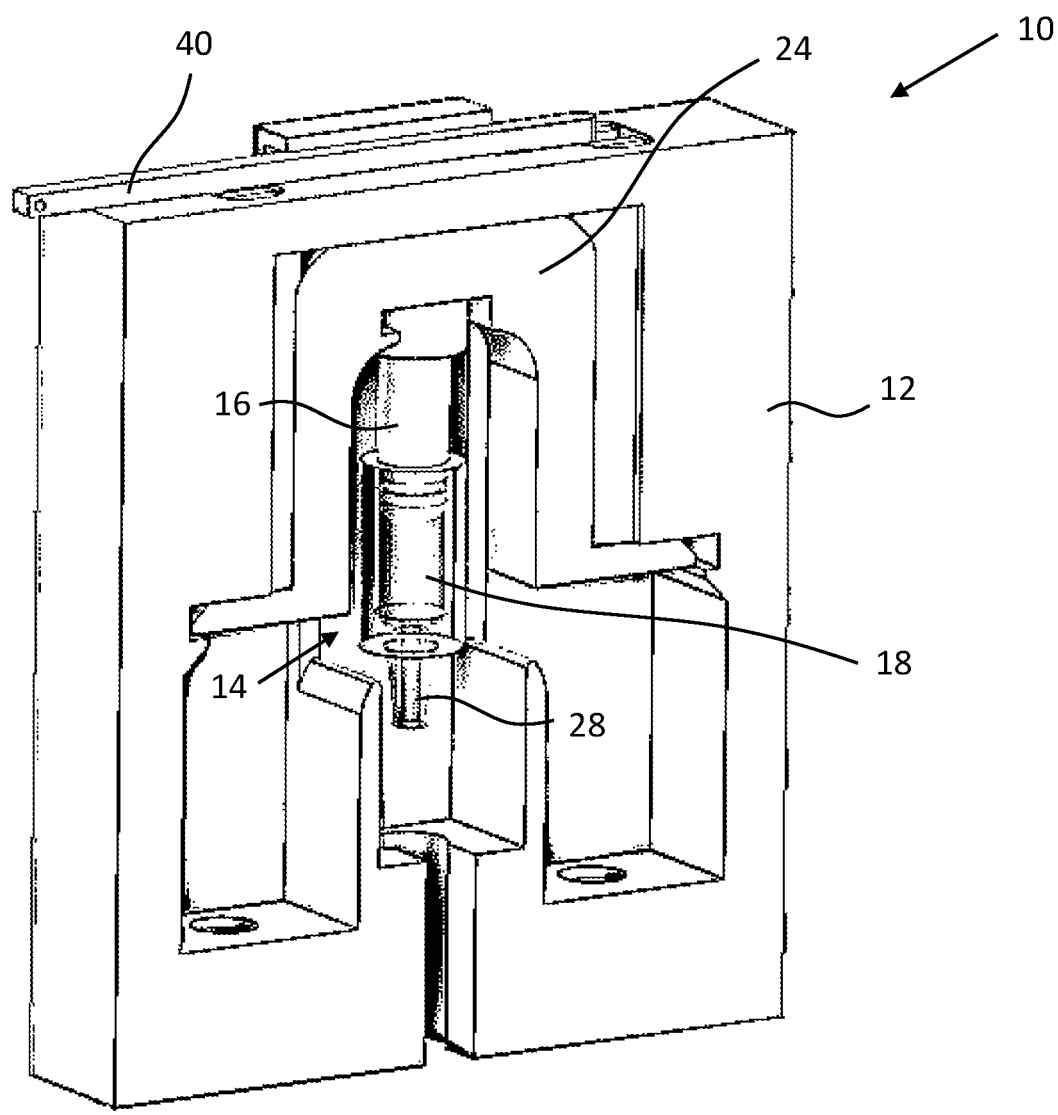
FIG. 22 is a perspective view of an injector.

FIG. 22 illustrates a perspective view of an injector 10. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. After the stopper 40 is removed, the control 24 drives the syringe via a pair of biasing members (not shown) to expose the needle 28 and contact a skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. After injection, the injector 10 is removed from the skin surface so that a sheath (not shown) encloses the needle 28 (see FIGS. 20A-20C).

Figure 23:
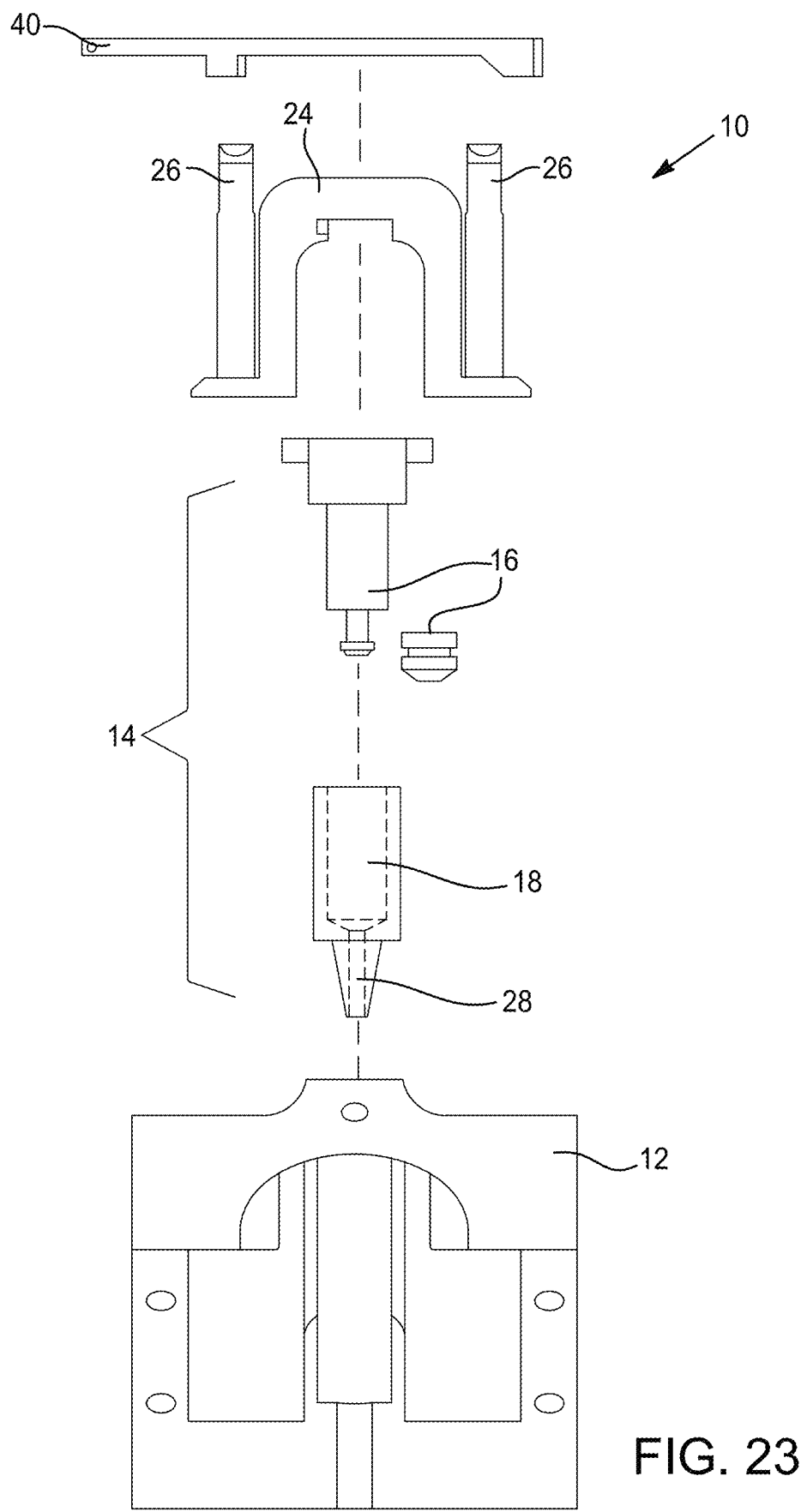
FIG. 23 is an exploded view of the injector of FIG. 22.

FIG. 23 illustrates an exploded view of the injector 10 of FIG. 7. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 securing a position of a control 24 of the injector 10 is removed. After the stopper 40 is removed, the control 24 drives the syringe via a pair of biasing members 26 to expose the needle 28 and contact a skin surface of the user. The syringe 14 is driven until the syringe 14 contacts a surface of the housing 12 that prevents further movement of the syringe 14. Once the syringe abuts the surface of the housing 12, the control 24 drives the plunger 16 into contact with the medication 18 so that the medication 18 is distributed into the needle 28 and then into the user. After injection, the injector 10 is removed from the skin surface so that a sheath 32 encloses the needle 28 (see FIGS. 20A-20C).

Figure 24:
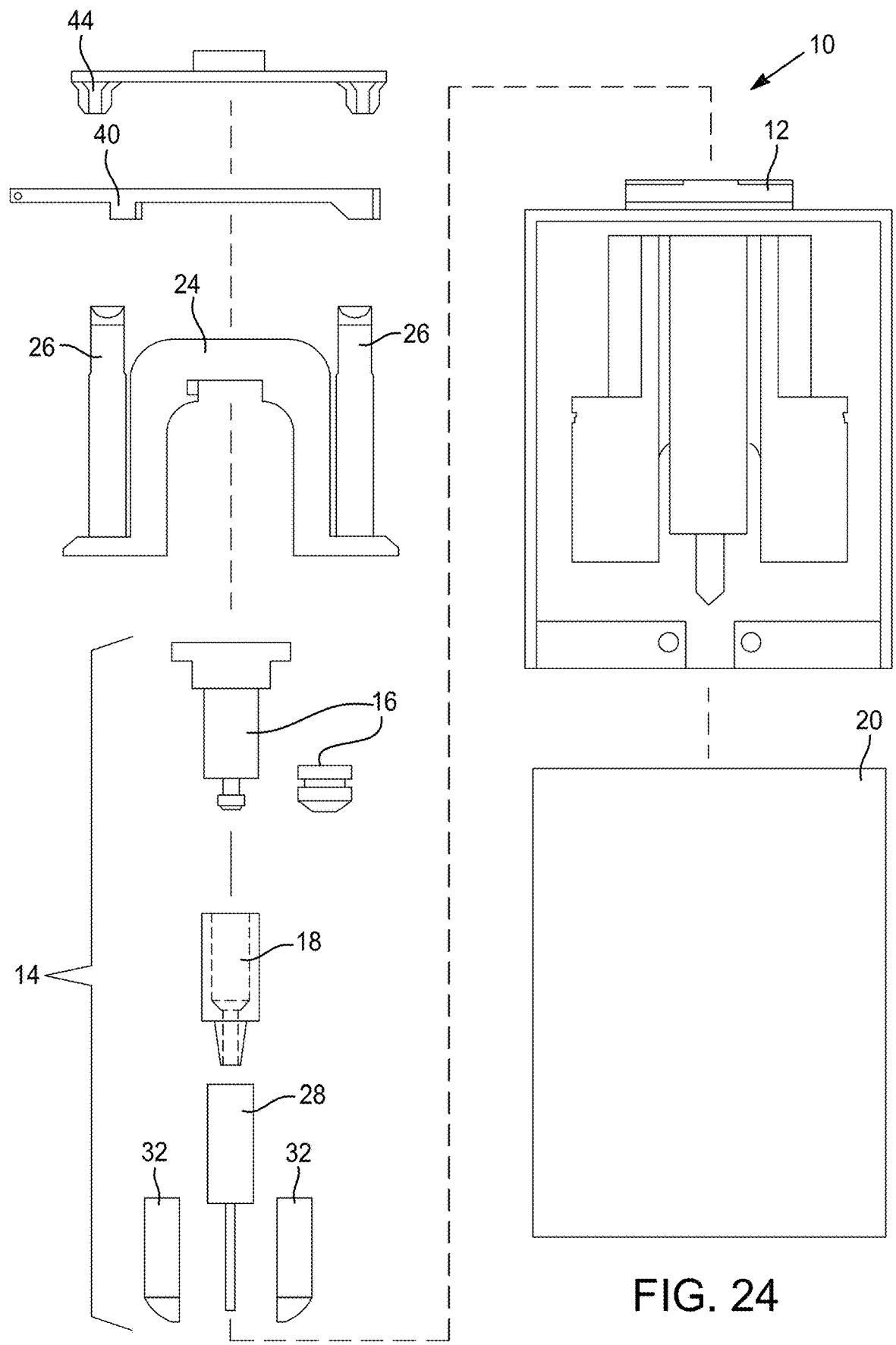
FIG. 24 is an exploded view of an injector.

FIG. 24 illustrates an exploded view of an injector 10. The injector 10 includes a syringe 14 secured within a housing 12 having a cover 20. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 of the injector 10 is removed or articulated to expose a button 44 of the injector. As shown, the stopper 40 may be a latch or slidable member. After the stopper 40 is removed, a force is applied to the button 44, which in turn releases the control 24 and drives the syringe 14 via a pair of biasing members 26 to expose the needle 28 and contact a skin surface of the user (see FIG. 20A-20C). The syringe 14 is driven until the syringe 14 contacts a surface of the housing 12 that prevents further movement of the syringe 14. Once the syringe 14 abuts the surface of the housing 12, the control 24 drives the plunger 16 into contact with the medication 18 so that the medication 18 is distributed into the needle 28 and then into the user. After injection, the injector 10 is removed from the skin surface so that a two-piece sheath 32 extends around and encloses the needle 28.

Figure 25A:
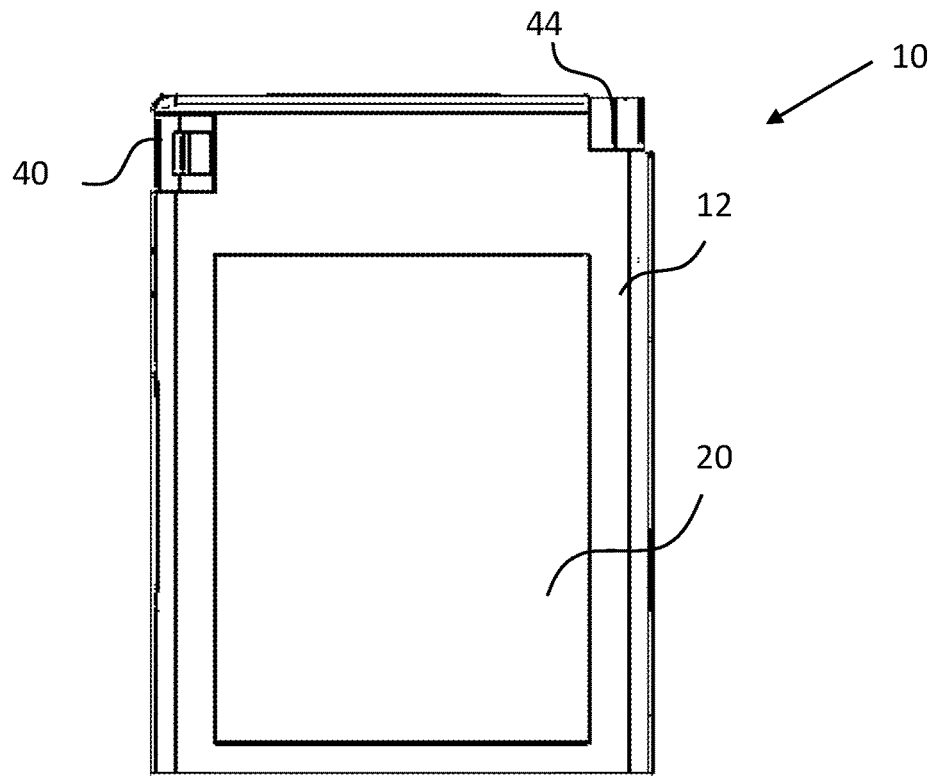
FIG. 25A is a side view of an injector.
Figure 25B:
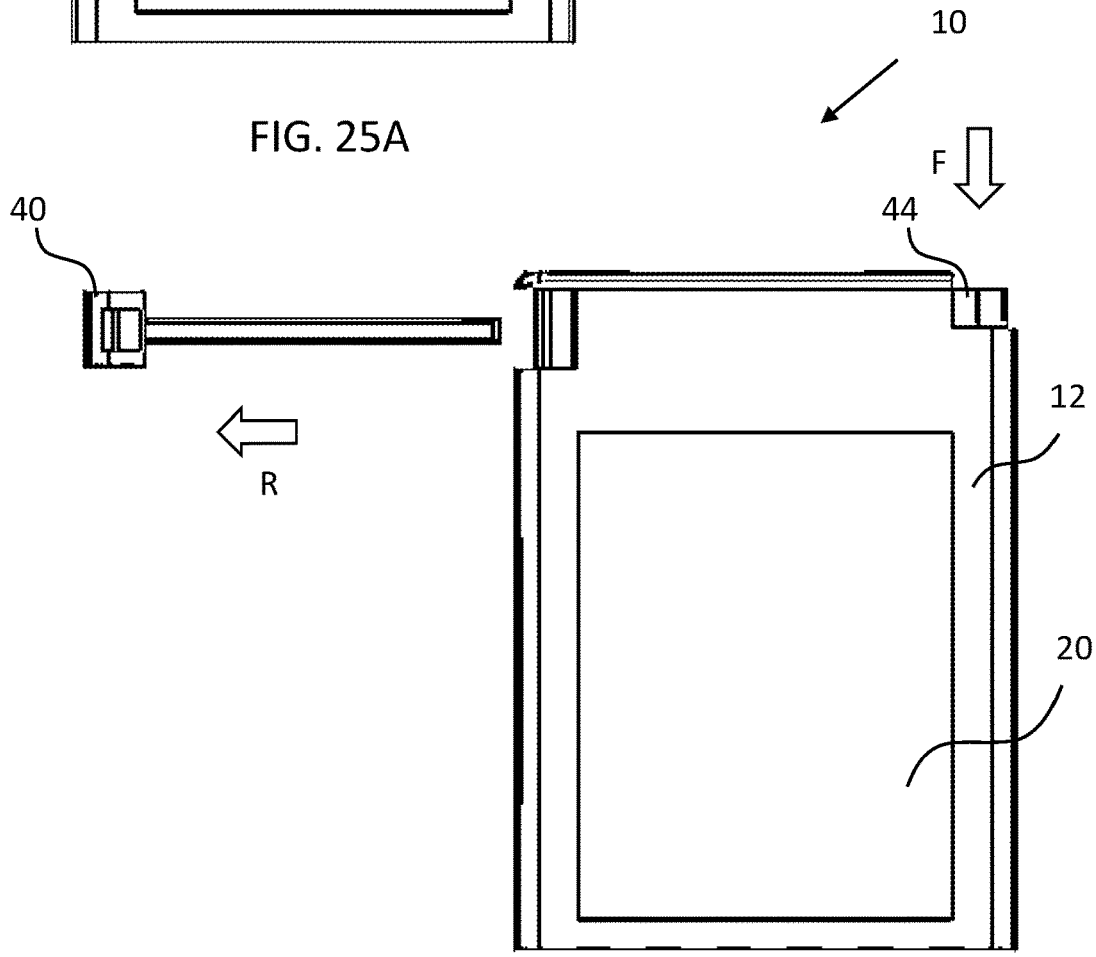
FIG. 25B is a side view of the injector of FIG. 25A during initiation of an injection operation.

FIGS. 25A and 25B illustrate a side view of an injector 10. The injector 10 includes a housing 12 having a removable cover 20. A stopper 40 is movably secured in the housing 12 so that, when the stopper 40 is moved, a button 44 may be activated to initiate articulation of the injector 10. To begin articulation of the injector 10, the stopper 40 is moved in a removal direction (R) to allow activation of the button 44. After removal of the stopper 40, the button 44 is activated by applying a force (F), which in turn initiates articulation of the injector 10 to administer a medication stored within the injector 10 (see FIGS. 25C-E).

Figure 25C:
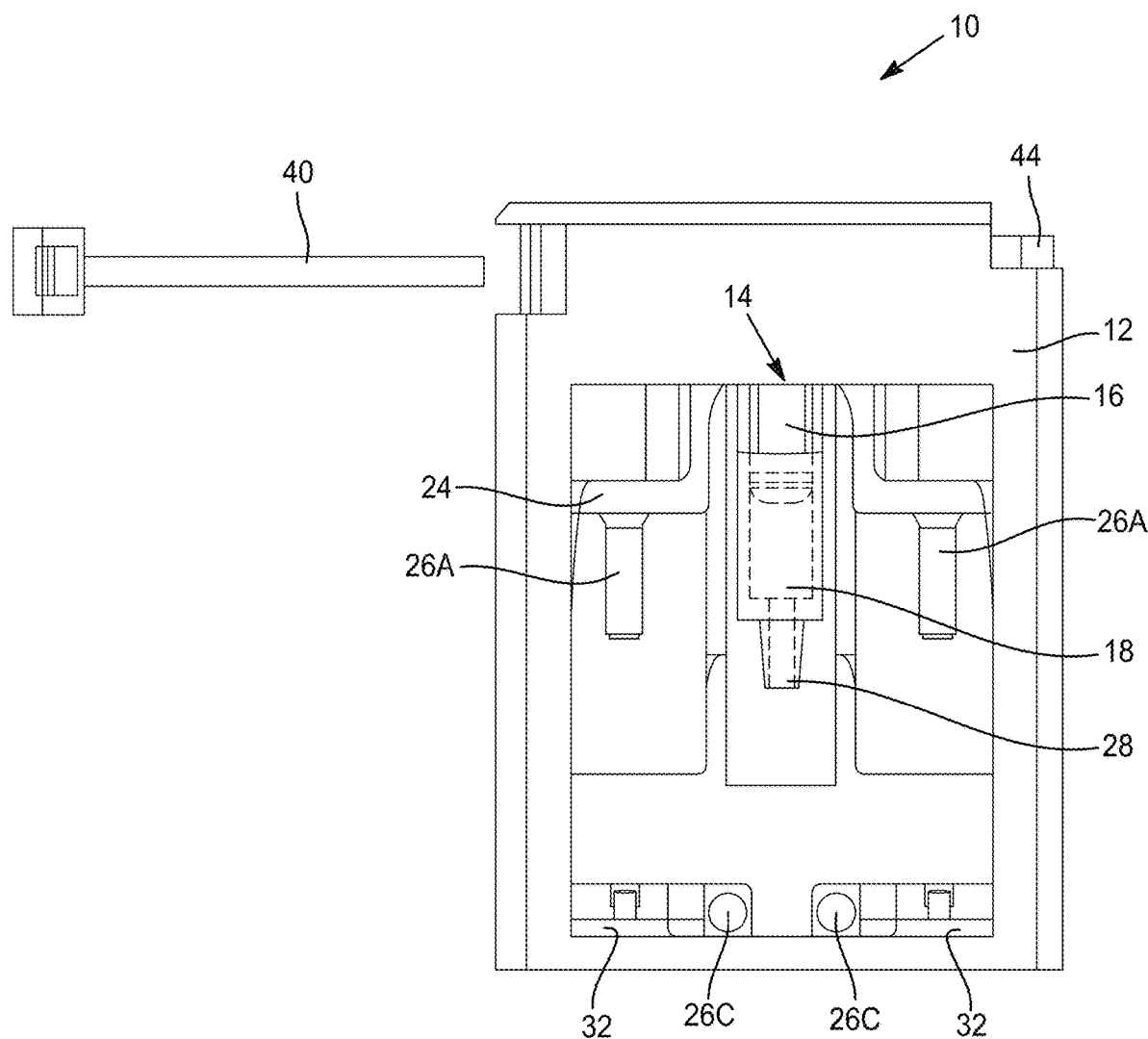
FIG. 25C is a side view of the injector of FIG. 25B with the cover removed.
Figure 25D:
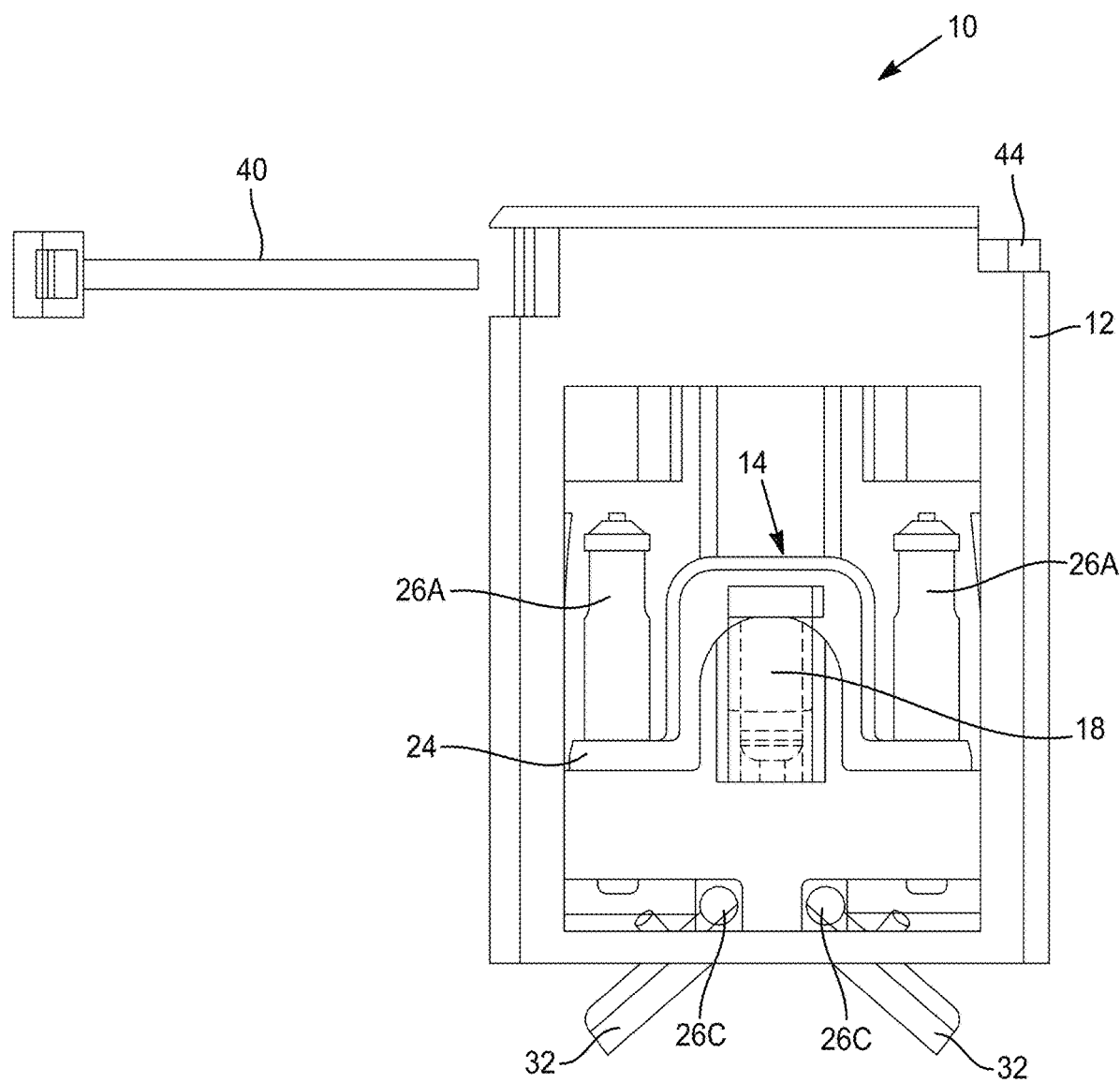
FIG. 25D is a side view of the injector of FIG. 25C in an engagement position.
Figure 25E:
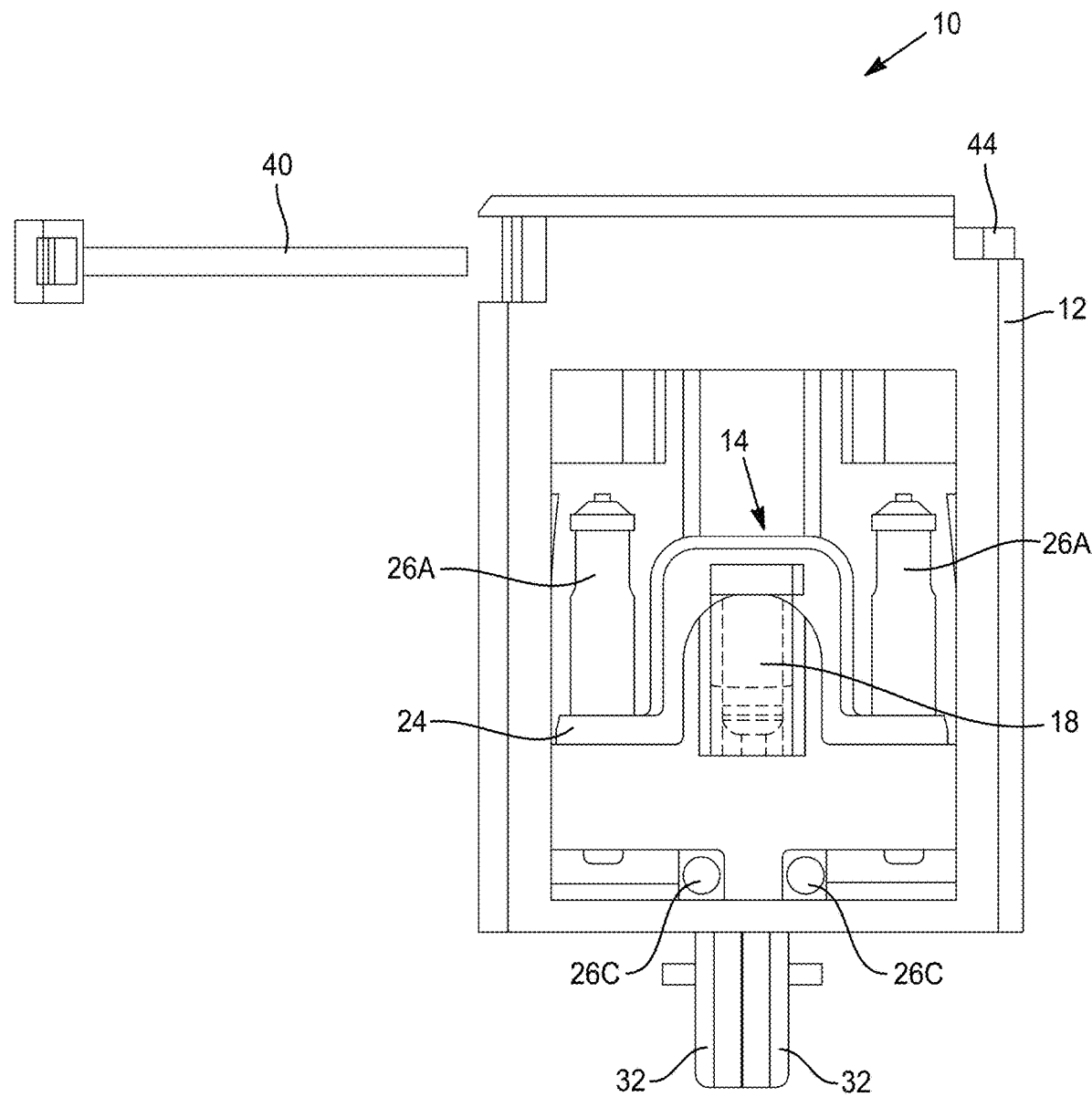
FIG. 25E is a side view of the injector of FIG. 25C in an extended position.

FIGS. 25C-25E illustrate a side view of the injector 10 of FIG. 11B with the cover 20 removed. As shown in FIG. 25C, the injector 10 includes a syringe 14 secured within a housing 12. The syringe 14 includes a plunger 16 configured to distribute a medication 18 into a needle 28 of the syringe 14 to administer to a user. To inject the medication 18 into the user, the injector 10 is positioned on a skin surface of the user and a stopper 40 securing a position of a control 24 is removed. After the stopper 40 is removed, a button 44 located on the housing 12 is activated so that the control 24 drives the syringe 14 via a first pair of biasing members 26A to expose the needle 28 and contact the skin surface of the user. As shown in FIG. 25D, the syringe 14 is driven until the syringe 14 contacts a surface of the housing 12 that prevents further movement of the syringe 14. Once the syringe 14 abuts the surface of the housing 12, the control 24 drives the plunger 16 into contact with the medication 18 so that the medication 18 is distributed into the needle 28 and then into the user. After injection, the injector 10 is removed from the skin surface so that two sheath halves 32 move via a pair of sheath biasing members 26C to enclose the needle 28 (see FIG. 25E).

Figure 26:
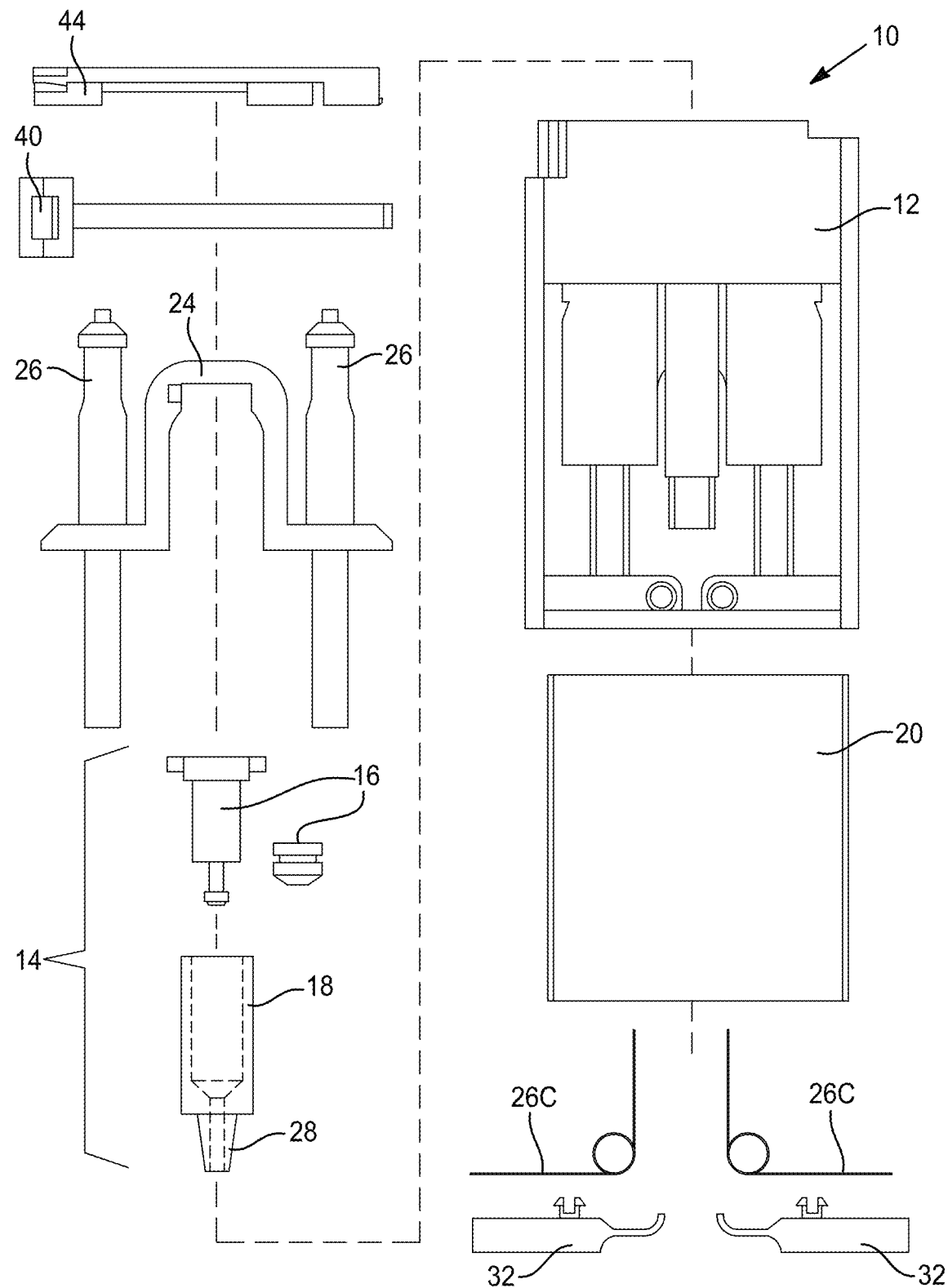
FIG. 26 is an exploded view of the injector of FIGS. 25A-25E.

FIG. 26 illustrates an exploded view of the injector 10 of FIGS. 25A-25E. The injector 10 includes a syringe 14 secured within a housing 12 have a cover 20. The syringe 14 includes a plunger 16 configured to distribute a medication 18 into a needle 28 of the syringe 14 to administer to a user. To inject the medication 18 into a user, the injector 10 is positioned on a skin surface of the user and a stopper 40 of the injector 10 is removed or articulated to allow activation of a button 44 located on the housing 12 of the injector 10. As shown, the stopper 40 may be a removable member. After the stopper 40 is removed, a force is applied to the button, which in turn releases a control 24 and drives the syringe 14 via a first pair of biasing members 26A to expose the needle 28 and contact a skin surface of the user (see FIGS. 25A-25E). The syringe 14 is driven until the syringe 14 contacts a surface of the housing 12 that prevents further movement of the syringe 14. Once the syringe 14 abuts the surface of the housing 12, the control 24 drives the plunger 16 into contact with the medication 18 so that the medication 18 is distributed into the needle 28 and then into the user. After injection, the injector 10 is removed from the skin surface so that two sheath halves 32 move via a pair of sheath biasing members 26C to enclose the needle 28.

Figure 27A:
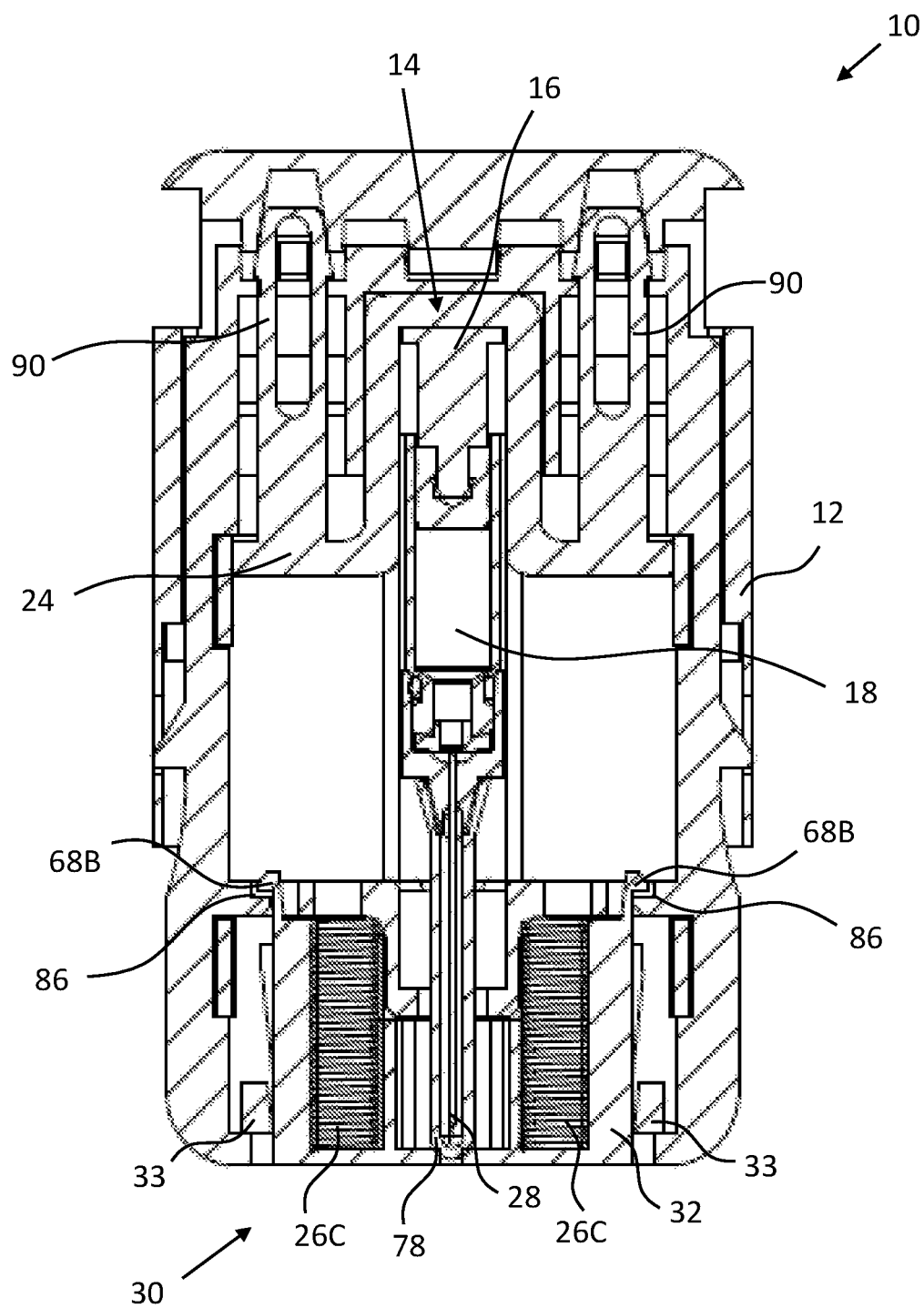
FIG. 27A is a cross-sectional view of an injector in a resting position prior to activation.
Figure 27B:
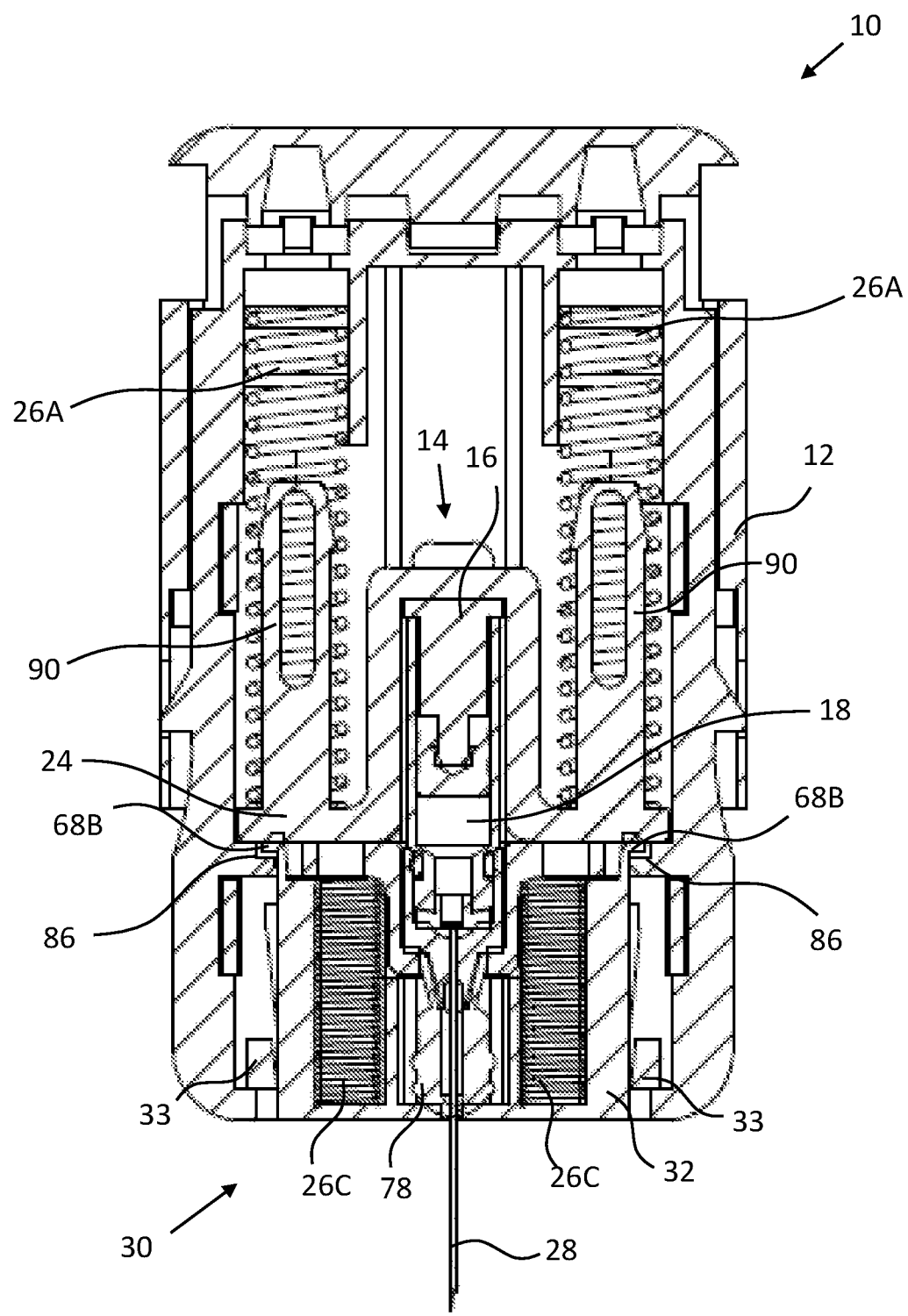
FIG. 27B is a cross-sectional view of the injector of FIG. 27A during injection.

FIGS. 27A and 27B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and the injector 10 is activated via a button or other activation device along a peripheral surface of the injector 10 (not shown; see, for example, FIG. 9A). Once the injector 10 is activated, a control 24 is released that drives the syringe 14 via a first pair of biasing members 26A secured around columns 90 of the control 24 to extend the needle 28 through a sterilization cover 78 to contact the skin surface of the user. The syringe 14 is driven until the control 24 contacts a pair of sheath engaging mechanisms 68B and an inner surface of the housing 12 that prevents further movement of the syringe 14. Once the syringe 14 contacts the inner surface of the housing 12, the control 24 drives the plunger 16 into contact with the medication 18 so that the medication 18 is distributed into the needle 28 and then into the user.

Figure 27C:
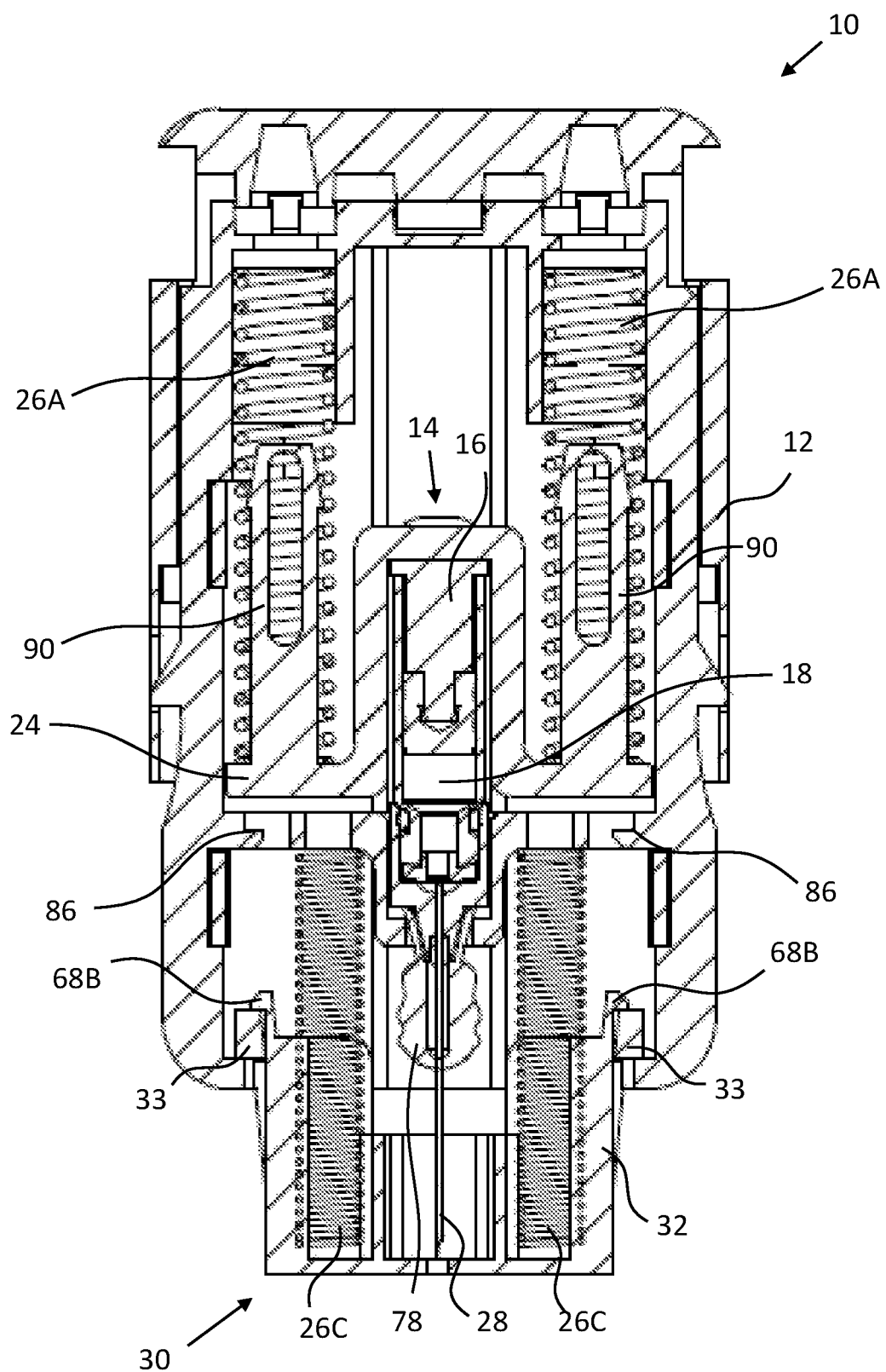
FIG. 27C is a cross-sectional view of the injector of FIG. 27A after injection with the sheath assembly fully extended.

After injection, as illustrated in FIG. 27C, the injector 10 is removed from the skin surface so that a sheath 32 of a sheath assembly 30 extends to enclose the exposed needle 28. As shown, the sheath 32 is biased against an inner portion of the housing 12 by a pair of sheath biasing members 26C so that, when the sheath engaging mechanisms 68B are contacted and released from shelves 86 of the housing 12 by the control 24 during injection, the sheath 32 extends to enclose the exposed needle 28 when the injector 10 is removed from the skin surface until the pair of sheath engaging mechanisms 68B are stopped by sheath brakes 33 of the housing 12. As illustrated, once the sheath 32 fully extends, the needle 28 is no longer exposed and is fully encapsulated within the sheath 32.

FIG. 28 illustrates the housing 12 of the injector of FIG. 27A. As illustrated, the housing 12 includes opposing shelves 86 that secure the sheath engagement mechanisms prior to release of the sheath engagement mechanisms by the control and articulation of the sheath (see FIGS. 27A-27C).

FIG. 29 illustrates a cover 20 that may be secured to the housing of FIG. 28 via a plurality of tabs 88 that engage slots, recesses, peripheral edges, or a combination thereof of the housing 12.

FIG. 30 illustrates the control 24 of the injector of FIG. 27A. The control 24 includes a pair of columns 90 configured to secure the first pair of biasing members by inserting the columns 90 into an interior portion of the first pair of biasing members (see FIGS. 27A-27C).

FIG. 31 illustrates the sheath assembly 30 of the injector of FIG. 27A. The sheath assembly 30 includes a sheath 32 the extends around an exposed needle to fully encapsulate the needle and prevent unwanted contact with the needle after injection. The sheath 32 is extended around the exposed needle by releasing a pair of sheath engagement mechanisms 68B from shelves of the housing of the injector (see FIGS. 27A-27C).

Figure 32A:
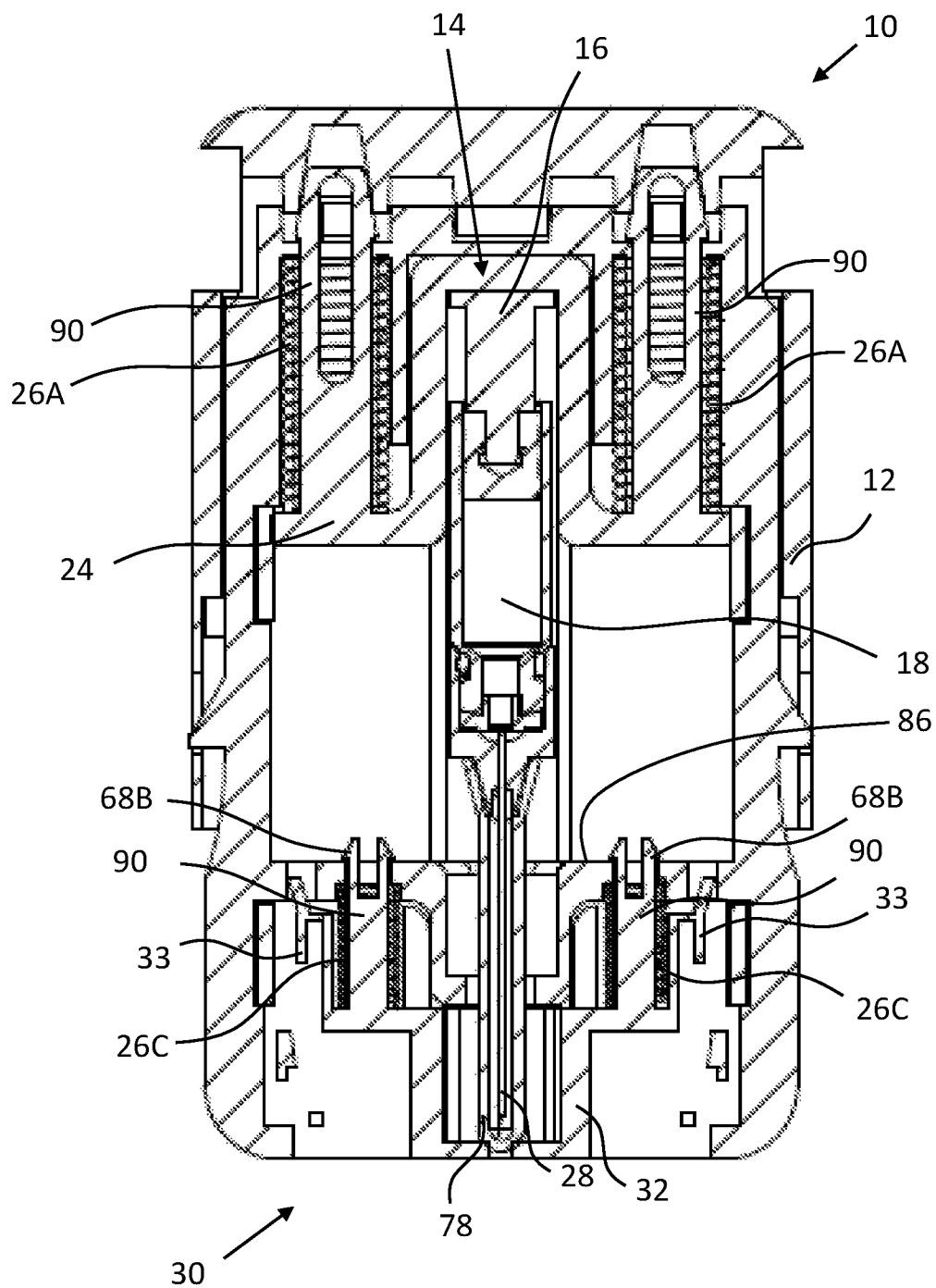
FIG. 32A is a cross-sectional view of an injector in a resting position prior to activation.
Figure 32B:
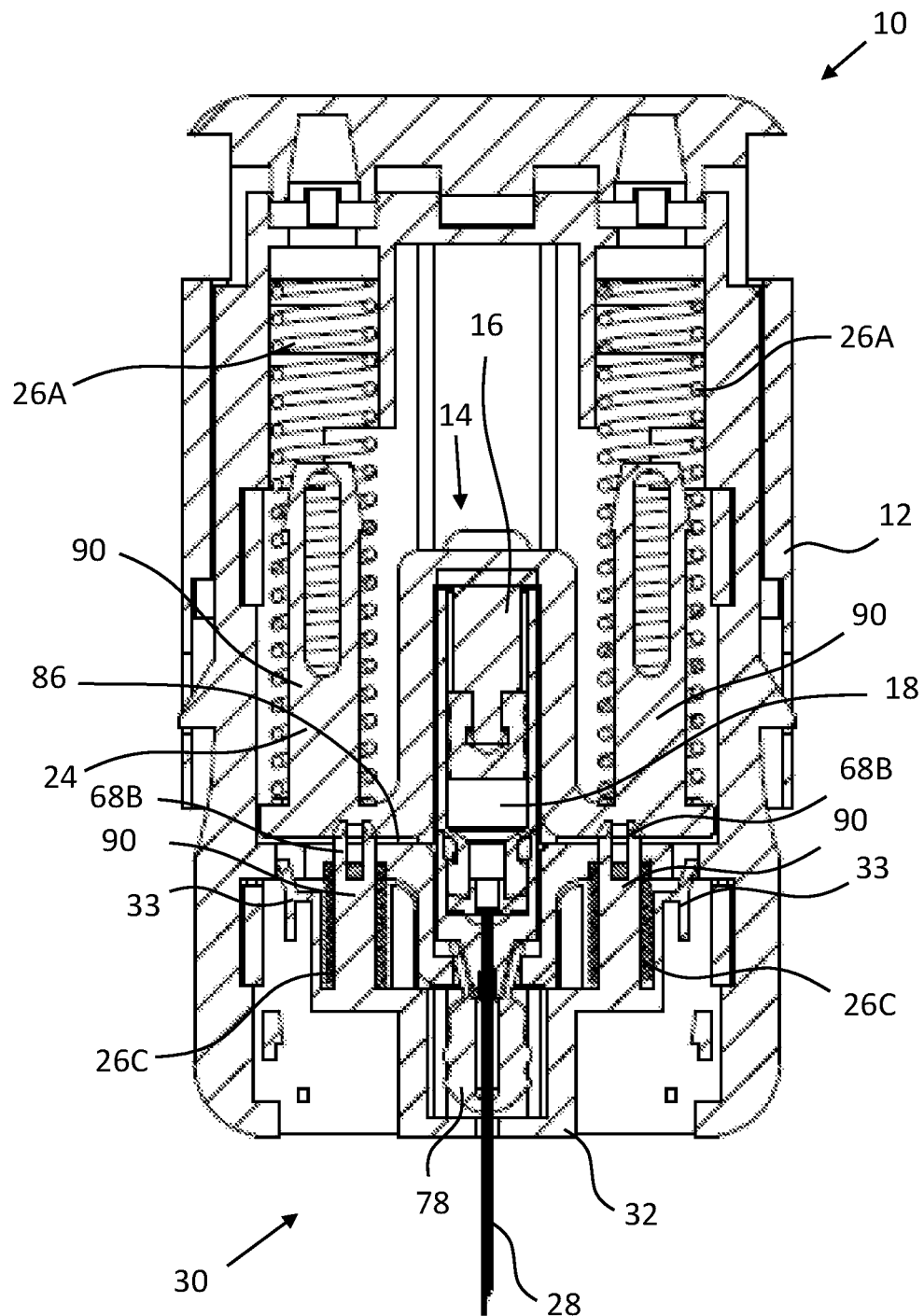
FIG. 32B is a cross-sectional view of the injector of FIG. 32A during injection.

FIGS. 32A and 32B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and the injector 10 is activated via a button or other activation device along a peripheral surface of the injector 10 (not shown; see, for example, FIG. 9A). Once the injector 10 is activated, a control 24 is released that drives the syringe 14 via a first pair of biasing members 26A secured around columns 90 of the control 24 to extend the needle 28 through a sterilization cover 78 to contact the skin surface of the user. The syringe 14 is driven until the control 24 contacts sheath engaging mechanisms 68B positioned within holes of the housing 12 and secured to a shelf 86 located within the housing 12. When the control 24 contacts the sheath engaging mechanisms 68B and the shelf 86, the syringe 14 is prevented from further movement. Once the syringe 14 is prevented from further movement within the housing 12, the control 24 drives the plunger 16 into contact with the medication 18 so that the medication 18 is distributed into the needle 28 and then into the user.

Figure 32C:
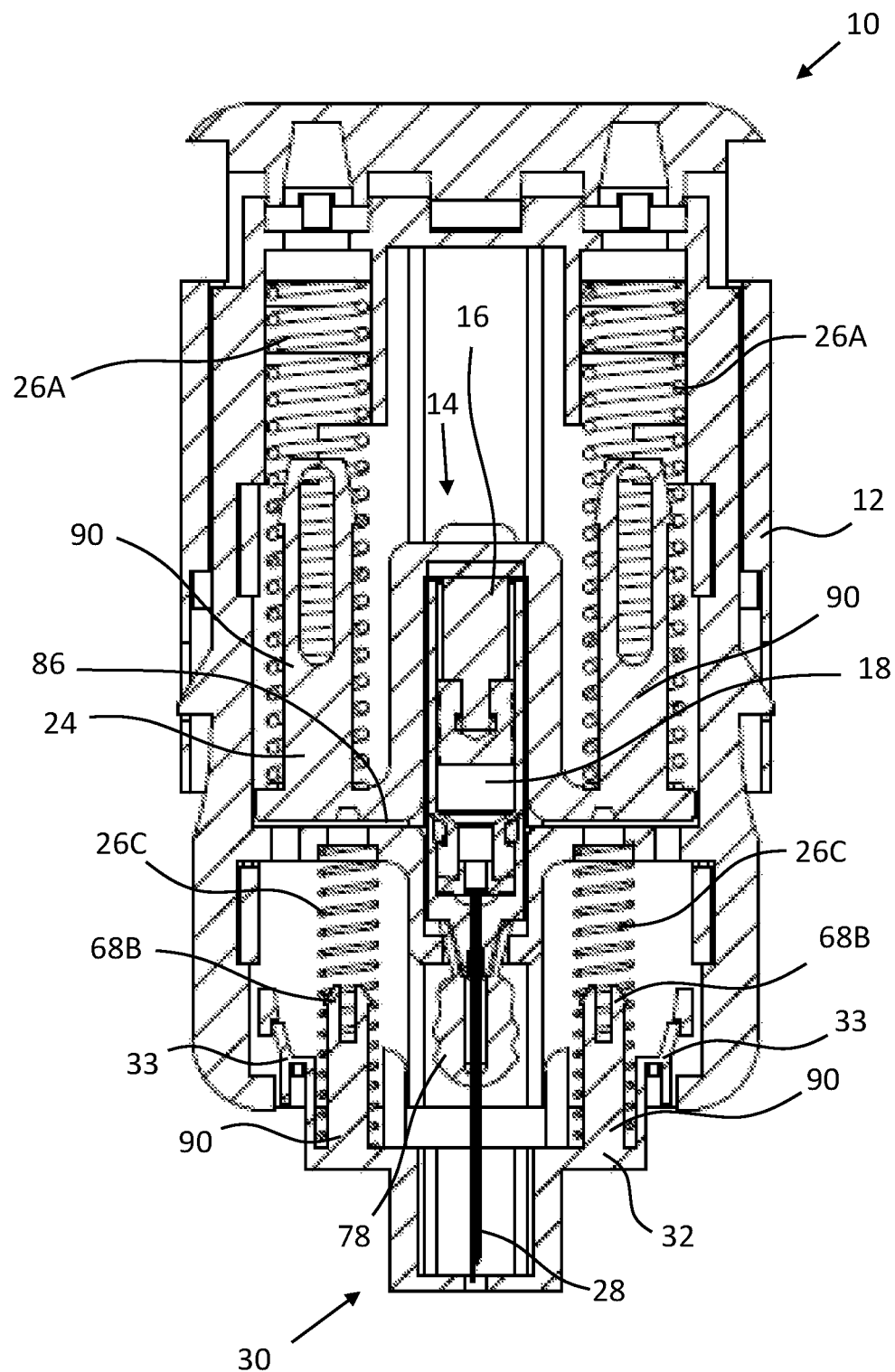
FIG. 32C is a cross-sectional view of the injector of FIG. 32A after injection with the sheath assembly fully extended.

After injection, as illustrated in FIG. 32C, the injector 10 is removed from the skin surface so that a sheath 32 of a sheath assembly 30 extends to enclose the exposed needle 28. As shown, the sheath 32 is biased against an inner portion of the housing 12 by a pair of sheath biasing members 26C secured around columns 90 of the sheath assembly 30 so that, when the sheath engaging mechanisms 68B are contacted and released from the shelf 86 of the housing 12 by the control 24 during injection, the sheath 32 extends to enclose the exposed needle 28 when the injector 10 is removed from the skin surface. The sheath 32 may extend until sheath brakes 33 of the sheath assembly 30 engage one or more projections, protrusions, walls, pegs, or a combination thereof of the housing 12 located within the housing 12. As illustrated, once the sheath 32 fully extends, the needle 28 is no longer exposed and is fully encapsulated within the sheath 32.

FIG. 33 illustrates the housing 12 of the injector of FIG. 32A. As illustrated, the housing 12 includes a shelf 86 that secures the sheath engagement mechanisms prior to release of the sheath engagement mechanisms through holes 42 of the housing by the control (see FIGS. 32A-32C).

FIG. 34 illustrates a cover 20 that may be secured to the housing of FIG. 33 via a plurality of tabs 88 that engage slots, recesses, peripheral edges, or a combination thereof of the housing 12.

FIG. 35 illustrates the control 24 of the injector of FIG. 32A. The control 24 includes a pair of columns 90 configured to secure the first pair of biasing members by inserting the columns 90 into an interior portion of the first pair of biasing members (see FIGS. 32A-32C).

FIG. 36 illustrates the sheath assembly 30 of the injector of FIG. 32A. The sheath assembly 30 includes a sheath 32 that extends around an exposed needle to fully encapsulate the needle and prevent unwanted contact with the needle after injection. The sheath 32 is extended around the exposed needle by releasing sheath engagement mechanisms 68B from a shelf of the housing of the injector and driving the sheath assembly 30 via a pair of sheath biasing members secured around columns 90 of the sheath assembly 30 until sheath brakes 33 contact a portion of the housing (see FIGS. 32A-32C).

Figure 37A:
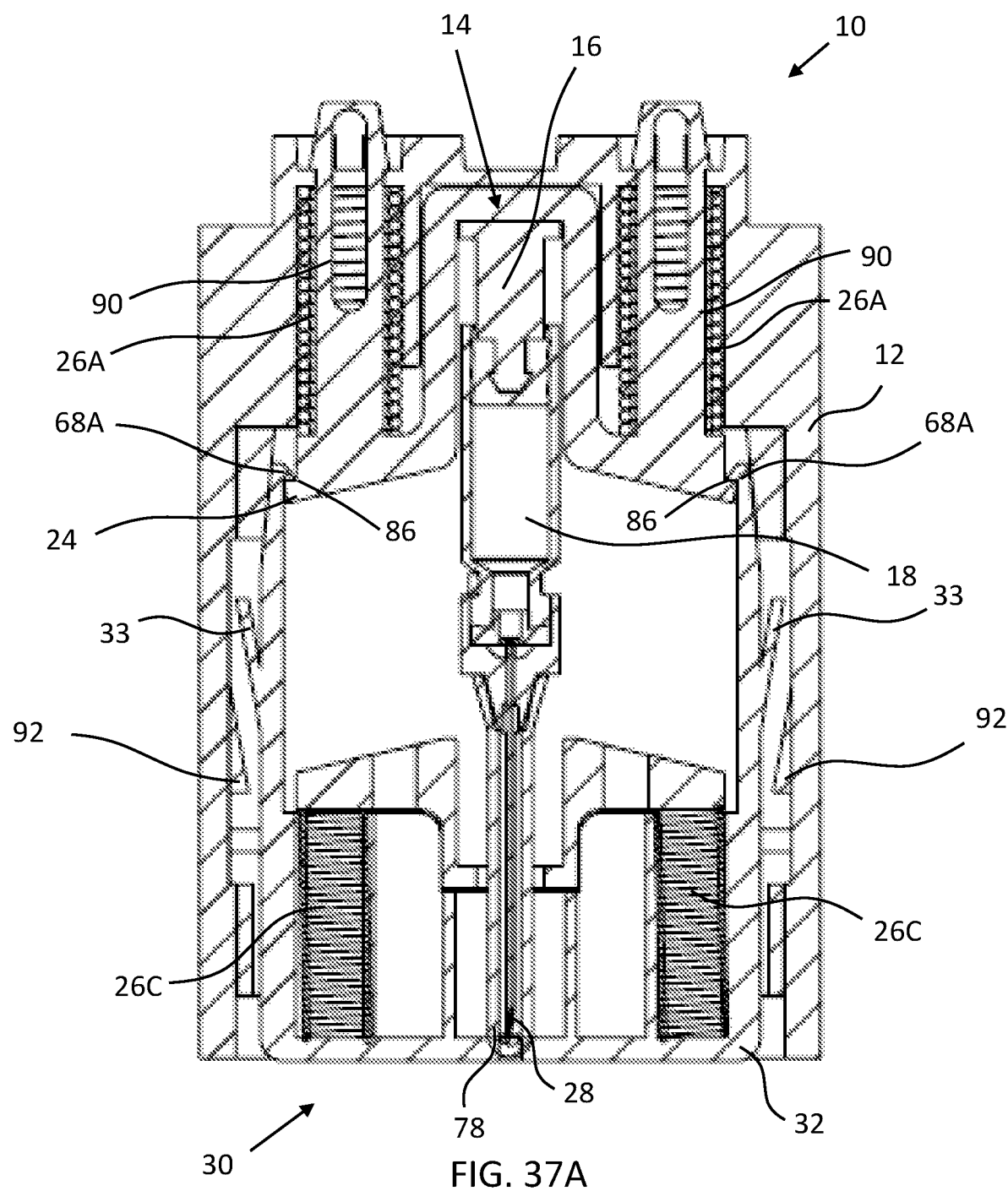
FIG. 37A is a cross-sectional view of an injector in a resting position prior to activation.
Figure 37B:
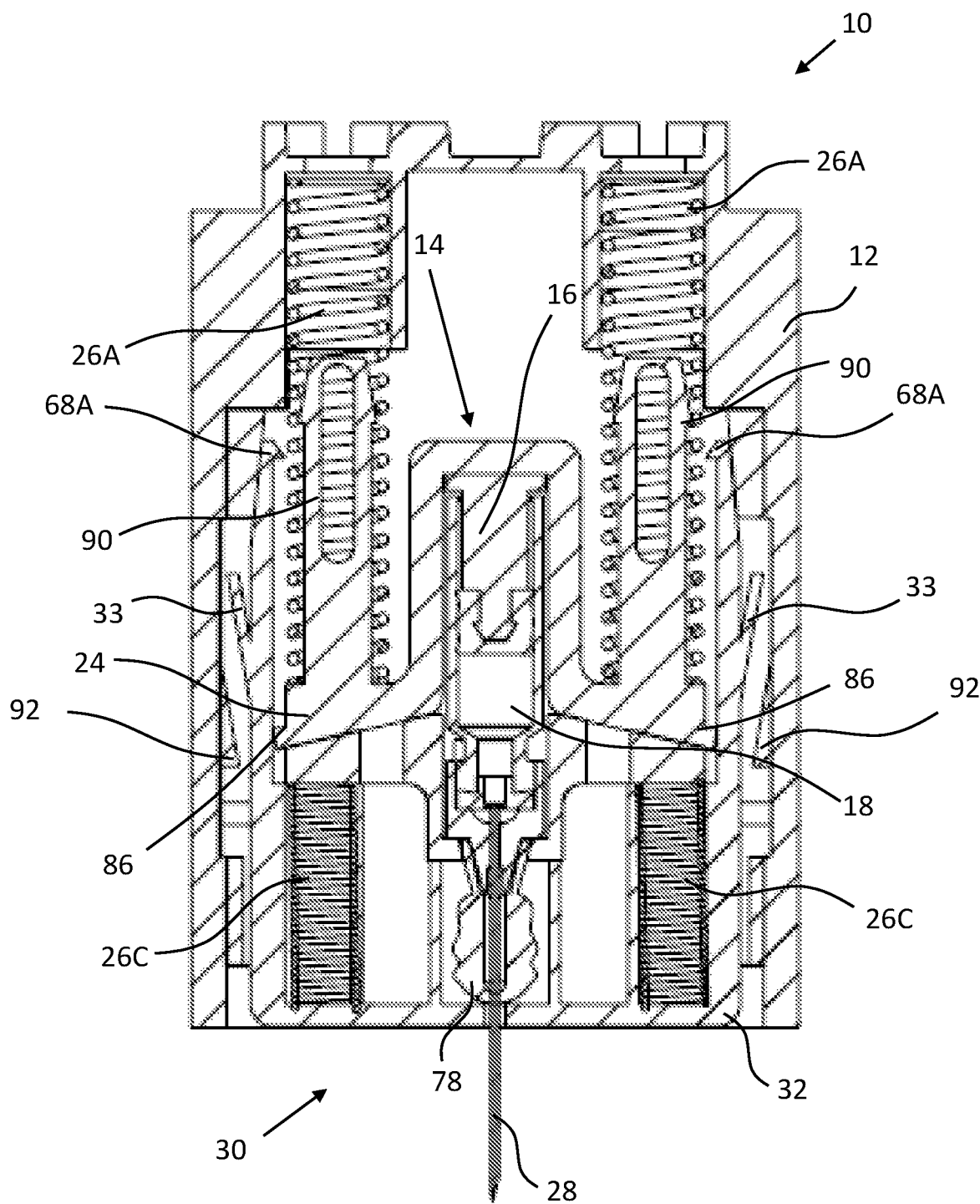
FIG. 37B is a cross-sectional view of the injector of FIG. 37A during injection.

FIGS. 37A 37B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and the injector 10 is activated via a button or other activation device along a peripheral surface of the injector 10 (not shown; see, for example, FIG. 9A). Once the injector 10 is activated, a control 24 is released that drives the syringe 14 via a first pair of biasing members 26A secured around columns 90 of the control 24 to extend the needle 28 through a sterilization cover 78 to contact the skin surface of the user. The syringe 14 is driven until the control 24 contacts an inner surface of the housing 12, thereby preventing further movement of the syringe 14. Once the syringe 14 is prevented from further movement within the housing 12, the control 24 drives the plunger 16 into contact with the medication 18 so that the medication 18 is distributed into the needle 28 and then into the user.

Figure 37C:
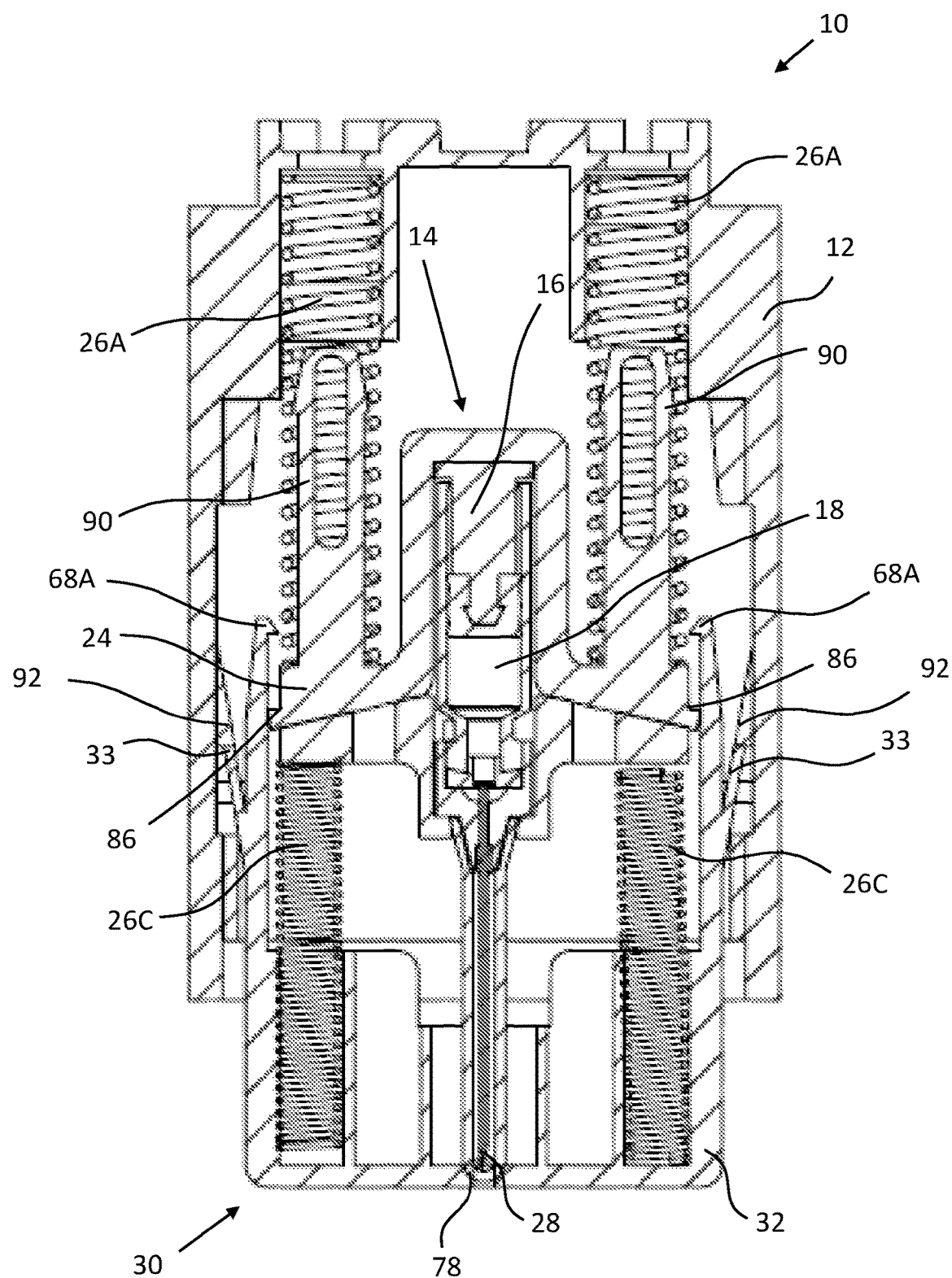
FIG. 37C is a cross-sectional view of the injector of FIG. 37A after injection with the sheath assembly fully extended.

After injection, as illustrated in FIG. 37C, the injector 10 is removed from the skin surface so that a sheath 32 of a sheath assembly 30 extends to enclose the exposed needle 28. As shown, the sheath 32 is biased against an inner portion of the housing 12 by a pair of sheath biasing members 26C. When the control 24 is driven during injection, shelves 86 of the control 24 are driven away from syringe engaging mechanisms 68A, thereby allowing the sheath assembly 30 to extend around the exposed needle 28. After release of the sheath engaging mechanisms 68A, the sheath assembly 30 may remain in place until the injector 10 is removed from the skin surface. Once the injector 10 is removed from the skin surface, the sheath assembly 30 may freely extend around the exposed needle until sheath brakes 33 abut teeth 92 along an inner wall of the housing 12 to prevent unwanted retraction of the sheath 32, exposure of the needle 28 after enclosure within the sheath 32, or both.

Figure 38:
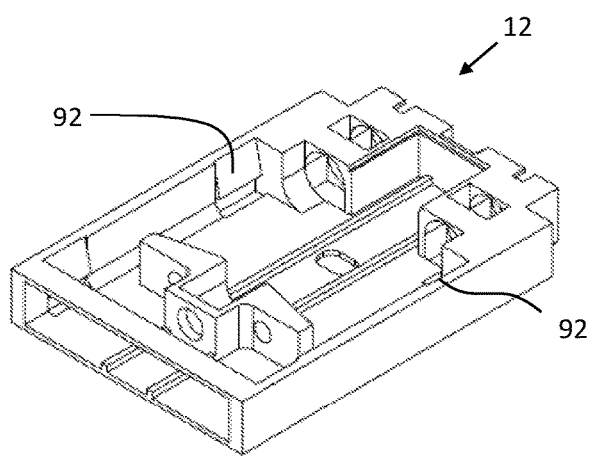
FIG. 38 is the housing of the injector of FIG. 37A.

FIG. 38 illustrates the housing 12 of the injector of FIG. 37A. As illustrated, the housing 12 includes teeth 92 along inner walls that abut the sheath brakes of the sheath assembly after extension of the sheath assembly around the exposed needle to prevent unwanted retraction of the sheath, exposure of the needle after enclosure within the sheath, or both (see FIGS. 37A-37O).

Figure 39:
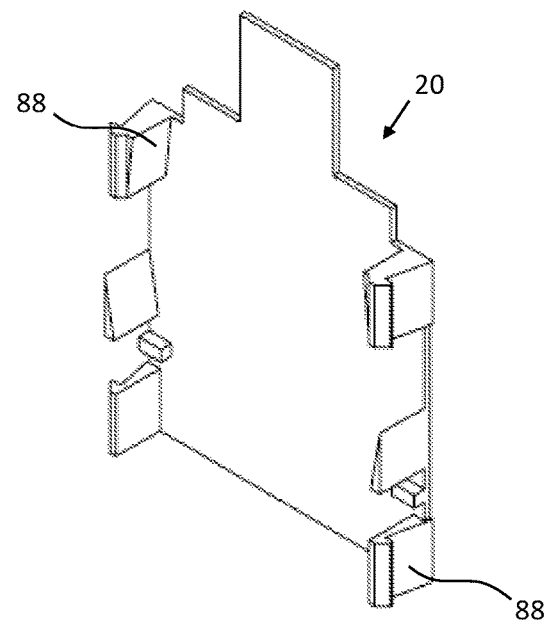
FIG. 39 is a cover for the housing of FIG. 38.

FIG. 39 illustrates a cover 20 that may be secured to the housing of FIG. 38 via a plurality of tabs 88 that engage slots, recesses, peripheral edges, or a combination thereof of the housing 12.

Figure 40:
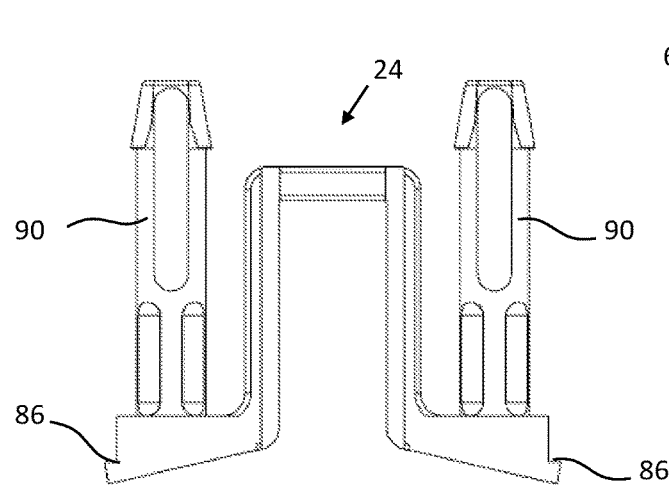
FIG. 40 is the control of the injector of FIG. 37A.

FIG. 40 illustrates the control 24 of the injector of FIG. 37A. The control 24 includes a pair of columns 90 configured to secure the first pair of biasing members by inserting the columns 90 into an interior portion of the first pair of biasing members (see FIGS. 37A-37C). The control 24 further includes a pair of shelves 86 that abut syringe engaging mechanisms of the sheath assembly prior to activation of the injector (see FIG. 37A).

Figure 41:
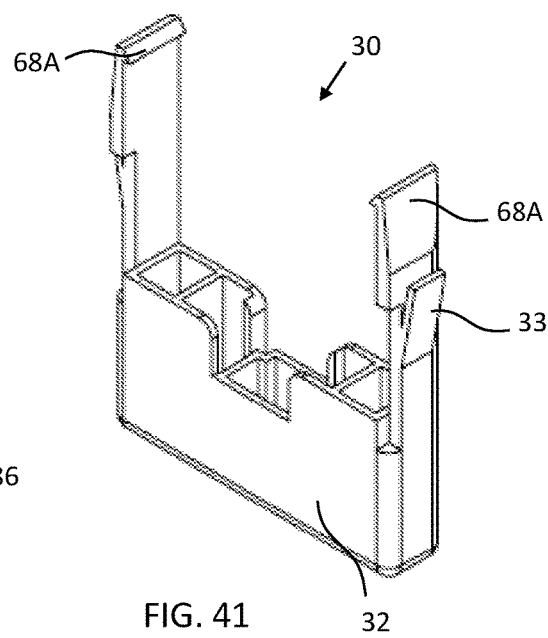
FIG. 41 is the sheath assembly of the injector of FIG. 37A.

FIG. 41 illustrates the sheath assembly 30 of the injector of FIG. 37A. The sheath assembly 30 includes a sheath 32 that extends around an exposed needle to fully encapsulate the needle and prevent unwanted contact with the needle after injection. The sheath 32 is extended around the exposed needle by releasing shelves of the control from syringe engagement mechanisms 68A, thereby allowing the sheath assembly 30 to extend until sheath brakes 33 abut teeth of the housing (see FIGS. 37A-37C).

Figure 42A:
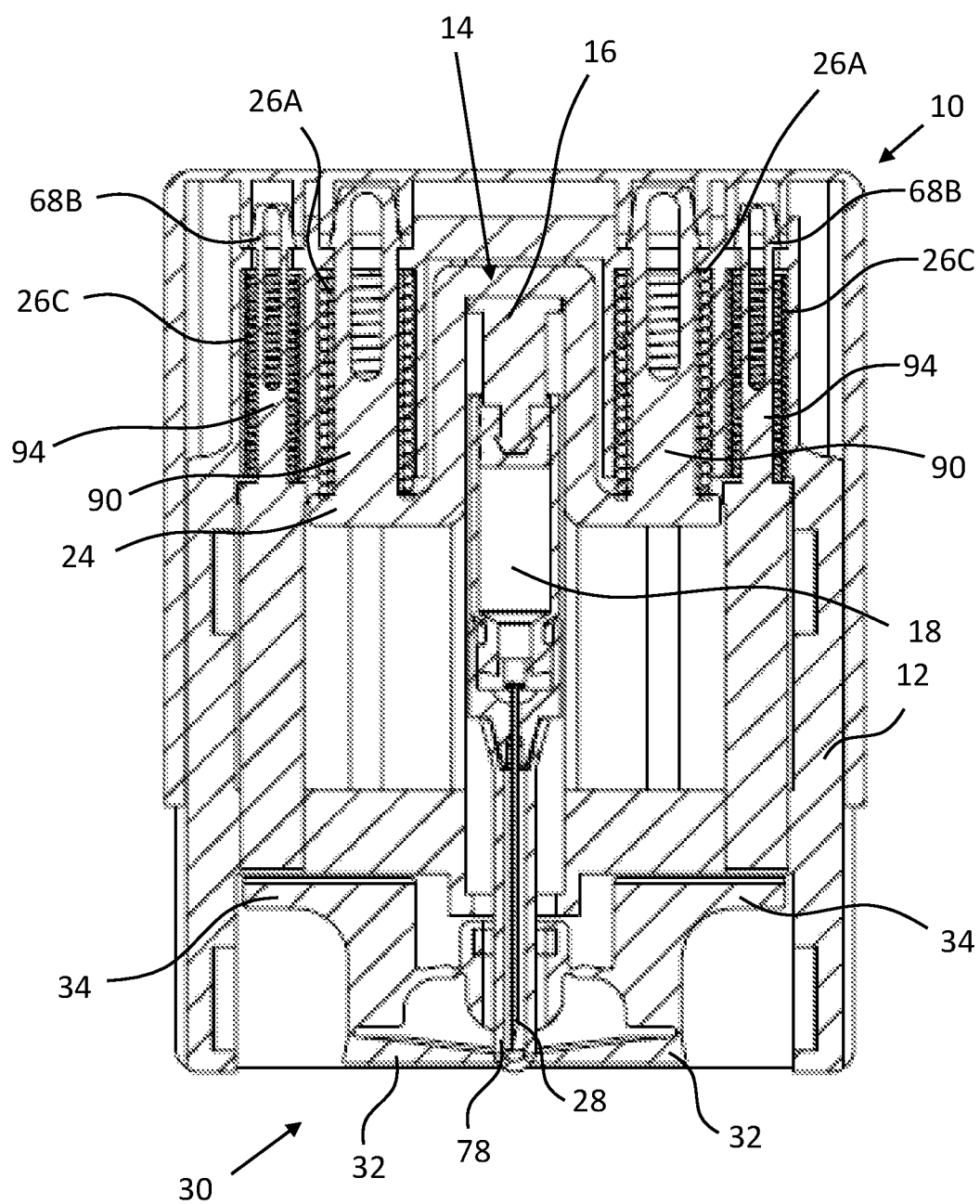
FIG. 42A is a cross-sectional view of an injector in a resting position prior to activation.
Figure 42B:
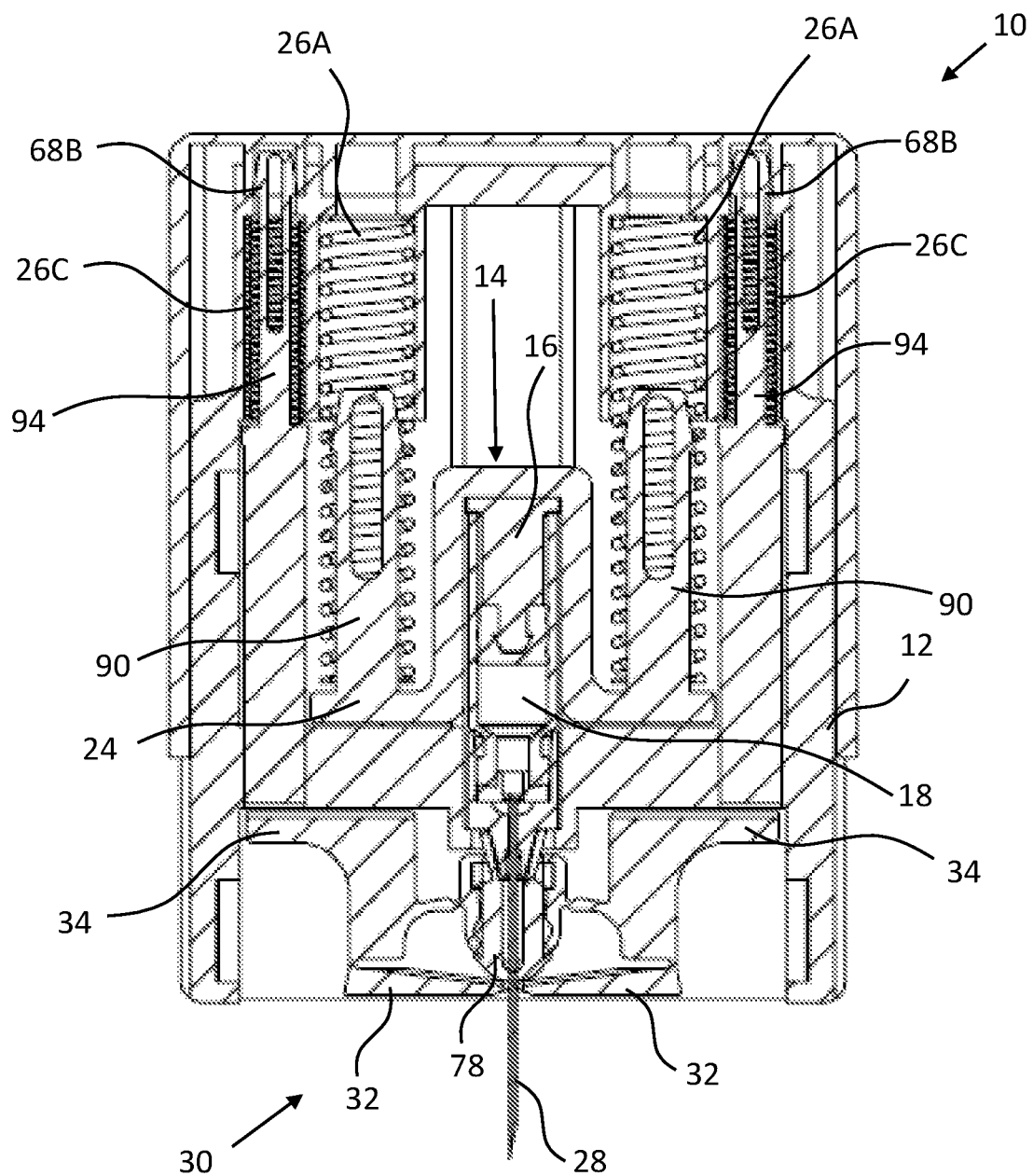
FIG. 42B is a cross-sectional view of the injector of FIG. 42A during injection.

FIGS. 42A and 42B illustrate an injector 10 in a resting position prior to activation and during injection, respectively. The injector 10 includes a syringe 14 secured within a housing 12. The syringe 14 includes a plunger 16 configured to distribute a medication 18 into a needle 28 of the syringe 14 to administer to a user. To inject the medication 18 into a user, the injector 10 is positioned on a skin surface of the user and the injector is activated via a button or other activation device along a peripheral surface of the injector 10 (not shown; see, for example, FIG. 9A). Once the injector 10 is activated, a control 24 is released that drives the syringe 14 via a first pair of biasing members 26A secured around columns 90 of the control 24 to extend the needle 28 through a sterilization cover 78 to contact the skin surface of the user. The syringe 14 is driven until the control 24 contacts an inner surface of the housing 12, thereby preventing further movement of the syringe 14. Once the syringe 14 is prevented from further movement within the housing 12, the control 24 drives the plunger 16 into contact with the medication 18 so that the medication 18 is distributed into the needle 28 and then into the user. During activation, sheath engaging mechanisms 68B of a pair of sheath drivers 94 are also released, thereby applying a biasing force against fingers 34 of a sheath assembly 30 via sheath biasing members 26C secured around the sheath drivers 94.

Figure 42C:
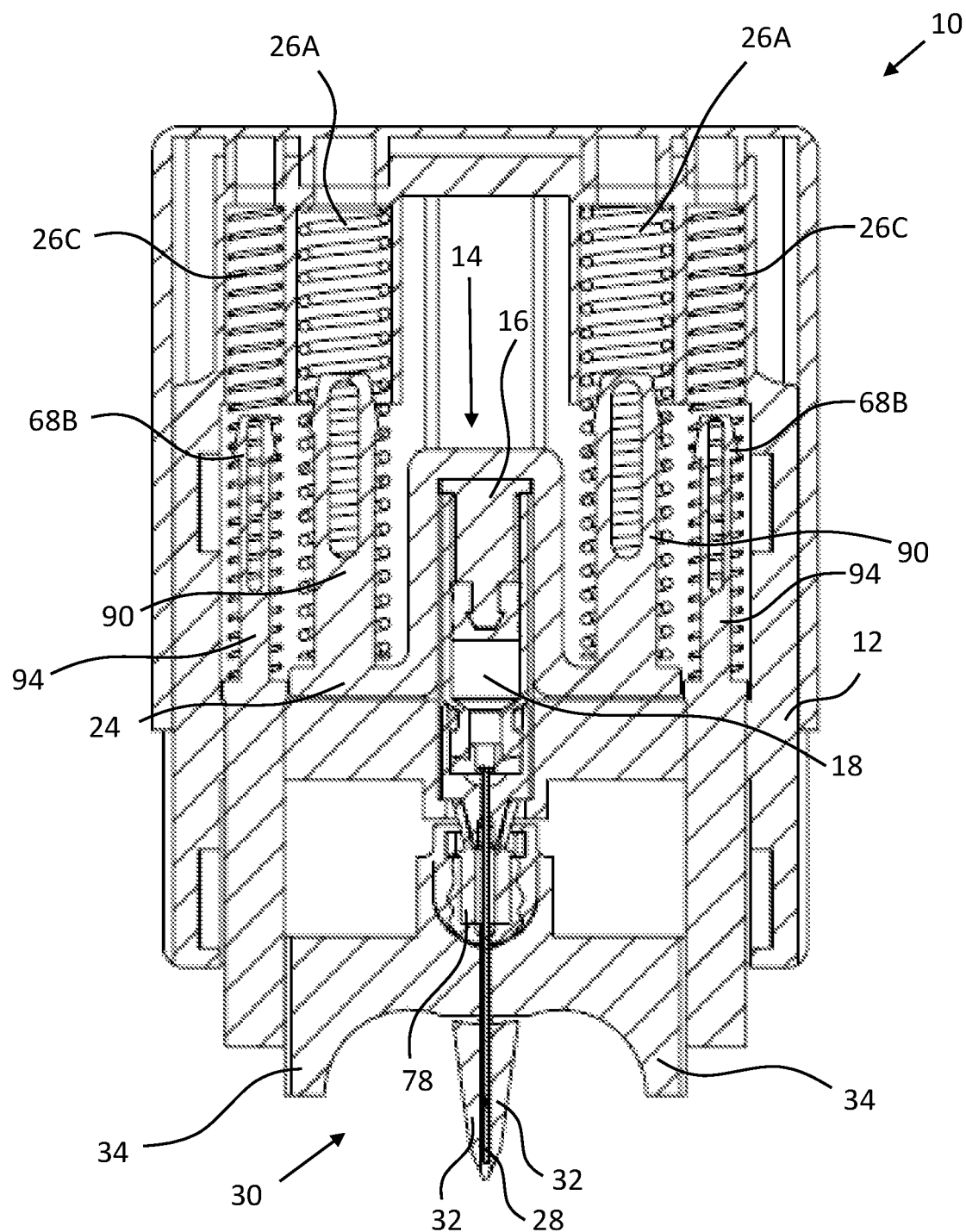
FIG. 42C is a cross-sectional view of the injector of FIG. 42A after injection with the sheath assembly fully extended.

After injection, as illustrated in FIG. 42C, the injector 10 is removed from the skin surface so that a sheath 32 of the sheath assembly 30 extends to enclose the exposed needle 28. As shown, once the injector 10 is removed from the skin surface, the biasing force being applied via the sheath drivers 94 articulates the fingers 34 so that the sheath 32 is positioned around the exposed needle 28.

FIG. 43 illustrates the housing 12 of the injector of FIG. 42A. As illustrated, the housing 12 includes holes 42 that allow extension of the sheath drivers into contact with the fingers of the sheath assembly so that the sheath assembly may be articulated to enclose the exposed needle (see FIGS. 42A-42C).

FIG. 44 illustrates the sheath drivers 94 of the injector of FIG. 42A. The sheath drivers 94 include a sheath engaging mechanism 68B that may be released from a portion of the housing securing the sheath driver during activation of the injector (see FIGS. 42A-42C).

FIG. 45 illustrates the sheath assembly 30 of the injector of FIG. 42A. The sheath assembly 30 includes a sheath 32 that extends around an exposed needle to fully encapsulate the needle and prevent unwanted contact with the needle after injection. The sheath 32 is extended around the exposed needle by articulating fingers 34 of the sheath assembly 30 via sheath drivers, thereby allowing the sheath 32 to extend around the exposed needle (see FIGS. 42A-42C).

As used herein, unless otherwise stated, the teachings envision that any member of a genus (list) may be excluded from the genus; and/or any member of a Markush grouping may be excluded from the grouping.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

Unless otherwise stated, a teaching with the term "about" or "approximately" in combination with a numerical amount encompasses a teaching of the recited amount, as well as approximations of that recited amount. By way of example, a teaching of "about 100" encompasses a teaching of 100+/−10.

The disclosures of all articles and references, including patent applications and publications, are incorporated by reference for ail purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist of, or consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

ELEMENT LIST

10 Injector
12 Housing
14 Syringe
16 Plunger
18 Medication
20 Cover
24 Control
26 Biasing Member
26A First Biasing Member (or First Pair)
26B Second Biasing Member (or Second Pair)
26C Sheath Biasing Member
28 Needle
30 Sheath Assembly
32 Sheath
33 Sheath Brake
34 Finger
36 Plate
38 Projection
40 Stopper
42 Hole
44 Button
46 Engaging Feature
60 Phone Case
62 Back Section
64 Injector Case
64A First Injector Case Section
64B Second Injector Case Section
66 Release Latch
68 Engaging Mechanism
68A Syringe Engaging Mechanism
68B Sheath Engaging Mechanism
70 First Platform
72 Second Platform
74 Protrusion
76 Cap
78 Sterilization Cover
80 Actuator
80A First Linear Actuator
80B Second Linear Actuator
82 Controller
84 Sensor
84A Near-Field Communication (NFC) Sensor
84B Temperature Sensor
86 Shelf
88 Tab
90 Column
92 Tooth
94 Sheath Driver
F Force (Applied to the Button)
R Removal Direction of the Stopper

What is claimed is:

1. An injector comprising:
a) a housing;
b) a syringe movably positioned within the housing, the syringe comprising a plunger and a needle, and housing a medication therein;
c) a removable member that is completely removable from the housing;
d) a control comprising a control release and releasably secured to the housing, wherein when released upon application of a force to the control release, the control automatically drives the syringe to expose the needle outside of the housing and automatically drives the plunger to distribute the medication through the needle; and
e) one or more biasing members disposed between engaging the housing and the control and moving the control upon applying the force to the control release;

wherein the removable member secures the control to the housing and prevents the control release from releasing the control and, after the removable member is removed from the injector, the control is releasable from the housing, upon application of the force, to engage the syringe; and wherein the injector is housed within a mobile device case or within an injector case secured to the mobile device case.

2. The injector according to claim 1, wherein the removable member is a pin, a latch, a hook, a projection, a fastener, a clip, or any combination thereof.

3. The injector according to claim 2, wherein the removable member engages both the housing and the control release prior to release of said engagement.

4. The injector according to claim 3, wherein the force is applied manually by a user.

5. The injector according to claim 4, wherein the syringe is driven until the syringe contacts the housing, at which time the control drives the plunger.

6. The injector according to claim 5, wherein movement of the control is mutual with the syringe.

7. The injector according to claim 6, wherein movement of the control is mutual with the plunger.

8. The injector according to claim 7, wherein movement of the control is mutual with the syringe in a first movement stage and mutual with the plunger in a second movement stage; and wherein the second movement stage comes after the first movement stage.

9. The injector according to claim 8, wherein the one or more biasing members that move the control function for both exposing of the needle and distribution of the medication.

10. The injector according to claim 9, wherein the control directly engages the plunger.

11. The injector according to claim 10, wherein the one or more biasing members include two biasing members arranged on opposing sides of the syringe.

12. The injector according to claim 1, wherein the injector is configured for one injection or a plurality of injections.

13. The injector according to claim 1, wherein the injector is housed within the injector case and the injector case is releasably secured to the mobile device case.

14. The injector according to claim 13, wherein a first section of the injector case is fixedly secured to the mobile device case and a second section of the injector case is removably secured to the mobile device case.

15. The injector according to claim 14, wherein the second section of the injector case is fixedly attached to the injector.

16. The injector according to claim 14, wherein the second section of the injector case is a portion of the housing of the injector.

17. The injector of claim 1, including one or more near-field communication sensors adapted to identify and/or monitor a location of the injector with reference to a mobile device that is connected to the housing, a temperature of the injector, or both.

18. The injector of claim 17, wherein a user receives a notification that the temperature of the injector is outside of a predetermined acceptable range.

19. The injector according to claim 1, further comprising a sheath in movable communication with the housing in response to movement of the control by the one or more biasing members; wherein, when the control is released, the sheath is released from the housing and biased to automatically cover the portion of the syringe that is exposed; and wherein the sheath extends until one or more sheath brakes engage the housing and prevent further movement of the sheath.

20. The injector according to claim 19, wherein the one or more biasing members that move the control function for exposing the needle, distribution of the medication, and extension of the sheath.

* * * * *